US010340460B2

(12) United States Patent
Fukumatsu et al.

(10) Patent No.: US 10,340,460 B2
(45) Date of Patent: Jul. 2, 2019

(54) ORGANIC ELECTROLUMINESCENT ELEMENT

(71) Applicants: NIPPON STEEL & SUMIKIN CHEMICAL CO., LTD., Tokyo (JP); PIONEER CORPORATION, Kawasaki-shi, Kanagawa (JP); TOHOKU PIONEER CORPORATION, Tendo-shi, Yamagata (JP)

(72) Inventors: Takayuki Fukumatsu, Kitakyushu (JP); Katsuhide Noguchi, Kitakyushu (JP); Masashi Tada, Kitakyushu (JP); Mitsuru Sakai, Kitakyushu (JP); Tohru Asari, Kitakyushu (JP); Kazuto Shiraishi, Kitakyushu (JP); Takahiro Kai, Kitakyushu (JP); Yasuhiro Takahashi, Kawasaki (JP); Yuhki Terao, Kawasaki (JP); Taishi Tsuji, Kawasaki (JP); Yusuke Nakajima, Yonezawa (JP); Toshinao Yuki, Yonezawa (JP)

(73) Assignees: NIPPON STEEL CHEMICAL & MATERIAL CO., LTD., Tokyo (JP); PIONEER CORPORATION, Kanagawa (JP); TOHOKU PIONEER CORPORATION, Yamagata (JP)

( * ) Notice: Subject to any disclaimer, the term of this patent is extended or adjusted under 35 U.S.C. 154(b) by 412 days.

(21) Appl. No.: 14/389,003

(22) PCT Filed: Mar. 25, 2013

(86) PCT No.: PCT/JP2013/058515
§ 371 (c)(1),
(2) Date: Sep. 29, 2014

(87) PCT Pub. No.: WO2013/146645
PCT Pub. Date: Oct. 3, 2013

(65) Prior Publication Data
US 2015/0115240 A1    Apr. 30, 2015

(30) Foreign Application Priority Data

Mar. 30, 2012 (JP) .................. 2012-080154

(51) Int. Cl.
*H01L 51/54* (2006.01)
*C09K 11/06* (2006.01)
(Continued)

(52) U.S. Cl.
CPC ........ H01L 51/0058 (2013.01); C07D 209/86 (2013.01); C07D 401/14 (2013.01);
(Continued)

(58) Field of Classification Search
CPC .. C07D 401/00; C07D 401/14; C07D 209/82; C07D 209/86; C07D 487/00; C07D 487/02; C07D 487/04; C07D 519/00; C09K 2211/00; C09K 2211/10; C09K 2211/1003; C09K 2211/1007; C09K 2211/1081; C09K 2211/1029; C09K 2211/1033; C09K 2211/104; C09K 2211/1059; C09K 2211/1088; C09K 2211/1092; C09K 2211/185; C09K 11/06; H05B 33/14; H01L 51/0032; H01L 51/005; H01L 51/0052; H01L 51/0058; H01L 51/0068; H01L 51/0071; H01L 51/0072; H01L 51/0073; H01L 51/0074; H01L 51/0061; H01L 51/0067; H01L 51/0085; H01L 51/0087; H01L 51/008; H01L 51/009; H01L 51/50; H01L 51/5012; H01L 51/5016; H01L 2251/50; H01L 2251/53; H01L 2251/5384
(Continued)

(56) References Cited

U.S. PATENT DOCUMENTS

2006/0099447 A1    5/2006    Lee et al.
2009/0295276 A1   12/2009    Asari et al.
(Continued)

FOREIGN PATENT DOCUMENTS

JP           2009-55010 A       3/2009
JP    WO 2011155507 A1 *  12/2011  ......... H01L 51/5004
(Continued)

OTHER PUBLICATIONS

Schrogel et al. Organic Electronics 2011, 12, 2047-2055. (Year: 2011).*

(Continued)

*Primary Examiner* — Andrew K Bohaty
(74) *Attorney, Agent, or Firm* — Cheng Law Group, PLLC

(57) ABSTRACT

Provided is a practically useful organic electroluminescent device (organic EL device) having high efficiency and high driving stability while being capable of being driven at a low voltage. The organic electroluminescent device includes a light-emitting layer between an anode and a cathode opposite to each other. The light-emitting layer contains two host materials and at least one light-emitting dopant. One of the two host materials is a host material selected from an indolocarbazole compound having one indolocarbazole ring and an indolocarbazole compound having two indolocarbazole rings, and the other thereof is a host material selected from carbazole compounds.

4 Claims, 1 Drawing Sheet

(51) Int. Cl.
*H01L 51/00* (2006.01)
*C07D 401/14* (2006.01)
*C07D 487/04* (2006.01)
*C07D 519/00* (2006.01)
*C07D 209/86* (2006.01)
*H05B 33/14* (2006.01)
*H01L 51/50* (2006.01)

(52) U.S. Cl.
CPC ......... *C07D 487/04* (2013.01); *C07D 519/00* (2013.01); *C09K 11/06* (2013.01); *H01L 51/0052* (2013.01); *H01L 51/0061* (2013.01); *H01L 51/0067* (2013.01); *H01L 51/0068* (2013.01); *H01L 51/0071* (2013.01); *H01L 51/0072* (2013.01); *H01L 51/0073* (2013.01); *H01L 51/0074* (2013.01); *H01L 51/0085* (2013.01); *H01L 51/0087* (2013.01); *H01L 51/0088* (2013.01); *H01L 51/5012* (2013.01); *H05B 33/14* (2013.01); *C09K 2211/1007* (2013.01); *C09K 2211/1029* (2013.01); *C09K 2211/1033* (2013.01); *C09K 2211/1044* (2013.01); *C09K 2211/1059* (2013.01); *C09K 2211/1088* (2013.01); *C09K 2211/1092* (2013.01); *C09K 2211/185* (2013.01); *H01L 51/008* (2013.01); *H01L 51/009* (2013.01); *H01L 51/5016* (2013.01); *H01L 2251/5384* (2013.01)

(58) Field of Classification Search
USPC ....... 428/690, 691, 917, 411.4, 336; 427/58, 427/66; 313/500–512; 257/40, 88–104, 257/E51.001–E51.052; 252/301.16–301.35
See application file for complete search history.

(56) References Cited

U.S. PATENT DOCUMENTS

| | | |
|---|---|---|
| 2009/0302742 A1* | 12/2009 | Komori ............... C07D 487/04 313/504 |
| 2010/0171418 A1 | 7/2010 | Kinoshita et al. |
| 2010/0187977 A1* | 7/2010 | Kai ..................... C07D 487/04 313/504 |
| 2011/0024735 A1* | 2/2011 | Sawada ............... C07D 209/86 257/40 |
| 2011/0062862 A1 | 3/2011 | Yamamoto et al. |
| 2011/0279020 A1* | 11/2011 | Inoue .................. C07D 209/82 313/504 |
| 2012/0001158 A1 | 1/2012 | Asari et al. |
| 2012/0007070 A1* | 1/2012 | Kai ..................... H01L 51/0072 257/40 |
| 2012/0138912 A1 | 6/2012 | Inoue et al. |
| 2012/0138915 A1 | 6/2012 | Nishimura et al. |
| 2013/0075716 A1* | 3/2013 | Nishimura ......... H01L 51/5016 257/40 |

FOREIGN PATENT DOCUMENTS

| | | | |
|---|---|---|---|
| KR | 10-2010-0131745 A | 12/2010 | |
| WO | WO 2010098246 A1 * | 9/2010 | ........... C07D 487/04 |
| WO | WO 2010113761 A1 * | 10/2010 | ......... H01L 51/0072 |
| WO | WO-2012087955 A1 * | 6/2012 | ............. C09K 11/06 |

OTHER PUBLICATIONS

Son et al. Chem. Mater. 2008, 20, 4439-4446. (Year: 2008).*
International Search Report for Application No. PCT/JP2013/058515 dated Jun. 25, 2013.
Written Opinion of the International Searching Authority (PCT/ISA/237) for Application No. PCT/JP2013/058515 dated Jun. 25, 2013.

* cited by examiner

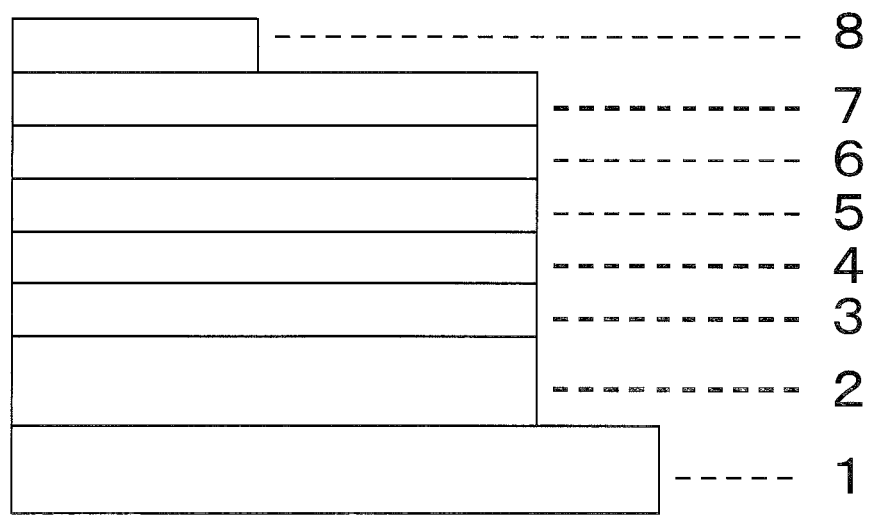

ORGANIC ELECTROLUMINESCENT ELEMENT

TECHNICAL FIELD

The present invention relates to an organic electroluminescent device (hereinafter referred to as "organic EL device"), and more specifically, to an organic EL device that uses a mixture of compounds each having a specific structure, and hence can achieve high efficiency and a long lifetime while being capable of being driven at a low voltage.

BACKGROUND ART

In general, an organic EL device includes a light-emitting layer and a pair of counter electrodes interposing the light-emitting layer therebetween in its simplest structure. That is, the organic EL device uses the phenomenon that, when an electric field is applied between both the electrodes, electrons are injected from a cathode and holes are injected from an anode, and each electron and each hole recombine in the light-emitting layer to emit light as energy.

In recent years, progress has been made in developing an organic EL device using an organic thin film. In order to enhance luminous efficiency particularly, the optimization of the kind of electrodes has been attempted for the purpose of improving the efficiency of injection of carriers from the electrodes. As a result, there has been developed a device in which a hole-transporting layer formed of an aromatic diamine and a light-emitting layer-cum-electron-transporting layer formed of an 8-hydroxyquinoline aluminum complex (hereinafter referred to as Alq3) are formed between electrodes as thin films, resulting in a significant improvement in luminous efficiency, compared with conventional devices in which a single crystal of anthracene or the like is used. Thus, the development of the above-mentioned organic EL device has been promoted in order to accomplish its practical application to a high-performance flat panel having features such as self-luminescence and rapid response.

Studies have also been made on using a phosphorescent light-emitting material rather than a fluorescent light-emitting material as an attempt to raise the luminous efficiency of a device. Many kinds of devices including the above-mentioned device in which a hole-transporting layer formed of an aromatic diamine and a light-emitting layer formed of Alq3 are formed use fluorescent light emission. However, by using phosphorescent light emission, that is, by using light emission from a triplet excited state, luminous efficiency is expected to be improved by about three times to four times, compared with the case of using conventional devices in which fluorescent light (singlet) is used. In order to accomplish this purpose, studies have been made on adopting a coumarin derivative or a benzophenone derivative as a light-emitting layer, but extremely low luminance has only been provided. After that, studies have been made on using a europium complex as an attempt to use a triplet state, but highly efficient light emission has not been accomplished. Among the studies involving using phosphorescent light emission, many studies on a phosphorescent light-emitting dopant centered on an organometallic complex such as an iridium complex have been made, as described in Patent Literature 1, and ones capable of highly efficient light emission have been found.

CITATION LIST

Patent Literature

[PTL 1] WO 01/041512 A1
[PTL 2] JP 2001-313178 A
[PTL 3] JP 2002-352957 A
[PTL 4] JP 11-162650 A
[PTL 5] JP 11-176578 A
[PTL 6] WO 2008-056746 A1
[PTL 7] WO 2009-136596 A1
[PTL 8] WO 2010-098246 A1
[PTL 9] WO 2011-132683 A1
[PTL 10] WO 2011-132684 A1
[PTL 11] JP 2012-028634 A

Examples of a host material to be used in the light-emitting layer of the organic EL device include carbazole-based compounds introduced in Patent Literatures 1 and 2, and an oxazole-based compound and triazole-based compound introduced in Patent Literature 3. However, none of the compounds can be put into practical use in terms of both efficiency and lifetime.

In addition, Patent Literatures 4 and 5 each disclose an indolocarbazole compound. However, each of the literatures recommends the use of the indolocarbazole compound as a hole-transporting material, does not disclose the use of the indolocarbazole compound as a mixed host material, and does not teach the usefulness of the indolocarbazole compound as the mixed host material.

In addition, Patent Literature 6 discloses the use of an indolocarbazole compound as a host material, but does not teach the usefulness of the indolocarbazole compound as a mixed host material.

In addition, each of Patent Literatures 7 and 8 discloses the use of an indolocarbazole compound as a mixed host, but does not teach that the combination of the compound with a specific carbazole compound expresses a useful effect.

In addition, each of Patent Literatures 9, 10, and 11 discloses the use of an indolocarbazole compound and a carbazole compound as a mixed host, but does not teach any useful effect of the combination of a specific indolocarbazole compound and a specific carbazole compound like the present invention.

SUMMARY OF INVENTION

In order to apply an organic EL device to a display device in a flat panel display or the like, it is necessary to improve the luminous efficiency of the device and also to ensure sufficiently the stability in driving the device. The present invention has an object to provide, in view of the above-mentioned circumstances, a practically useful organic EL device that has high efficiency and high driving stability while being capable of being driven at a low voltage.

The present invention relates to an organic electroluminescent device, including one or more light-emitting layers between an anode and a cathode opposite to each other, in which:

at least one of the light-emitting layers contains two host materials and at least one light-emitting dopant; and one of the two host materials includes a host material selected from compounds each represented by any one of the following general formulae (1) to (2), and another of the two host materials includes a host material selected from compounds each represented by the following general formula (3).

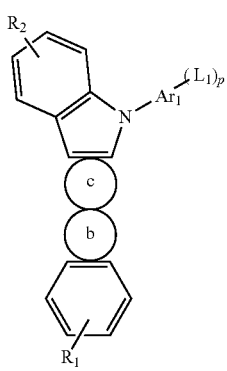

(1)

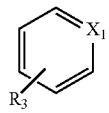

(a1)

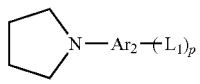

(b1)

(Wherein, a ring a represents an aromatic ring or heterocycle represented by the formula (a1) condensed at arbitrary positions of two adjacent rings, $X_1$ represents C—R or N, a ring b represents a heterocycle represented by the formula (b1) condensed at arbitrary positions of two adjacent rings, $Ar_1$ and $Ar_2$ each represent an aromatic hydrocarbon group having 6 to 22 carbon atoms or a monocyclic aromatic heterocyclic group having 3 to 6 carbon atoms, $L_1$ represents an aromatic hydrocarbon group having 6 to 22 carbon atoms, an aromatic heterocyclic group having 3 to 16 carbon atoms, or a group obtained by linking 2 to 10 of the groups, the aromatic hydrocarbon groups or aromatic heterocyclic groups in $Ar_1$, $Ar_2$, and $L_1$ may each have a substituent, p represents an integer of from 0 to 7, and when p represents 2 or more, $L_1$s may be identical to or different from each other, and R and $R_1$ to $R_3$ each independently represent hydrogen, an alkyl group having 1 to 20 carbon atoms, an aralkyl group having 7 to 38 carbon atoms, an alkenyl group having 2 to 20 carbon atoms, an alkynyl group having 2 to 20 carbon atoms, a dialkylamino group having 2 to 40 carbon atoms, a diarylamino group having 12 to 44 carbon atoms, a diaralkylamino group having 14 to 76 carbon atoms, an acyl group having 2 to 20 carbon atoms, an acyloxy group having 2 to 20 carbon atoms, an alkoxy group having 1 to 20 carbon atoms, an alkoxycarbonyl group having 2 to 20 carbon atoms, an alkoxycarbonyloxy group having 2 to 20 carbon atoms, an alkylsulfonyl group having 1 to 20 carbon atoms, an aromatic hydrocarbon group having 6 to 22 carbon atoms, or an aromatic heterocyclic group having 3 to 16 carbon atoms, and may each have a substituent.)

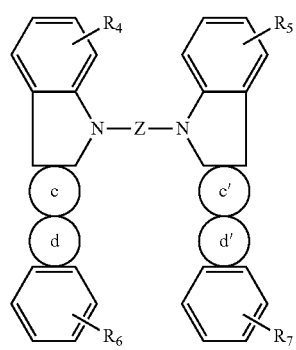

(2)

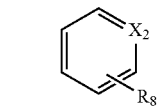

(c1)

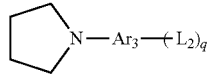

(d1)

(Wherein, a ring c and a ring c' each represent an aromatic ring or heterocycle represented by the formula (c1) condensed at an arbitrary position of an adjacent ring, a ring d and a ring d' each represent a heterocycle represented by the formula (d1) condensed at an arbitrary position of an adjacent ring, and the ring c and the ring c', or the ring d and the ring d' may be identical to or different from each other, $X_2$ represents C—R' or N, Z represents an aromatic hydrocarbon group having 6 to 22 carbon atoms, an aromatic heterocyclic group having 3 to 16 carbon atoms, or a divalent linking group obtained by linking 2 to 10 of the groups, but a group linked to N includes an aromatic hydrocarbon group having 6 to 22 carbon atoms or a monocyclic aromatic heterocyclic group having 3 to 6 carbon atoms, $Ar_3$ represents an aromatic hydrocarbon group having 6 to 22 carbon atoms or a monocyclic aromatic heterocyclic group having 3 to 6 carbon atoms, $L_2$ represents an aromatic hydrocarbon group having 6 to 22 carbon atoms, an aromatic heterocyclic group having 3 to 16 carbon atoms, or a group obtained by linking 2 to 10 of the groups, the aromatic hydrocarbon groups or aromatic heterocyclic groups in Z, $Ar_3$, and $L_2$ may each have a substituent, q represents an integer of from 0 to 7, and when q represents 2 or more, $L_2$s may be identical to or different from each other, and R' and $R_4$ to $R_8$ each independently represent hydrogen, an alkyl group having 1 to 20 carbon atoms, an aralkyl group having 7 to 38 carbon atoms, an alkenyl group having 2 to 20 carbon atoms, an alkynyl group having 2 to 20 carbon atoms, a dialkylamino group having 2 to 40 carbon atoms, a diarylamino group having 12 to 44 carbon atoms, a diaralkylamino group having 14 to 76 carbon atoms, an acyl group having 2 to 20 carbon atoms, an acyloxy group having 2 to 20 carbon atoms, an alkoxy group having 1 to 20 carbon atoms, an alkoxycarbonyl group having 2 to 20 carbon atoms, an alkoxycarbonyloxy group having 2 to 20 carbon atoms, an alkylsulfonyl group having 1 to 20 carbon atoms, an aromatic hydrocarbon group having 6 to 22 carbon atoms, or an aromatic heterocyclic group having 3 to 16 carbon atoms, and may each have a substituent.)

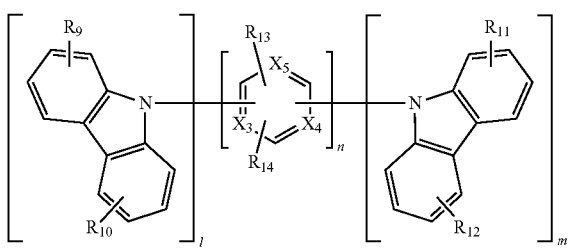

(3)

(Wherein, $R_9$ to $R_{12}$ each independently represent hydrogen, an alkyl group having 1 to 20 carbon atoms, an acyl group having 2 to 20 carbon atoms, or an alkoxy group having 2 to 20 carbon atoms, l and m each represent an integer of 1 or 2, n represents an integer of from 1 to 6, $R_{13}$ and $R_{14}$ each independently represent hydrogen or an alkyl group having 1 to 20 carbon atoms, and $X_3$ to $X_5$ each independently represent C—H or N, and when n represents 2 or more, $R_{13}$s, $R_{14}$s, and $X_3$s is to $X_5$s may be identical to or different from each other.

In addition, according to another embodiment of the present invention, in the above-mentioned organic electroluminescent device, one of the two host materials includes a host material selected from the compounds each represented by any one of the general formulae (1) to (2), another of the two host materials includes a host material selected from the compounds each represented by the general formula (3), and a difference in electron affinity (ΔEA) between the two host materials is more than 0.1 eV.)

In the general formula (1), it is preferred that at least one of $Ar_1$ and $Ar_2$ represent a substituted or unsubstituted, monocyclic aromatic heterocyclic group having 3 to 6 carbon atoms, and $X_1$ in the formula (a1) represent C—R. In addition, in the general formula (2), it is preferred that $X_2$ of the formula (c1) represent C—R'.

In addition, according to another embodiment of the present invention, in the organic electroluminescent device, the light-emitting dopant includes a phosphorescent light-emitting dopant formed of an organometallic complex containing at least one metal selected from ruthenium, rhodium, palladium, silver, rhenium, osmium, iridium, platinum, and gold.

BRIEF DESCRIPTION OF DRAWINGS

FIG. 1 is a schematic sectional view illustrating an example of an organic EL device.

DESCRIPTION OF EMBODIMENTS

An organic electroluminescent device of the present invention is an organic electroluminescent device including one or more light-emitting layers between an anode and a cathode opposite to each other, in which: at least one of the light-emitting layers contains two host materials and at least one light-emitting dopant; and one of the two host materials is a host material selected from compounds each represented by any one of the following general formulae (1) to (2), and the other thereof is a host material selected from compounds each represented by the following general formula (3).

In the general formula (1) or (2), a ring a, a ring c, and a ring c' each represent an aromatic ring or heterocycle represented by the formula (a1) or (c1) condensed at arbitrary positions of two adjacent rings. Here, in the formula (a1), $X_1$ represents C—R or N, preferably C—R. In addition, in the formula (c1), $X_2$ represents C—R' or N, preferably C—R'.

In the general formula (1) or (2), a ring b, a ring d, and a ring d' each represent a heterocycle represented by the formula (b1) or (d1) condensed at arbitrary positions of two adjacent rings. Here, the ring c and the ring c', or the ring d and the ring d' may be identical to or different from each other.

In a compound represented by the general formula (1) or (2), an aromatic hydrocarbon ring or heterocycle represented by the formula (a1) or (c1) can be condensed to two adjacent rings at arbitrary positions but has a position at which the ring or heterocycle cannot be structurally condensed. The aromatic hydrocarbon ring or heterocycle represented by the formula (a1) or (c1) has six sides but is not condensed to the two adjacent rings on two adjacent sides. In addition, in the general formula (1) or (2), a heterocycle represented by the formula (b1) or (d1) can be condensed to two adjacent rings at arbitrary positions but has a position at which the heterocycle cannot be structurally condensed. That is, the heterocycle represented by the formula (b1) or (d1) has five sides but is not condensed to the two adjacent rings on two adjacent sides. In addition, the heterocycle is not condensed to any adjacent ring on a side containing a nitrogen atom. Therefore, the number of kinds of the skeletons of the isomers of the compounds represented by the general formulae (1) and (2) is limited.

In the general formula (1), the formula (b1), and the formula (d1), $Ar_1$ to $Ar_3$ each represent an aromatic hydrocarbon group having 6 to 22 carbon atoms or a monocyclic aromatic heterocyclic group having 3 to 6 carbon atoms, and such aromatic hydrocarbon groups or aromatic heterocyclic groups may each have a substituent.

$Ar_1$ to $Ar_3$ each represent preferably an aromatic hydrocarbon group having 6 to 22 carbon atoms or a monocyclic aromatic heterocyclic group having 3 to 6 carbon atoms, more preferably an aromatic hydrocarbon group having 6 to 18 carbon atoms or a monocyclic aromatic heterocyclic group having 3 to 5 carbon atoms, and the monocyclic aromatic heterocyclic group is preferably a six-membered ring. $Ar_1$ and $Ar_2$ each represent a p+1-valent group, and $Ar_3$ represents a q+1-valent group.

Specific examples of $Ar_1$ to $Ar_3$ include groups each produced by removing p+1 or q+1 hydrogen atoms from benzene, pentalene, indene, naphthalene, azulene, heptalene, octalene, indacene, acenaphthylene, phenalene, phenanthrene, anthracene, trindene, fluoranthene, acephenanthrylene, aceanthrylene, triphenylene, pyrene, chrysene, tetraphene, tetracene, pleiadene, picene, perylene, pentaphene, pentacene, tetraphenylene, cholanthrylene, helicene, hexaphene, rubicene, coronene, trinaphthylene, heptaphene, pyranthrene, furan, thiophene, pyrrole, pyrazole, tellurazole, selenazole, thiazole, isothiazole, oxazole, furazan, thiadiazole, pyridine, pyrazine, pyrimidine, pyridazine, or triazine. Of those, there is preferred a group produced by removing p+1 or q+1 hydrogen atoms from benzene, naphthalene, anthracene, pyridine, pyrazine, pyrimidine, pyridazine, or triazine.

In the general formula (1), the formula (b1), and the formula (d1), $L_1$ and $L_2$ each represent an aromatic hydrocarbon group having 6 to 22 carbon atoms, an aromatic heterocyclic group having 3 to 16 carbon atoms, or a group obtained by linking 2 to 10 of the groups, and such groups may each have a substituent.

$L_1$ and $L_2$ each represent preferably an aromatic hydrocarbon group having 6 to 22 carbon atoms, an aromatic heterocyclic group having 3 to 16 carbon atoms, or a group obtained by linking 2 to 10 of the groups, more preferably an aromatic hydrocarbon group having 6 to 18 carbon atoms, an aromatic heterocyclic group having 3 to 16 carbon atoms, or a group obtained by linking 2 to 7 of the groups.

Specific examples of $L_1$ and $L_2$ include groups each produced by removing one hydrogen atom from benzene, pentalene, indene, naphthalene, azulene, heptalene, octalene, indacene, acenaphthylene, phenalene, phenanthrene, anthracene, trindene, fluoranthene, acephenanthrylene, aceanthrylene, triphenylene, pyrene, chrysene, tetraphene, tetracene, pleiadene, picene, perylene, pentaphene, pentacene, tetraphenylene, cholanthrylene, helicene, hexaphene, rubicene, coronene, trinaphthylene, heptaphene, pyranthrene, furan, benzofuran, isobenzofuran, xanthene, oxanthrene, dibenzofuran, peri-xanthenoxanthene, thiophene, thioxanthene, thianthrene, phenoxathiin, thionaphthene, isothianaphthene, thiophthene, thiophanthrene, dibenzothiophene, pyrrole, pyrazole, tellurazole, selenazole, thiazole, isothiazole, oxazole, furazan, pyridine, pyrazine, pyrimidine, pyridazine, triazine, indolizine, indole, isoindole, indazole, purine, quinolizine, isoquinoline, carbazole, imidazole, naphthyridine, phthalazine, quinazoline, benzodiazepine, quinoxaline, cinnoline, quinoline, pteridine, phenanthridine, acridine, perimidine, phenanthroline, phenazine, carboline, phenotellurazine, phenoselenazine, phenothiazine, phenoxazine, anthyridine, benzothiazole, benzimidazole, benzoxazole, benzisoxazole, or benzisothiazole, or an aromatic compound obtained by linking a plurality of aromatic rings of these aromatic compounds.

Here, examples of the linking mode of a group obtained by linking the aromatic rings of a plurality of aromatic compounds represented by any one of $L_1$ and $L_2$ include the following modes.

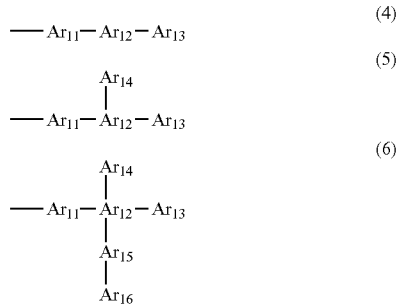

In the formulae (4) to (6), $Ar_{11}$ to $Ar_{16}$ each represent a substituted or unsubstituted aromatic ring. The aromatic ring means a ring of an aromatic hydrocarbon compound or of an aromatic heterocyclic compound, and can be a group that is monovalent or more. The phrase "linking aromatic rings" means that the aromatic rings are bonded by a direct bond to be linked. When the aromatic ring is a substituted aromatic ring, the substituent is not an aromatic ring.

Specific examples of the formulae (4) to (6) include groups each produced by removing a hydrogen atom from, for example, biphenyl, terphenyl, bipyridine, bipyrimidine, bitriazine, terpyridine, phenylterphenyl, binaphthalene, phenylpyridine, diphenylpyridine, phenylpyrimidine, diphenylpyrimidine, phenyltriazine, diphenyltriazine, phenylnaphthalene, diphenylnaphthalene, carbazolylbenzene, biscarbazolylbenzene, biscarbazolyltriazine, dibenzofuranylbenzene, bisdibenzofuranylbenzene, dibenzothiophenylbenzene, or bisdibenzothiophenylbenzene.

In the general formula (2), Z represents an aromatic hydrocarbon group having 6 to 22 carbon atoms, an aromatic heterocyclic group having 3 to 16 carbon atoms, or a divalent linking group obtained by linking 2 to 10 of the groups, but a group linked to N is an aromatic hydrocarbon group having 6 to 22 carbon atoms or a monocyclic aromatic heterocyclic group having 3 to 6 carbon atoms. Z preferably represents an aromatic hydrocarbon group having 6 to 18 carbon atoms, an aromatic heterocyclic group having 3 to 16 carbon atoms, or a divalent linking group obtained by linking 2 to 7 of the groups, the group linked to N is preferably an aromatic hydrocarbon group having 6 to 18 carbon atoms or a monocyclic aromatic heterocyclic group having 3 to 5 carbon atoms, and the monocyclic aromatic heterocyclic group is preferably a six-membered ring. The respective aromatic rings may each independently have a substituent.

Z specifically represents, for example, a divalent group produced by removing two hydrogen atoms from any one of the aromatic compounds listed in the specific examples of $L_1$ and $L_2$, or from an aromatic compound obtained by linking two or more of the compounds. However, the group linked to N is an aromatic hydrocarbon group having 6 to 22 carbon atoms or a monocyclic aromatic heterocyclic group having 3 to 6 carbon atoms.

Here, in the case where Z is constituted of a plurality of aromatic hydrocarbon groups or aromatic heterocyclic groups, examples of its linking mode include the following modes, and in this case, $Ar_{21}$ and $Ar_{23}$ each represent an aromatic hydrocarbon group having 6 to 22 carbon atoms or a monocyclic aromatic heterocyclic group having 3 to 6 carbon atoms. In addition, $Ar_{22}$ in the formula (7) $Ar_{22}$ or $Ar_{24}$ in the formula (8) or $Ar_{24}$, $Ar_{25}$, or $Ar_{26}$ in the formula (9) can have a linking hand instead of a group having a linking hand represented in each chemical formula, and in the case, the group having a linking hand is an aromatic hydrocarbon group having 6 to 22 carbon atoms or a monocyclic aromatic heterocyclic group having 3 to 6 carbon atoms.

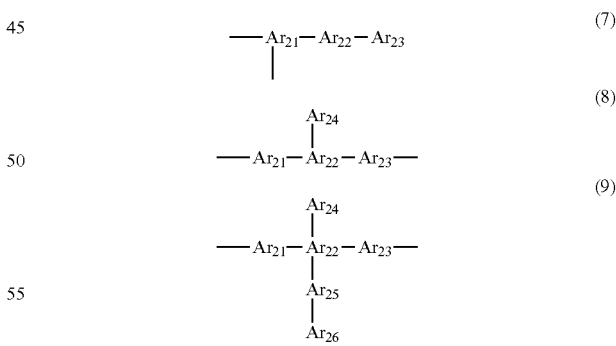

(In the formulae (7) to (9), $Ar_{21}$ to $Ar_{26}$ each represent a substituted or unsubstituted aromatic ring.)

In the general formula (1), the formula (b1), and the formula (d1), p and q each represent an integer of from 0 to 7, preferably from 0 to 5, more preferably from 0 to 3.

$Ar_1$ to $Ar_3$, Z, and $L_1$ and $L_2$ each represent any such aromatic hydrocarbon group or aromatic heterocyclic group as described above, or a group obtained by linking the groups, and such group can have a substituent. In this case, examples of the substituent include an alkyl group having 1 to 20 carbon atoms, an aralkyl group having 7 to 38 carbon atoms, an alkenyl group having 2 to 20 carbon atoms, an alkynyl group having 2 to 20 carbon atoms, a dialkylamino group having 2 to 40 carbon atoms, a diarylamino group having 12 to 44 carbon atoms, a diaralkylamino group having 14 to 76 carbon atoms, an acyl group having 2 to 20 carbon atoms, an acyloxy group having 2 to 20 carbon atoms, an alkoxy group having 1 to 20 carbon atoms, an alkoxycarbonyl group having 2 to 20 carbon atoms, an alkoxycarbonyloxy group having 2 to 20 carbon atoms, and an alkylsulfonyl group having 1 to 20 carbon atoms. Of those, an alkyl group having 1 to 10 carbon atoms, an aralkyl group having 7 to 24 carbon atoms, an alkoxy group having 1 to 10 carbon atoms, or a diarylamino group having 12 to 36 carbon atoms is preferred. It should be noted that the number of substituents is from 0 to 5, preferably from 0 to 2.

Specific examples of the substituent include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, phenylmethyl, phenylethyl, phenylicosyl, naphthylmethyl, anthranylmethyl, phenanthrenylmethyl, pyrenylmethyl, vinyl, propenyl, butenyl, pentenyl, decenyl, icosenyl, ethynyl, propargyl, butynyl, pentynyl, decynyl, icosynyl, dimethylamino, ethylmethylamino, diethylamino, dipropylamino, dibutylamino, dipentynylamino, didecylamino, diicosylamino, diphenylamino, naphthylphenylamino, dinaphthylamino, dianthranylamino, diphenanthrenylamino, dipyrenylamino, diphenylmethylamino, diphenylethylamino, phenylmethylphenylethylamino, dinaphthylmethylamino, dianthranylmethylamino, diphenanthrenylmethylamino, acetyl, propionyl, butyryl, valeryl, benzoyl, acetyloxy, propionyloxy, butyryloxy, valeryloxy, benzoyloxy, methoxy, ethoxy, propoxy, butoxy, pentoxy, hexoxy, heptoxy, octoxy, nonyloxy, decoxy, undecyloxy, dodecoxy, tridecoxy, tetradecoxy, pentadecoxy, hexadecoxy, heptadecoxy, octadecoxy, nonadecoxy, icosoxy, methoxycarbonyl, ethoxycarbonyl, propoxycarbonyl, butoxycarbonyl, pentoxycarbonyl, methoxycarbonyloxy, ethoxycarbonyloxy, propoxycarbonyloxy, butoxycarbonyloxy, pentoxycarbonyloxy, methylsulfonyl, ethylsulfonyl, propylsulfonyl, butylsulfonyl, and pentylsulfonyl. Of those, there is preferred a C1-12 alkyl group such as methyl, ethyl, propyl, butyl, pentyl, hexyl, heptyl, octyl, nonyl, or decyl, a C7-20 aralkyl group such as phenylmethyl, phenylethyl, naphthylmethyl, anthranylmethyl, phenanthrenylmethyl, or pyrenylmethyl, a C1-10 alkoxy group such as methoxy, ethoxy, propoxy, butoxy, pentoxy, hexoxy, heptoxy, octoxy, nonyloxy, or decoxy, or a diarylamino group having two C6-15 aromatic hydrocarbon groups such as diphenylamino, naphthylphenylamino, dinaphthylamino, dianthranylamino, or diphenanthrenylamino.

In the general formula (1), the formula (a1), the general formula (2), and the formula (c1), R, R', and $R_1$ to $R_8$ each independently represent hydrogen, an alkyl group having 1 to 20 carbon atoms, an aralkyl group having 7 to 38 carbon atoms, an alkenyl group having 2 to 20 carbon atoms, an alkynyl group having 2 to 20 carbon atoms, a dialkylamino group having 2 to 40 carbon atoms, a diarylamino group having 12 to 44 carbon atoms, a diaralkylamino group having 14 to 76 carbon atoms, an acyl group having 2 to 20 carbon atoms, an acyloxy group having 2 to 20 carbon atoms, an alkoxy group having 1 to 20 carbon atoms, an alkoxycarbonyl group having 2 to 20 carbon atoms, an alkoxycarbonyloxy group having 2 to 20 carbon atoms, an alkylsulfonyl group having 1 to 20 carbon atoms, an aromatic hydrocarbon group having 6 to 22 carbon atoms, or an aromatic heterocyclic group having 3 to 16 carbon atoms. Of those, hydrogen, an alkyl group having 1 to 10 carbon atoms, an aralkyl group having 7 to 24 carbon atoms, an alkoxy group having 1 to 10 carbon atoms, a diarylamino group having 12 to 36 carbon atoms, an aromatic hydrocarbon group having 6 to 18 carbon atoms, or an aromatic heterocyclic group having 3 to 16 carbon atoms is preferred, and hydrogen, an aromatic hydrocarbon group having 6 to 18 carbon atoms, or an aromatic heterocyclic group having 3 to 16 carbon atoms is more preferred. It should be noted that when R, R', and $R_1$ to $R_8$ each represent a group except hydrogen, each of the groups may have a substituent.

Specific examples of the alkyl group having 1 to 20 carbon atoms, the aralkyl group having 7 to 38 carbon atoms, the alkenyl group having 2 to 20 carbon atoms, the alkynyl group having 2 to 20 carbon atoms, the dialkylamino group having 2 to 40 carbon atoms, the diarylamino group having 12 to 44 carbon atoms, the diaralkylamino group having 14 to 76 carbon atoms, the acyl group having 2 to 20 carbon atoms, the acyloxy group having 2 to 20 carbon atoms, the alkoxy group having 1 to 20 carbon atoms, the alkoxycarbonyl group having 2 to 20 carbon atoms, the alkoxycarbonyloxy group having 2 to 20 carbon atoms, and the alkylsulfonyl group having 1 to 20 carbon atoms include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, phenylmethyl, phenylethyl, phenylicosyl, naphthylmethyl, anthranylmethyl, phenanthrenylmethyl, pyrenylmethyl, vinyl, propenyl, butenyl, pentenyl, decenyl, icosenyl, ethynyl, propargyl, butynyl, pentynyl, decynyl, icosynyl, dimethylamino, ethylmethylamino, diethylamino, dipropylamino, dibutylamino, dipentynylamino, didecylamino, diicosylamino, diphenylamino, naphthylphenylamino, dinaphthylamino, dianthranylamino, diphenanthrenylamino, dipyrenylamino, diphenylmethylamino, diphenylethylamino, phenylmethylphenylethylamino, dinaphthylmethylamino, dianthranylmethylamino, diphenanthrenylmethylamino, acetyl, propionyl, butyryl, valeryl, benzoyl, acetyloxy, propionyloxy, butyryloxy, valeryloxy, benzoyloxy, methoxy, ethoxy, propoxy, butoxy, pentoxy, hexoxy, heptoxy, octoxy, nonyloxy, decoxy, undecyloxy, dodecoxy, tridecoxy, tetradecoxy, pentadecoxy, hexadecoxy, heptadecoxy, octadecoxy, nonadecoxy, icosoxy, methoxycarbonyl, ethoxycarbonyl, propoxycarbonyl, butoxycarbonyl, pentoxycarbonyl, methoxycarbonyloxy, ethoxycarbonyloxy, propoxycarbonyloxy, butoxycarbonyloxy, pentoxycarbonyloxy, methylsulfonyl, ethylsulfonyl, propylsulfonyl, butylsulfonyl, and pentylsulfonyl. Of those, there is preferred an alkyl group having 1 to 10 carbon atoms such as methyl, ethyl, propyl, butyl, pentyl, hexyl, heptyl, octyl, nonyl, or decyl, an aralkyl group having 7 to 17 carbon atoms such as phenylmethyl, phenylethyl, naphthylmethyl, anthranylmethyl, phenanthrenylmethyl, or pyrenylmethyl, an alkoxy group having 1 to 10 carbon atoms such as methoxy, ethoxy, propoxy, butoxy, pentoxy, hexoxy, heptoxy, octoxy, nonyloxy, or decoxy, or a diarylamino group having 12 to 28 carbon atoms such as diphenylamino, naphthylphenylamino, dinaphthylamino, dianthranylamino, or diphenanthrenylamino.

In the case of the aromatic hydrocarbon group having 6 to 22 carbon atoms or the aromatic heterocyclic group having 3 to 16 carbon atoms, a specific example thereof is a group produced by removing a hydrogen atom from benzene, pentalene, indene, naphthalene, azulene, indacene, acenaphthylene, phenalene, phenanthrene, anthracene, trindene, fluoranthene, acephenanthrylene, aceanthrylene, triphenylene, pyrene, chrysene, tetraphene, tetracene, pleiadene, picene, perylene, pentaphene, pentacene, tetraphenylene, cholanthrylene, furan, benzofuran, isobenzofuran, xanthene, oxanthrene, dibenzofuran, peri-xanthenoxanthene, thiophene, thioxanthene, thianthrene, phenoxathiin, thionaphthene, isothianaphthene, thiophthene, thiophanthrene, dibenzothiophene, pyrrole, pyrazole, tellurazole, selenazole, thiazole, isothiazole, oxazole, furazan, thiadiazole, pyridine, pyrazine, pyrimidine, pyridazine, triazine, indolizine, indole, isoindole, indazole, purine, quinolizine, isoquinoline, carbazole, imidazole, naphthyridine, phthalazine, quinazoline, benzodiazepine, quinoxaline, cinnoline, quinoline, pteridine, phenanthridine, acridine, perimidine, phenanthroline, phenazine, carboline, phenotellurazine, phenoselenazine, phenothiazine, phenoxazine, anthyridine, benzothiazole, benzimidazole, benzoxazole, benzisoxazole, or benzisothiazole. Of those, there is preferred a group produced by removing a hydrogen atom from benzene, naphthalene, anthracene, pyridine, pyrazine, pyrimidine, pyridazine, triazine, isoindole, indazole, purine, isoquinoline, imidazole, naphthyridine, phthalazine, quinazoline, benzodiazepine, quinoxaline, cinnoline, quinoline, pteridine, phenanthridine, acridine, perimidine, phenanthroline, phenazine, carboline, indole, carbazole, dibenzofuran, or dibenzothiophene.

In the general formula (1), the formula (a1), the general formula (2), and the formula (c1), when any one of R, R', and $R_1$ to $R_8$ represents a group except hydrogen and the group has a substituent, the substituent is an alkyl group having 1 to 20 carbon atoms, an aralkyl group having 7 to 38 carbon atoms, an alkenyl group having 2 to 20 carbon atoms, an alkynyl group having 2 to 20 carbon atoms, a dialkylamino group having 2 to 40 carbon atoms, a diarylamino group having 12 to 44 carbon atoms, a diaralkylamino group having 14 to 76 carbon atoms, an acyl group having 2 to 20 carbon atoms, an acyloxy group having 2 to 20 carbon atoms, an alkoxy group having 1 to 20 carbon atoms, an alkoxycarbonyl group having 2 to 20 carbon atoms, an alkoxycarbonyloxy group having 2 to 20 carbon atoms, an alkylsulfonyl group having 1 to 20 carbon atoms, an aromatic hydrocarbon group having 6 to 22 carbon atoms, or an aromatic heterocyclic group having 3 to 16 carbon atoms. Of those, an alkyl group having 1 to 10 carbon atoms, an aralkyl group having 7 to 24 carbon atoms, an alkoxy group having 1 to 10 carbon atoms, a diarylamino group having 12 to 36 carbon atoms, an aromatic hydrocarbon group having 6 to 18 carbon atoms, or an aromatic heterocyclic group having 3 to 16 carbon atoms is preferred, and an aromatic hydrocarbon group having 6 to 18 carbon atoms and an aromatic heterocyclic group having 3 to 16 carbon atoms are more preferred. It should be noted that the number of substituents is preferably from 0 to 3, more preferably from 0 to 2 per one of R, R', and $R_1$ to $R_8$.

Specific examples of the alkyl group having 1 to 20 carbon atoms, the aralkyl group having 7 to 38 carbon atoms, the alkenyl group having 2 to 20 carbon atoms, the alkynyl group having 2 to 20 carbon atoms, the dialkylamino group having 2 to 40 carbon atoms, the diarylamino group having 12 to 44 carbon atoms, the diaralkylamino group having 14 to 76 carbon atoms, the acyl group having 2 to 20 carbon atoms, the acyloxy group having 2 to 20 carbon atoms, the alkoxy group having 1 to 20 carbon atoms, the alkoxycarbonyl group having 2 to 20 carbon atoms, the alkoxycarbonyloxy group having 2 to 20 carbon atoms, the alkylsulfonyl group having 1 to 20 carbon atoms, the aromatic hydrocarbon group having 6 to 22 carbon atoms, and the aromatic heterocyclic group having 3 to 16 carbon atoms are the same as the specific examples of R, R', and $R_1$ to $R_8$.

Preferred specific examples of the compounds represented by the general formulae (1) and (2) are shown below, but compounds are not limited thereto.

1-1

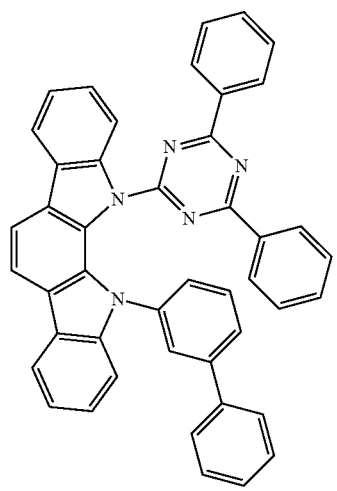

1-2

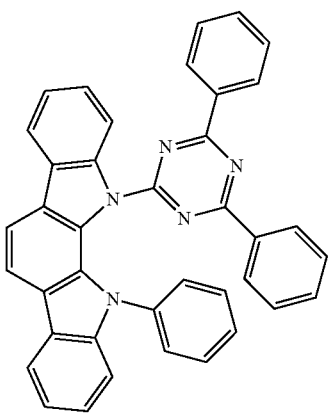

-continued
1-3
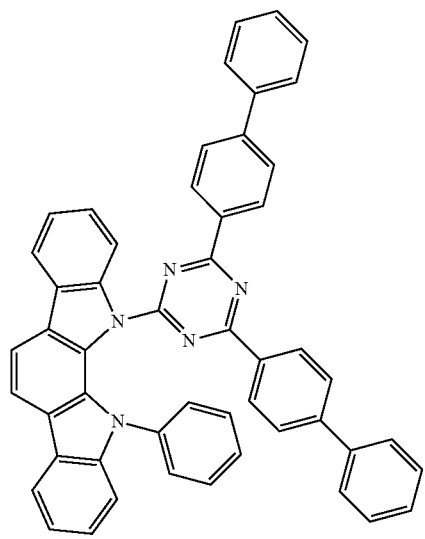
1-4
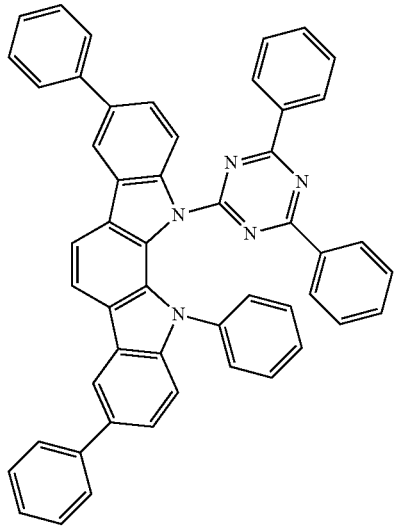
1-5
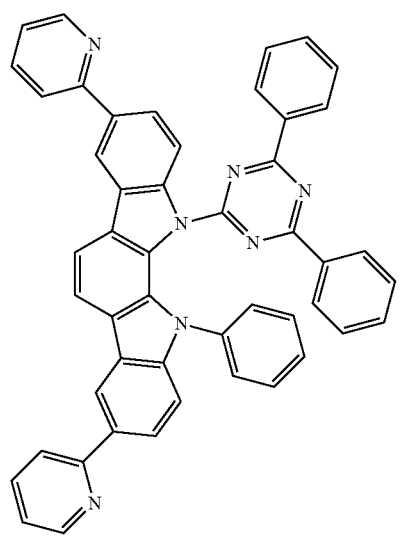
1-6
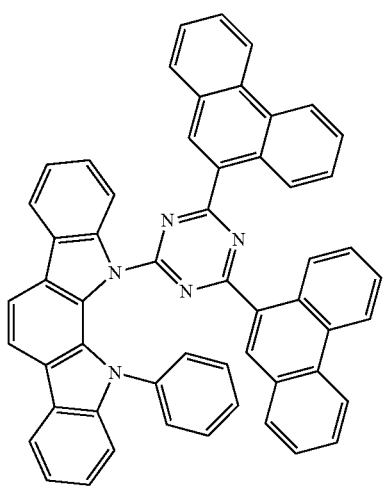
1-7
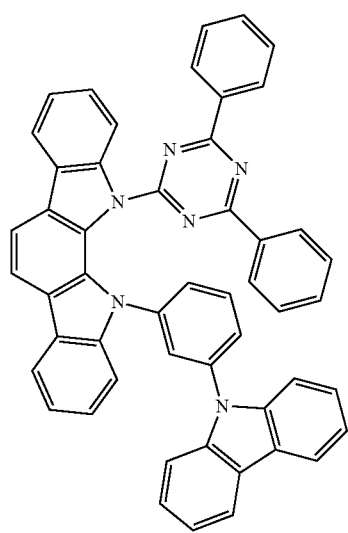
1-8
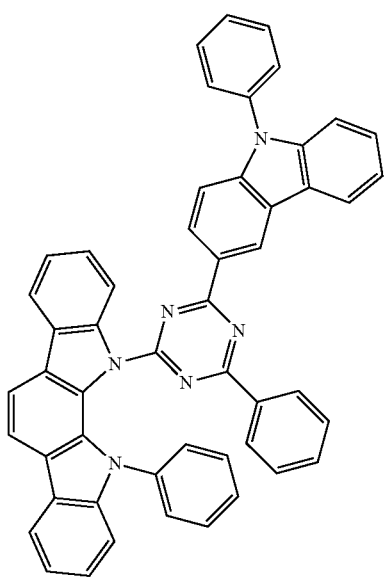

-continued
1-9
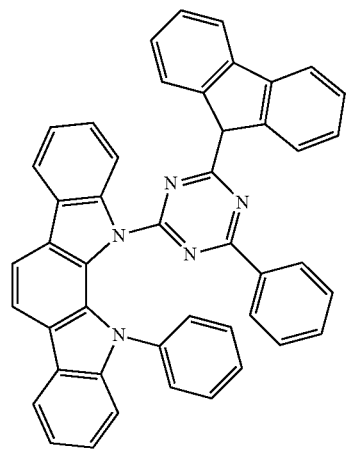
1-10
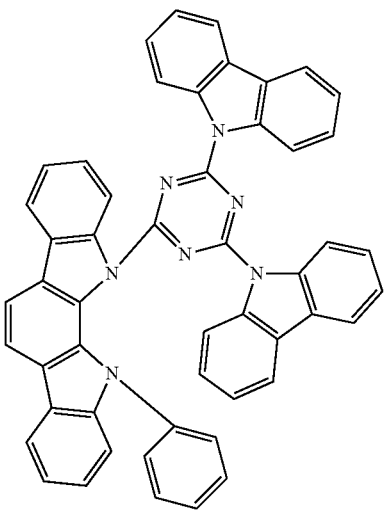
1-11
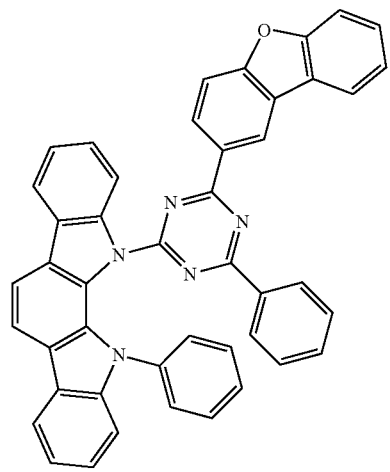
1-12
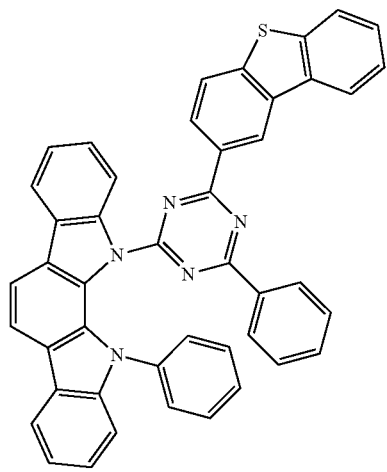
1-13
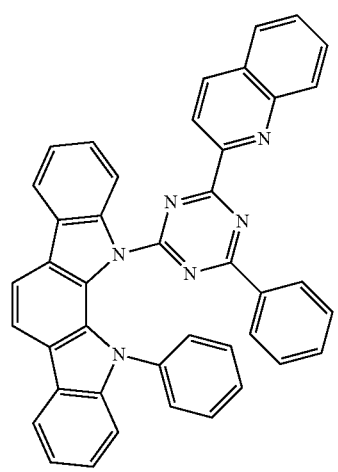
1-14
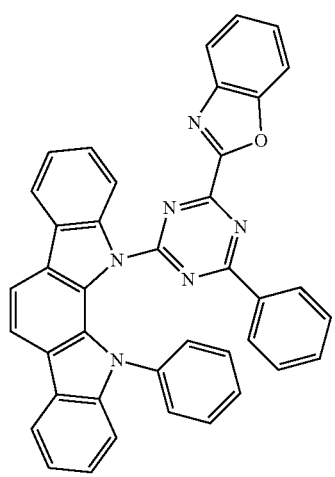

-continued
| 1-15 | 1-16 |
|---|---|
| 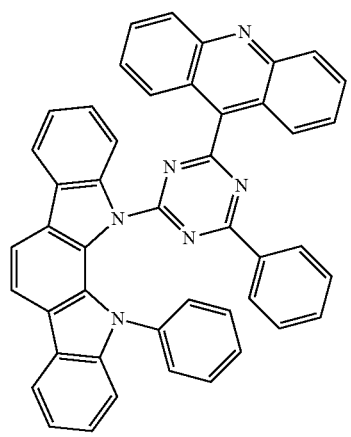 | 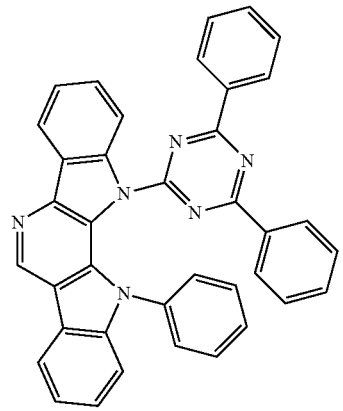 |
| 1-17 | 1-18 |
| 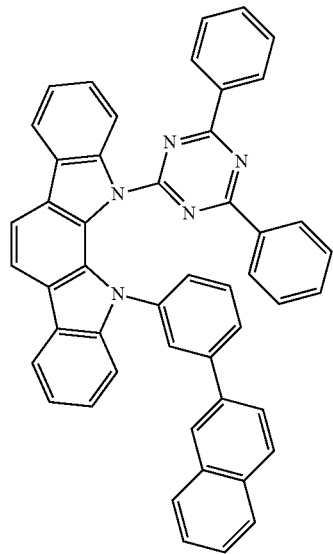 | 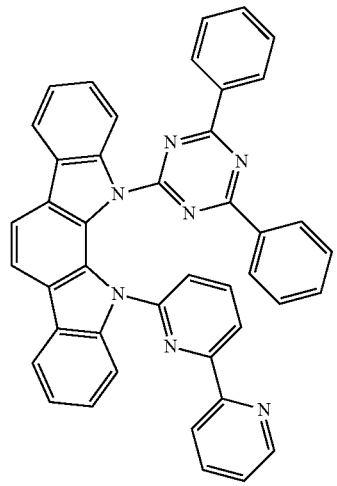 |
| 1-19 | 1-20 |
| 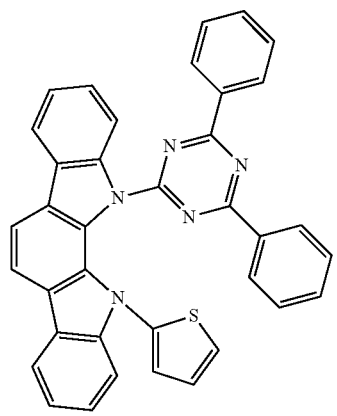 | 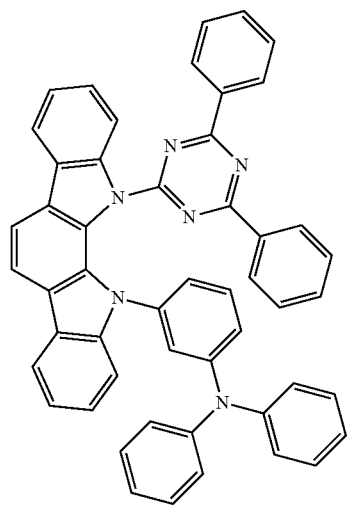 |

-continued
1-21
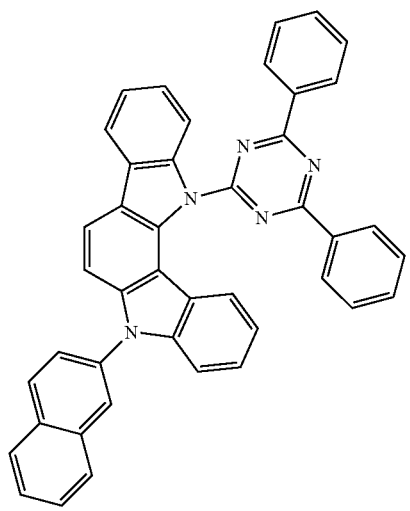
1-22
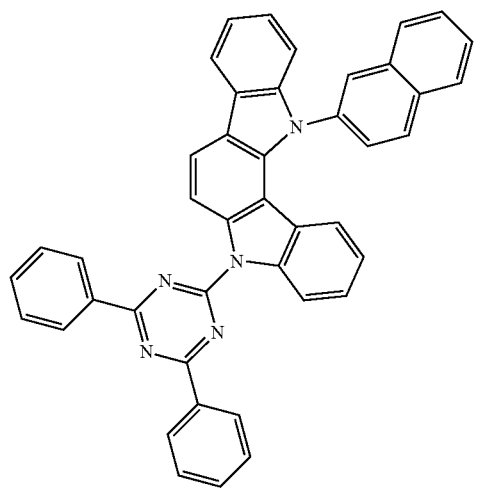
1-23
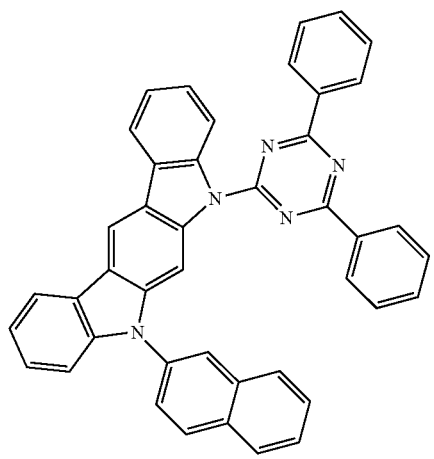
1-24
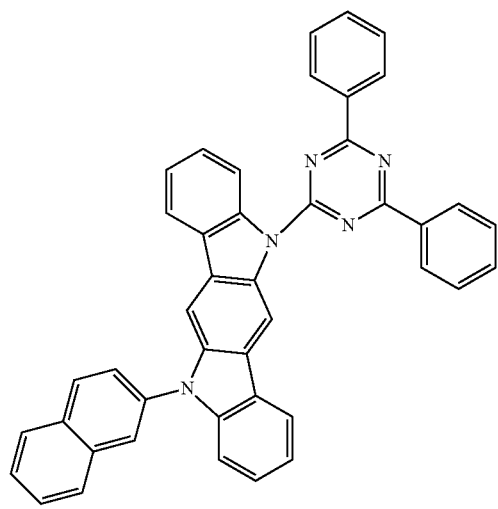
1-25
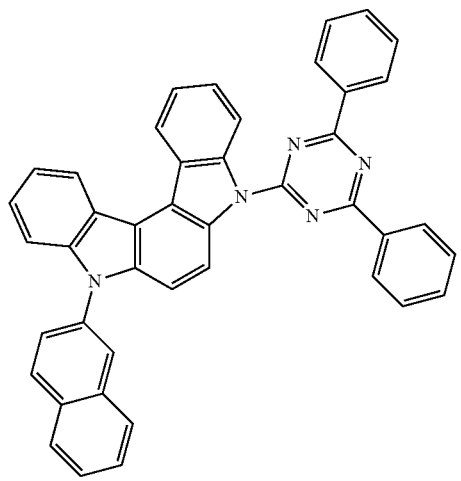
1-26
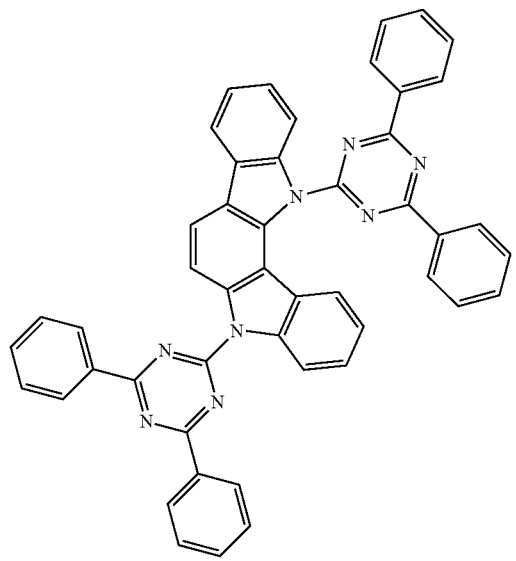

-continued
1-27
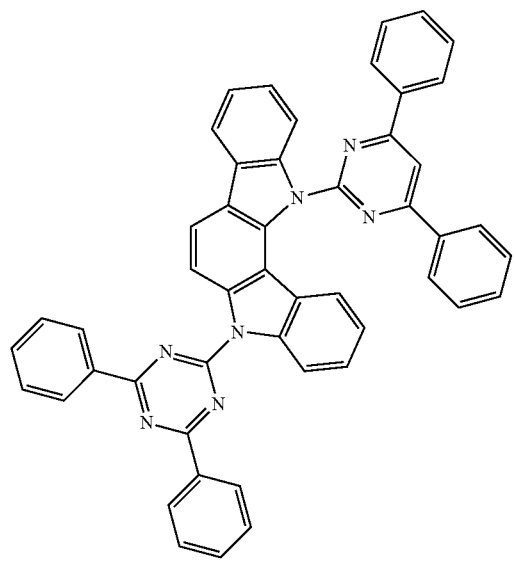
1-28
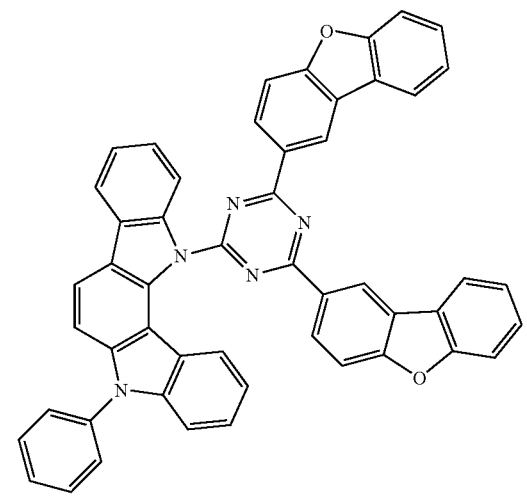
1-29
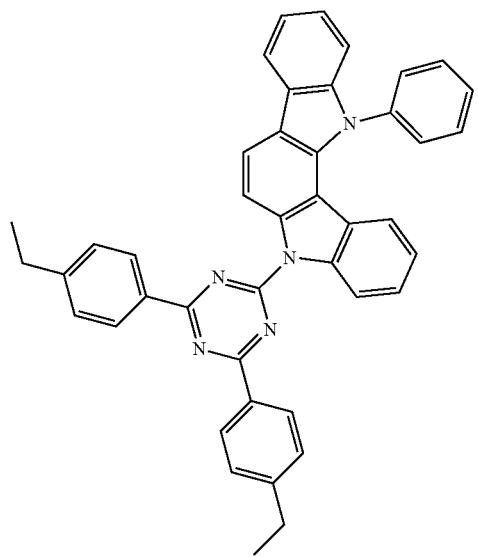
1-30
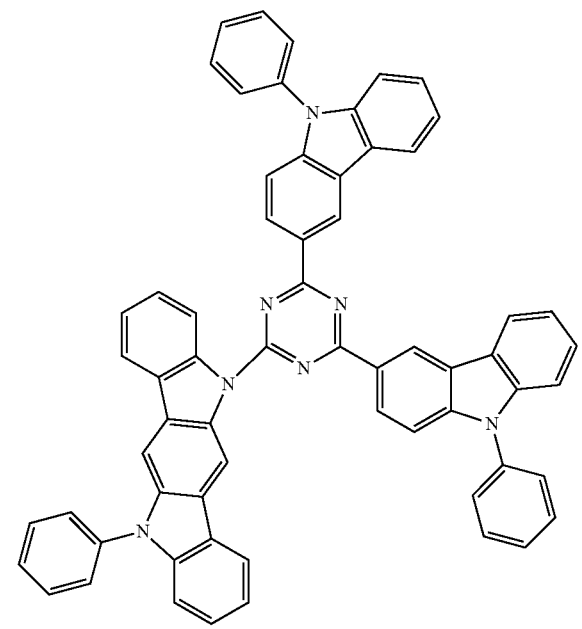

-continued
1-31
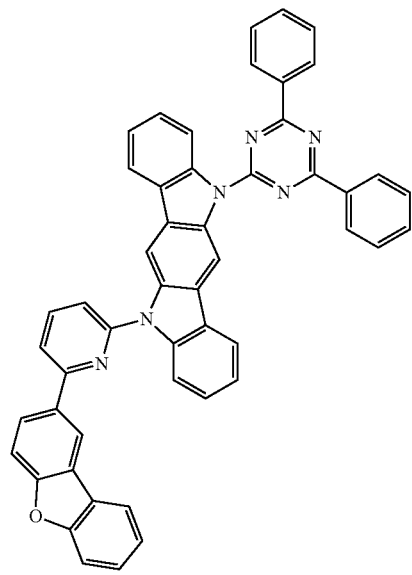
1-32
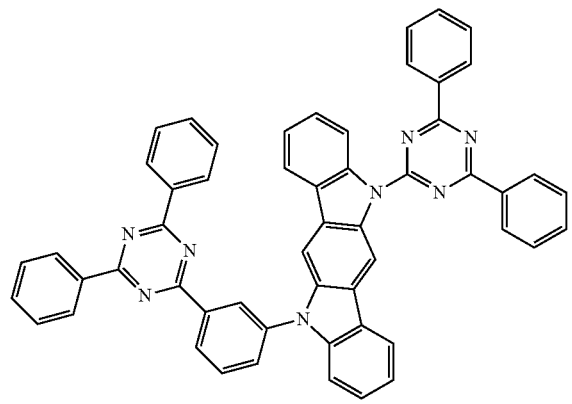
1-33
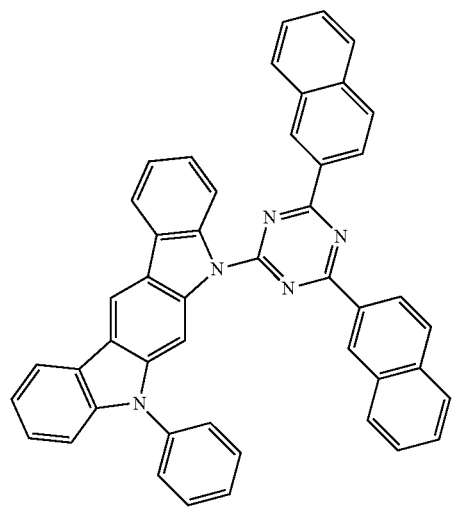
1-34
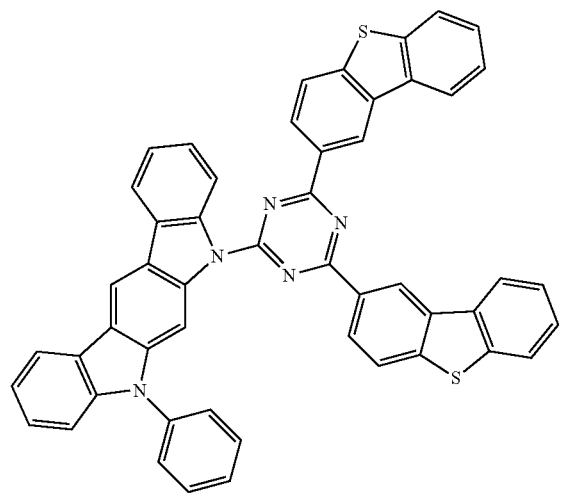
1-35
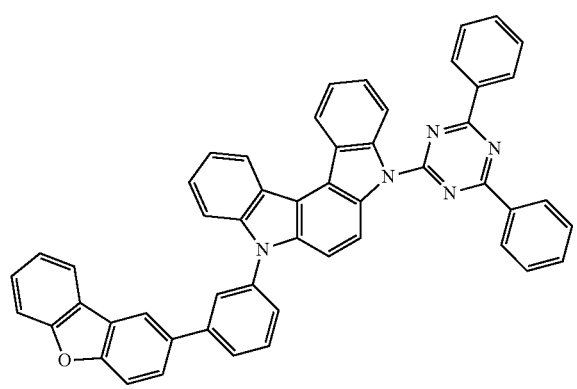
1-36
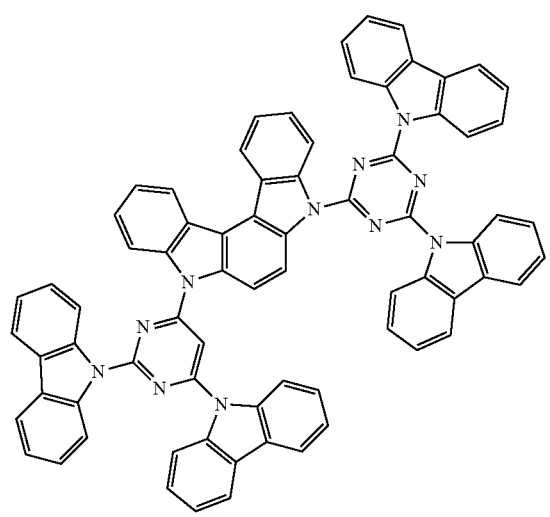

-continued
1-37
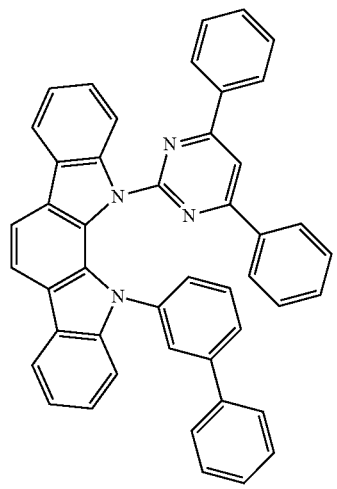
1-38
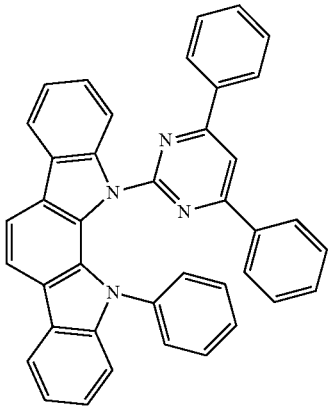
1-39
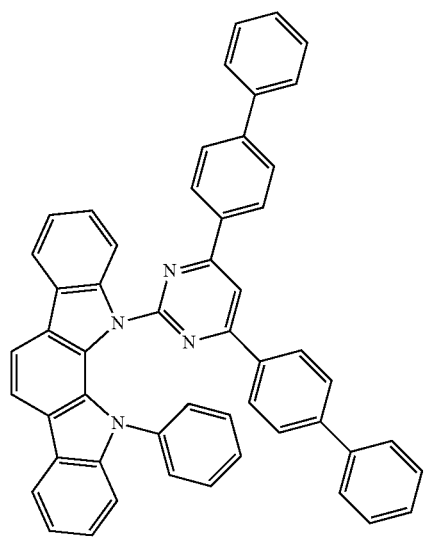
1-40
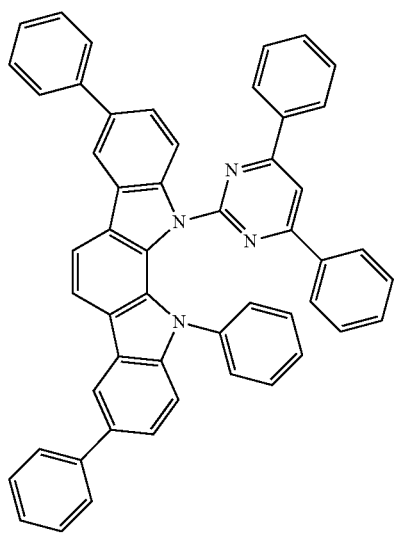
1-41
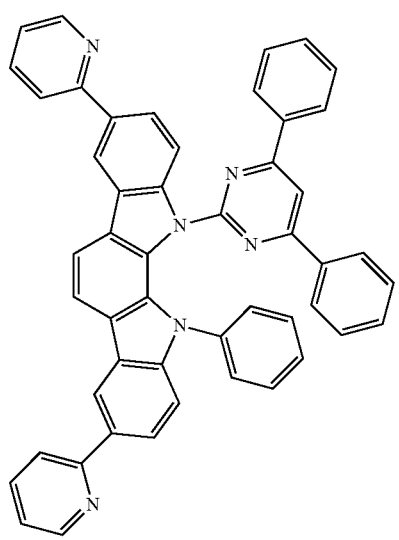
1-42
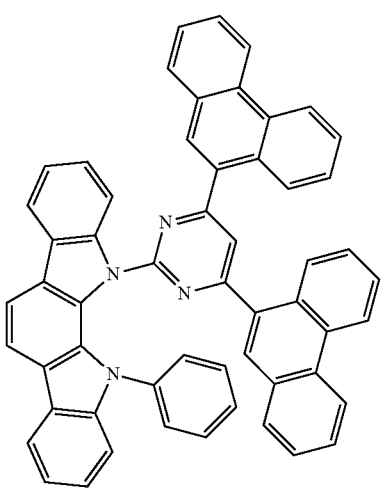

-continued
1-43
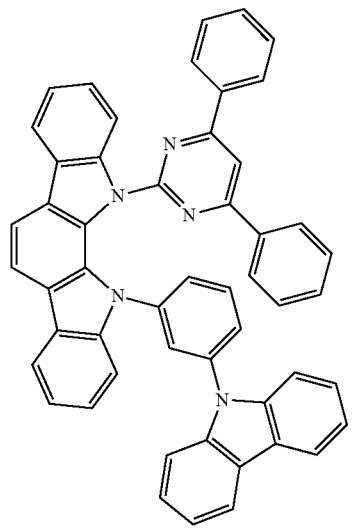
1-44
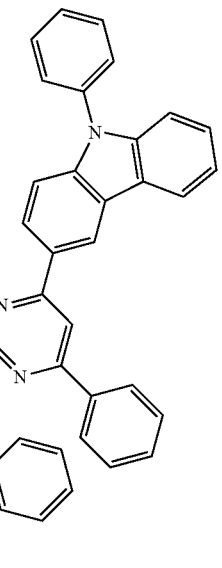
1-45
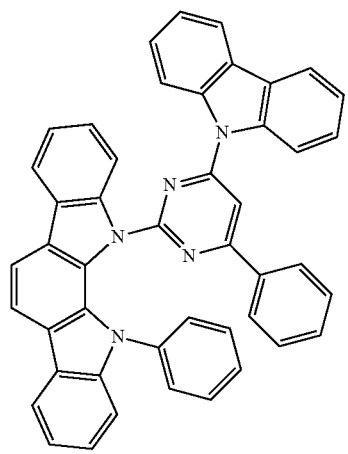
1-46
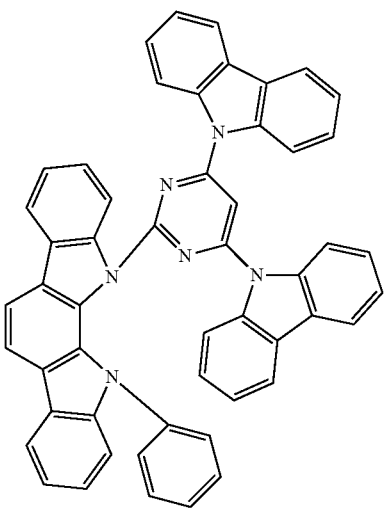
1-47
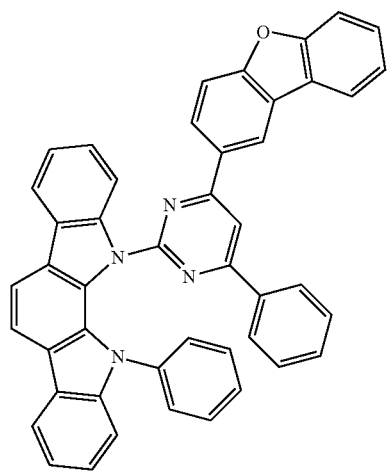
1-48
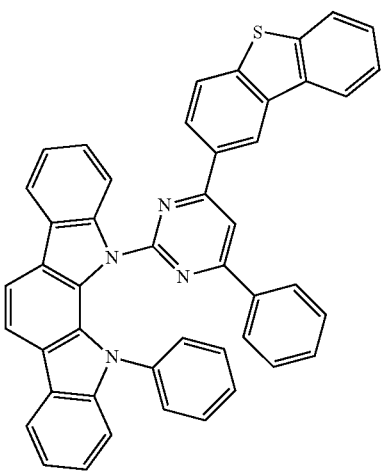

-continued
1-49
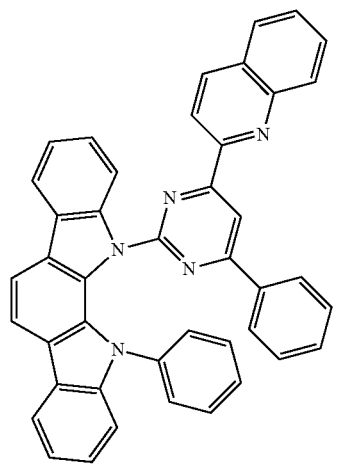
1-50
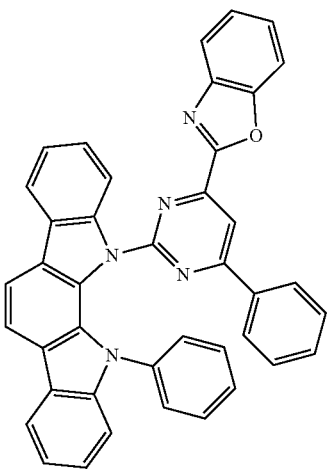
1-51
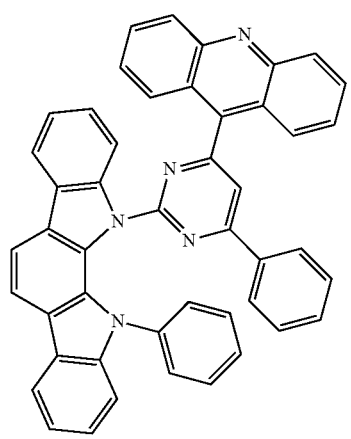
1-52
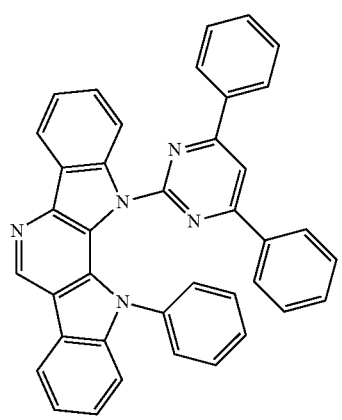
1-53
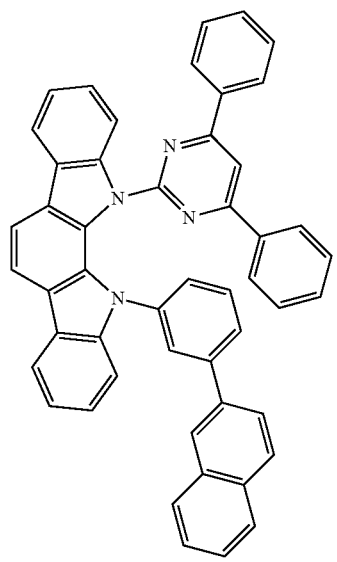
1-54
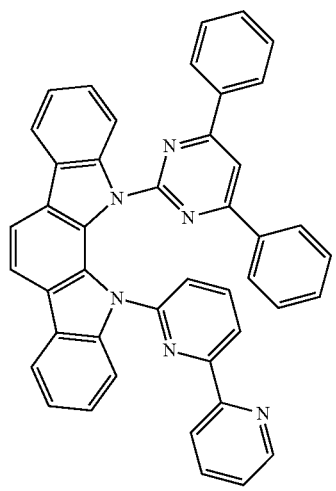

-continued
1-55
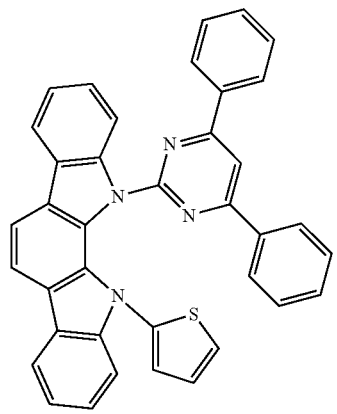
1-56
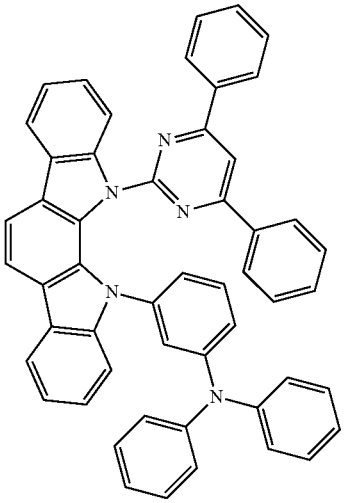
1-57
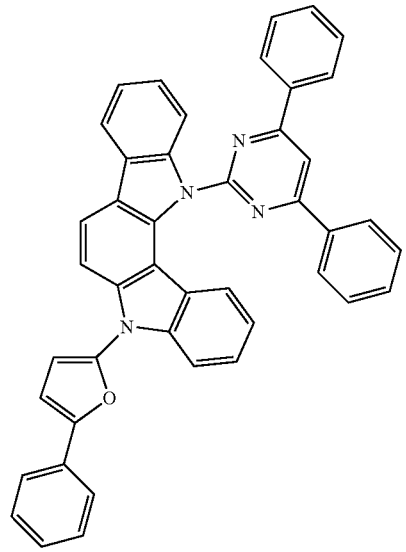
1-58
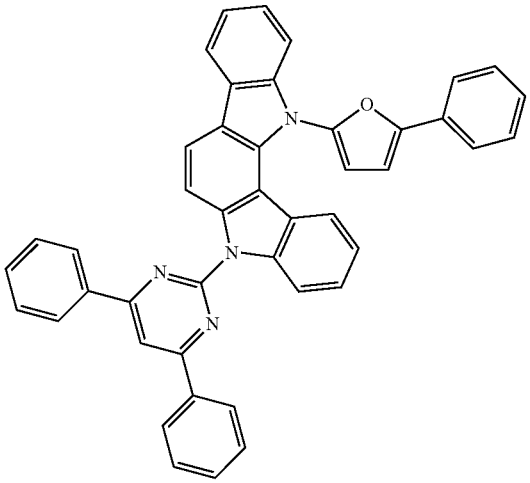
1-59
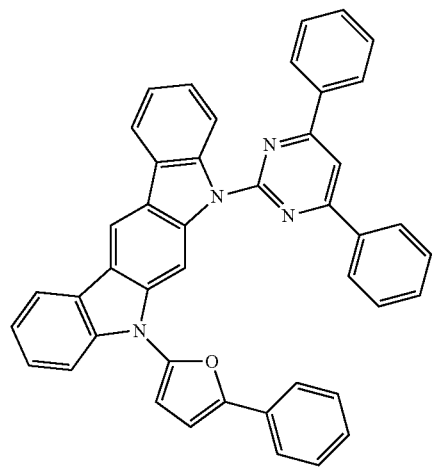
1-60
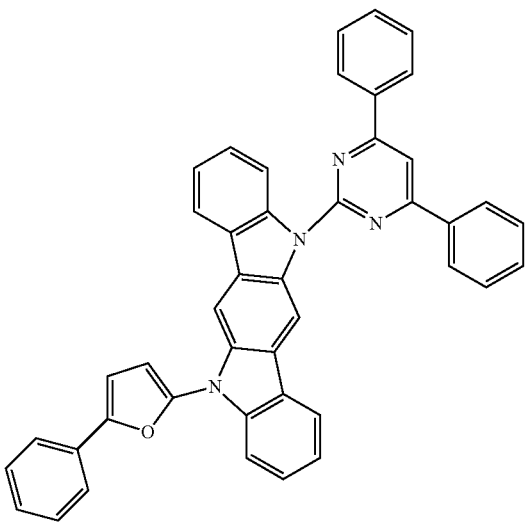

-continued
1-61
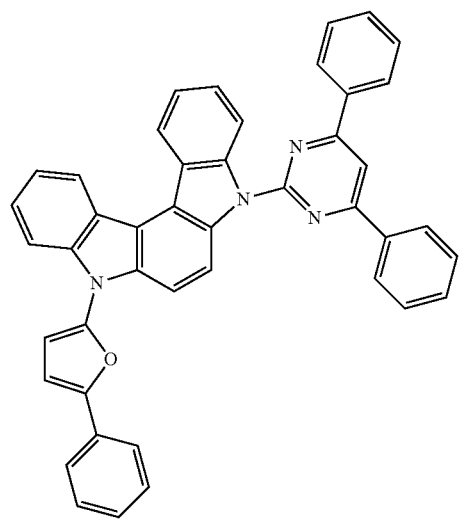
1-62
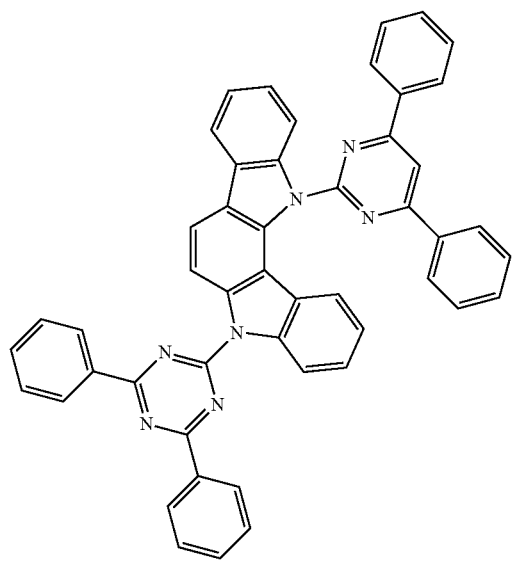
1-63
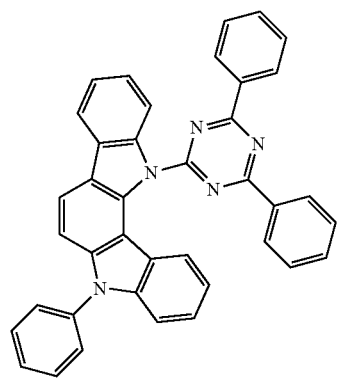
1-64
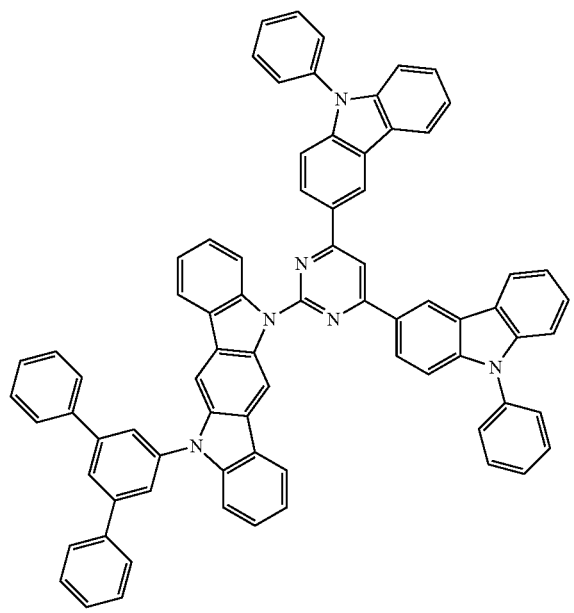

1-65
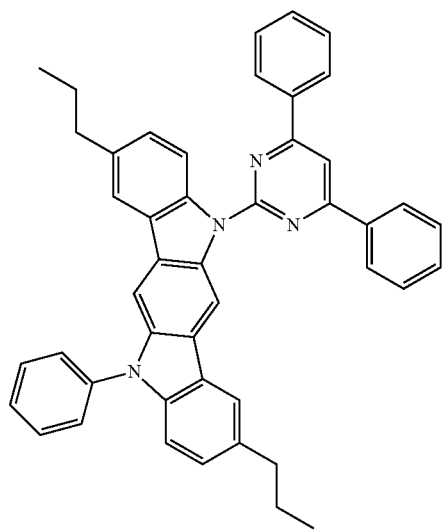
1-66
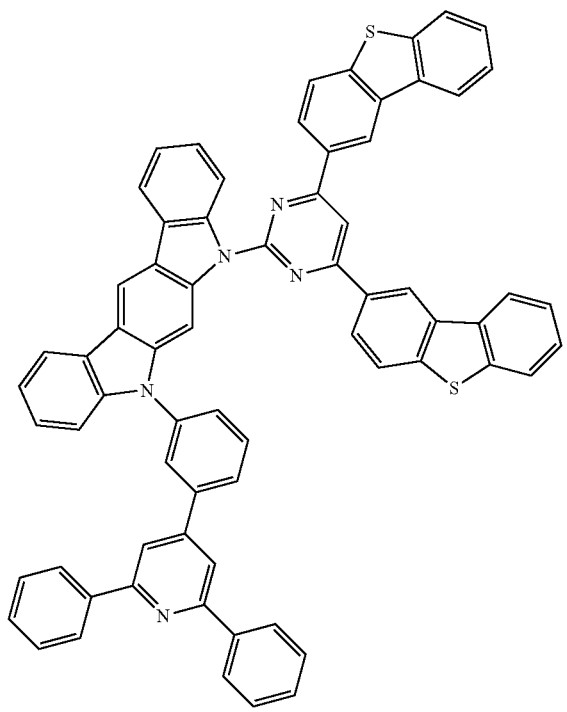
1-67
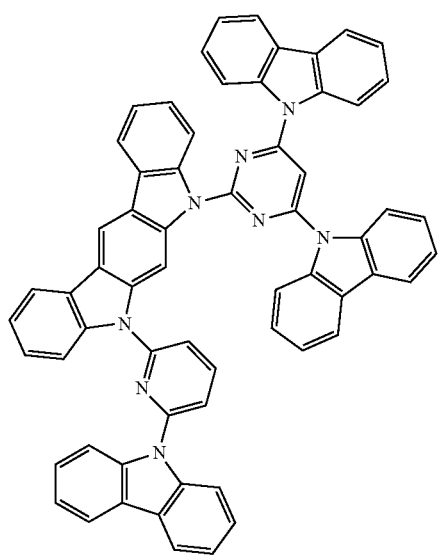
1-68
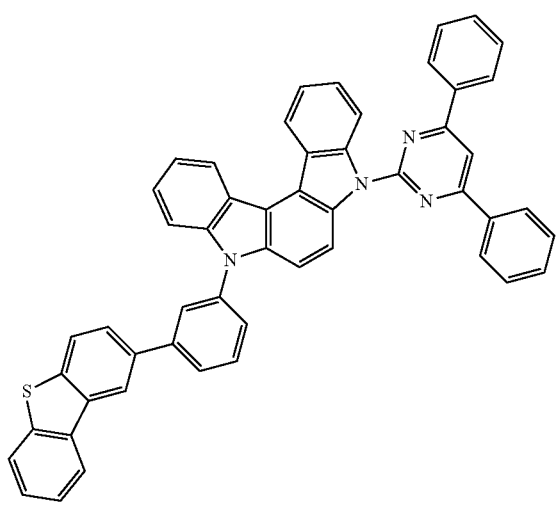

-continued
1-69
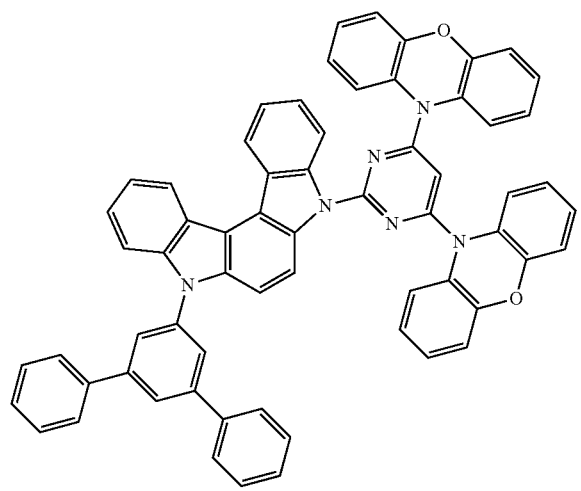
1-70
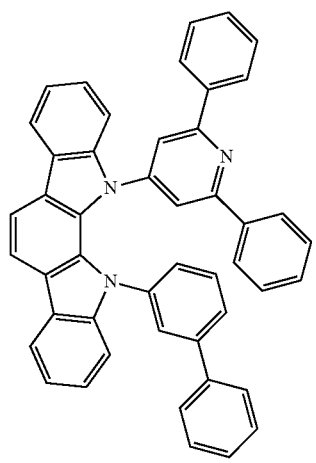
1-71
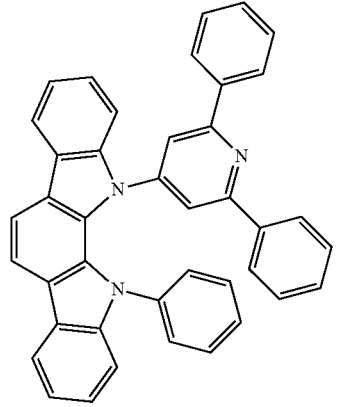
1-72
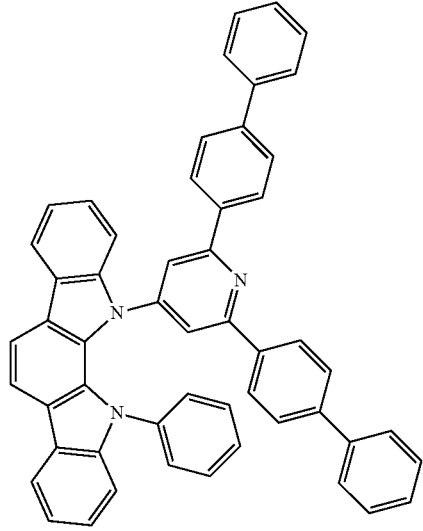
1-173
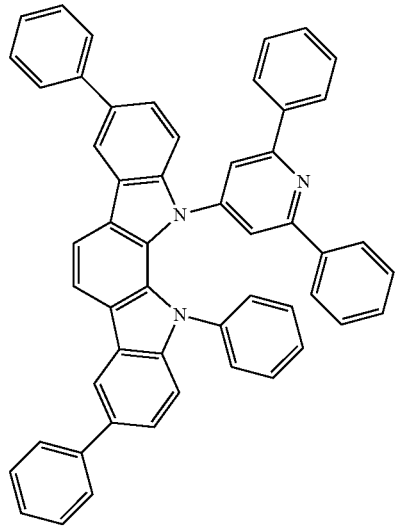
1-74
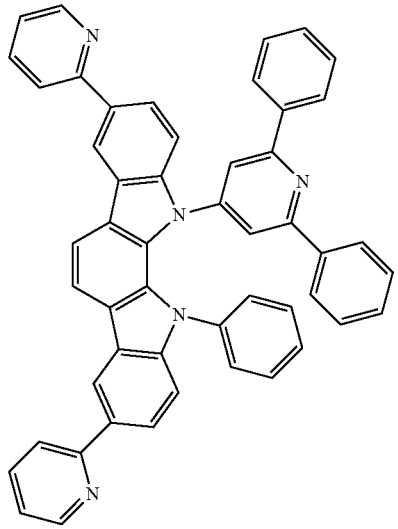

-continued
1-75
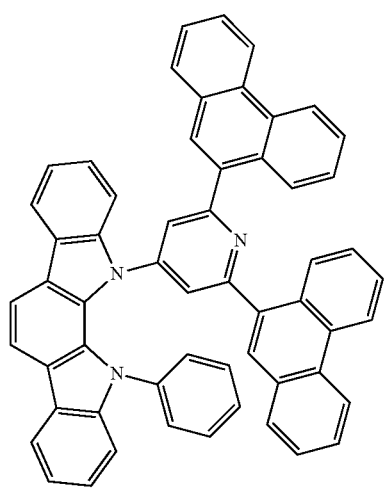
1-76
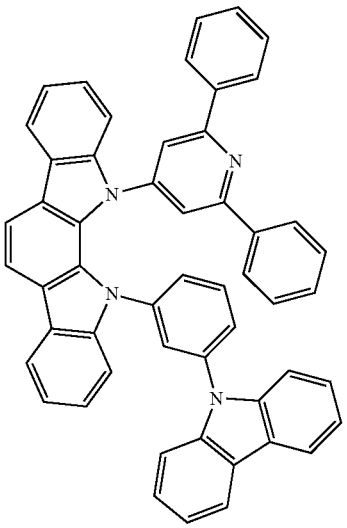
1-77
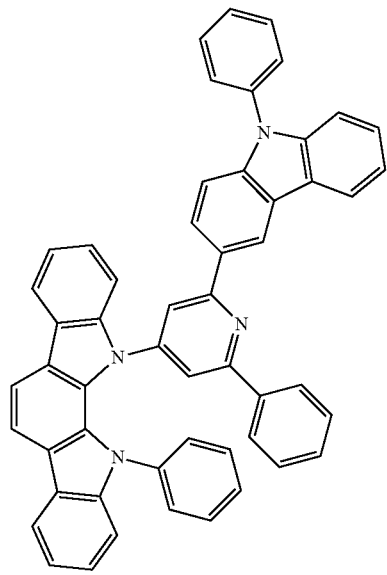
1-78
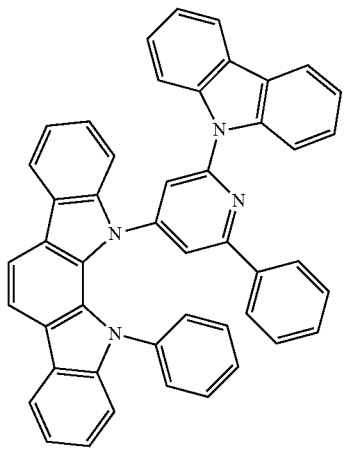
1-79
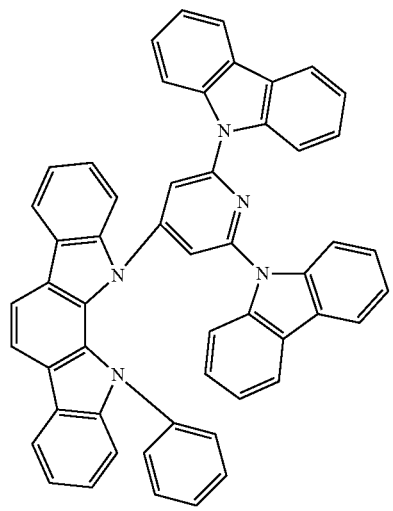
1-80
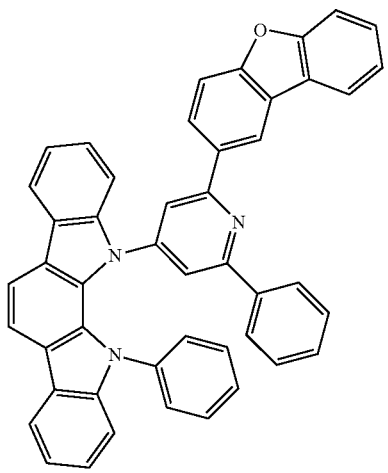

-continued
1-81
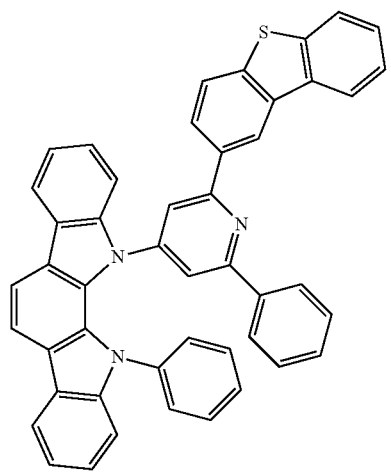
1-82
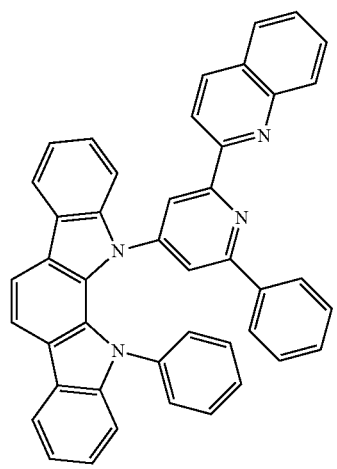
1-83
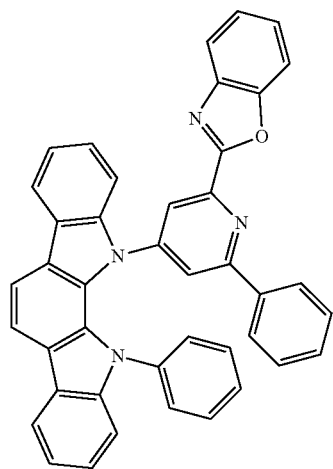
1-84
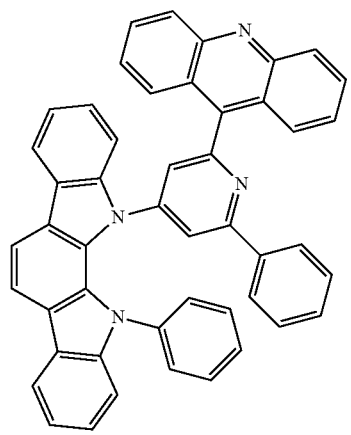
1-85
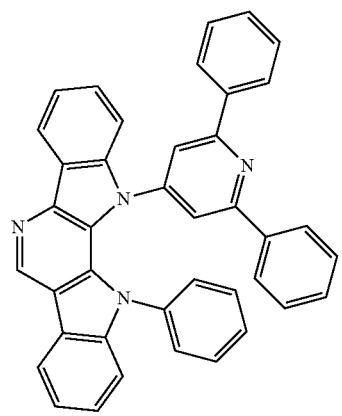
1-86
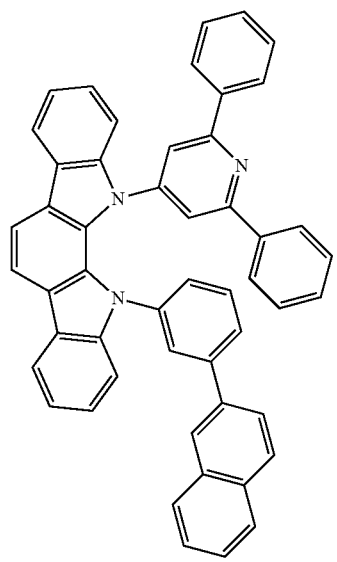

-continued
1-87
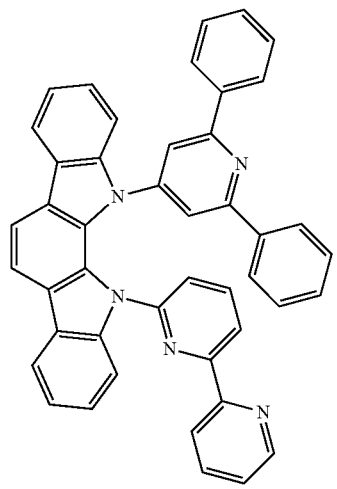
1-88
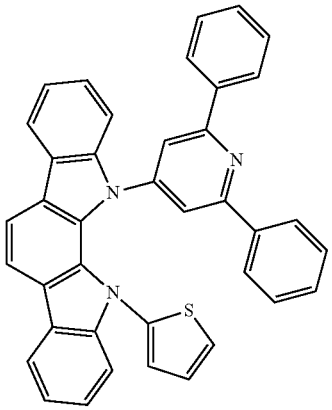
1-89
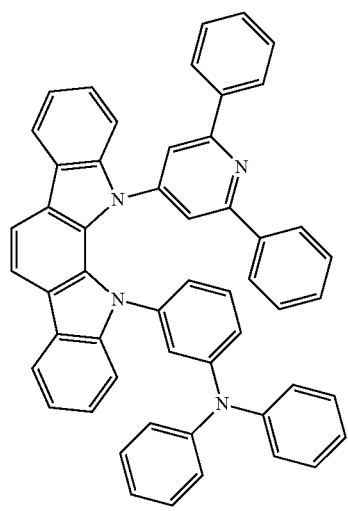
1-90
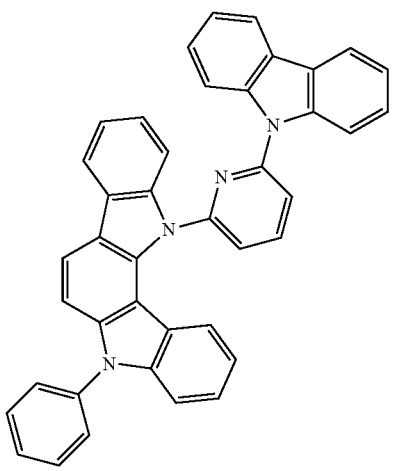
1-91
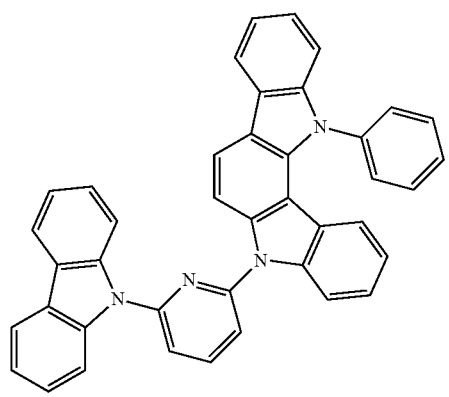
1-92
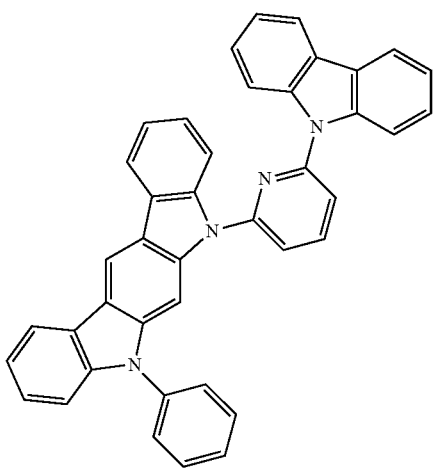

-continued
1-93
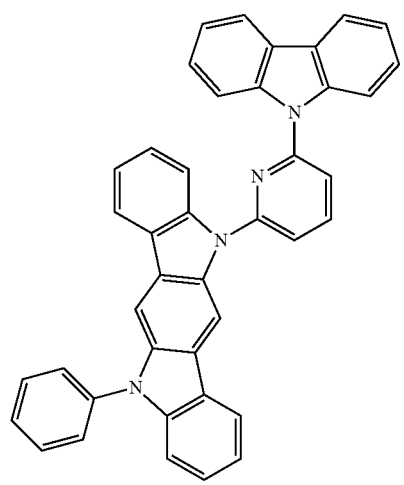
1-94
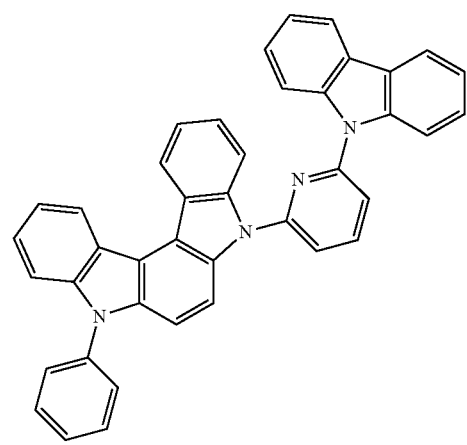
1-95
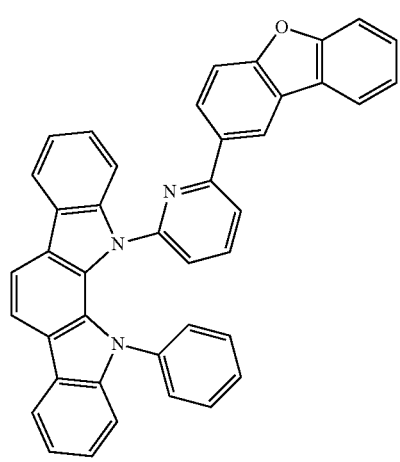
1-96
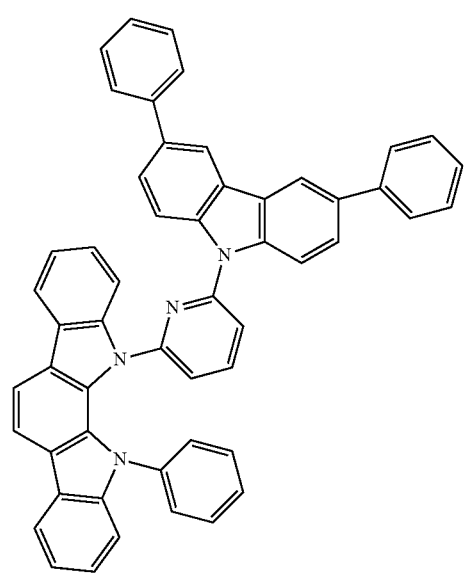
1-97
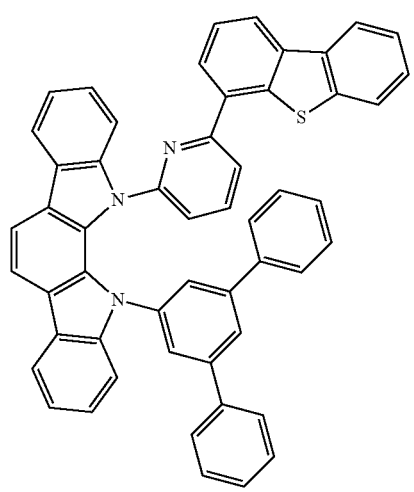
1-98
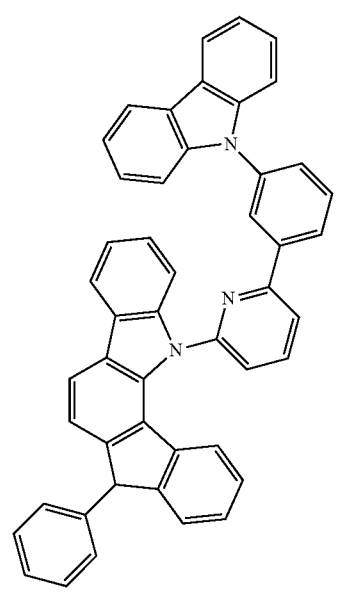

1-99
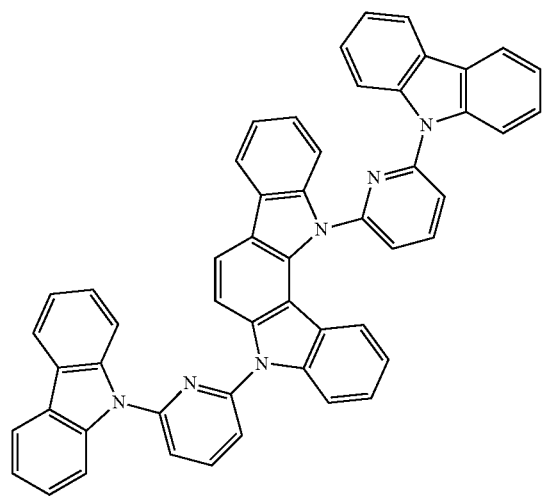
1-100
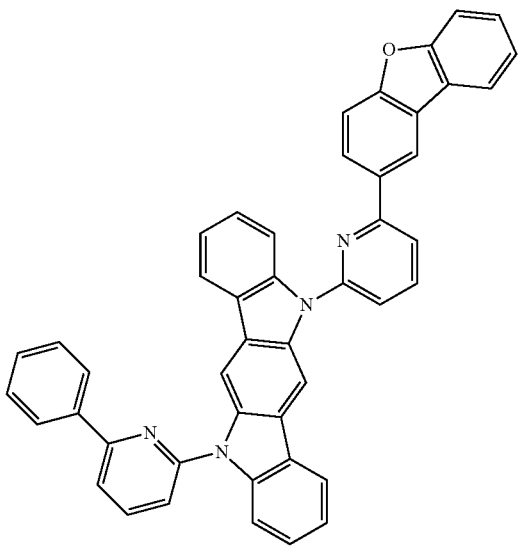
1-101
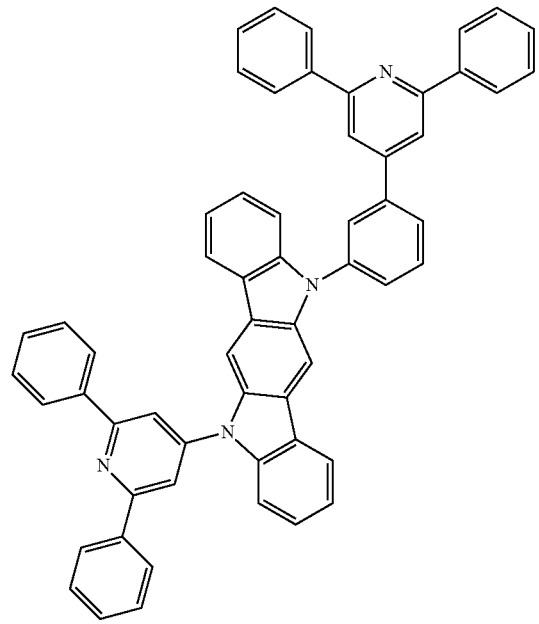
1-102
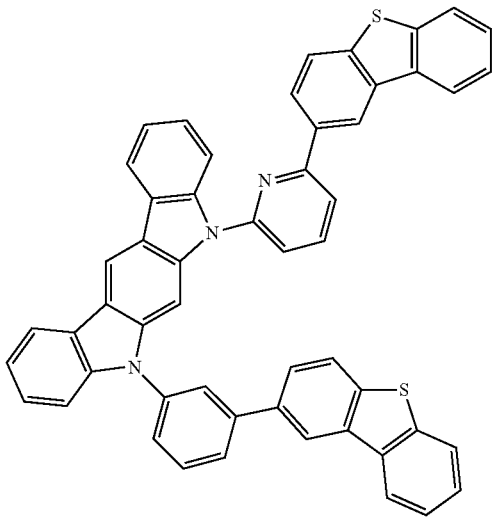

-continued
1-103
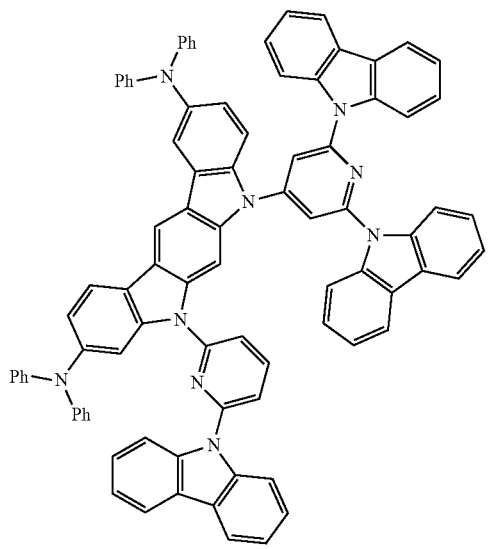
1-104
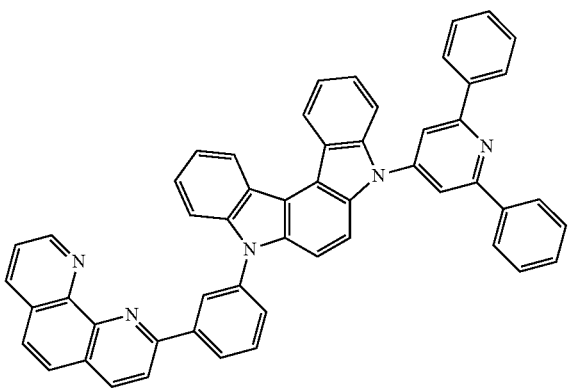
1-105
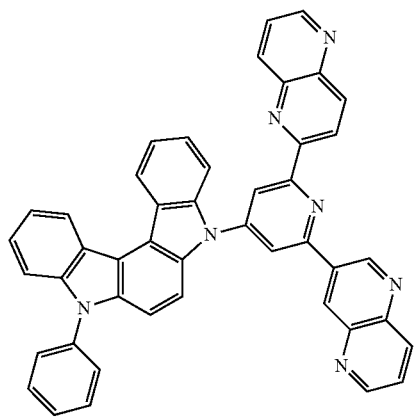
1-106
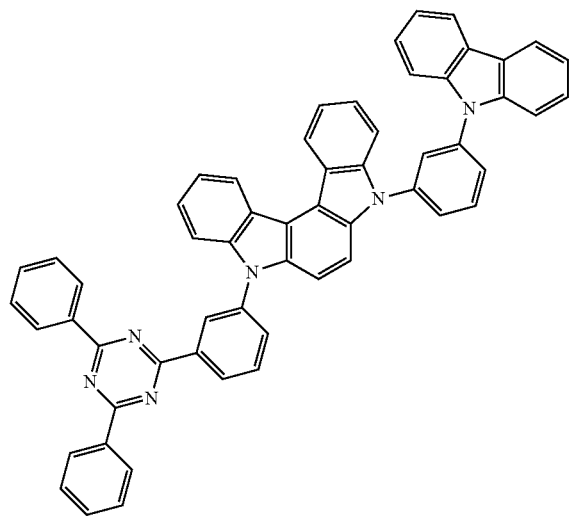
1-107
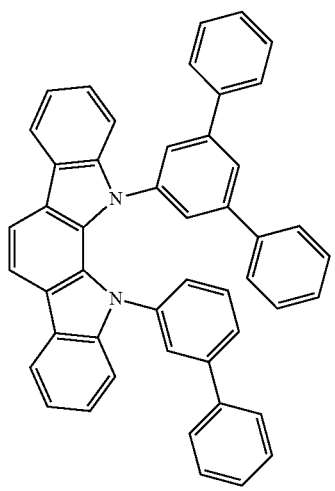
1-108
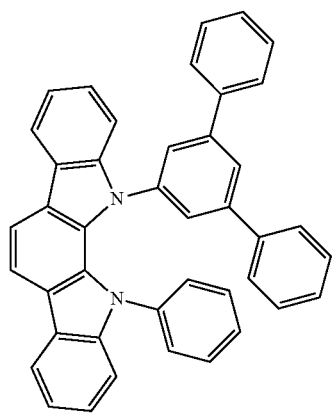

-continued
1-109
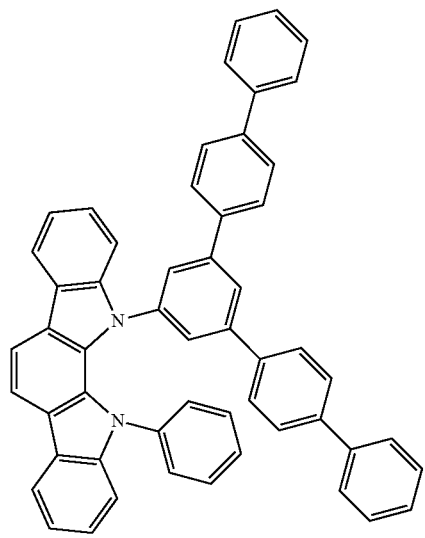
1-110
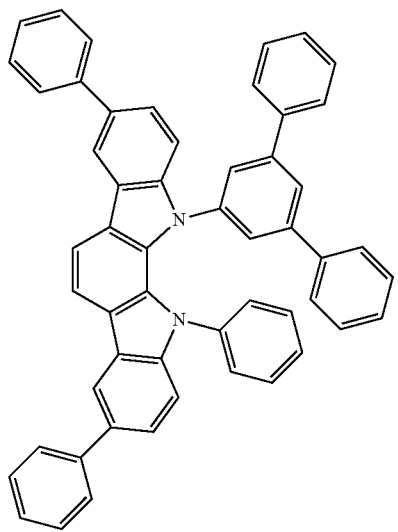
1-111
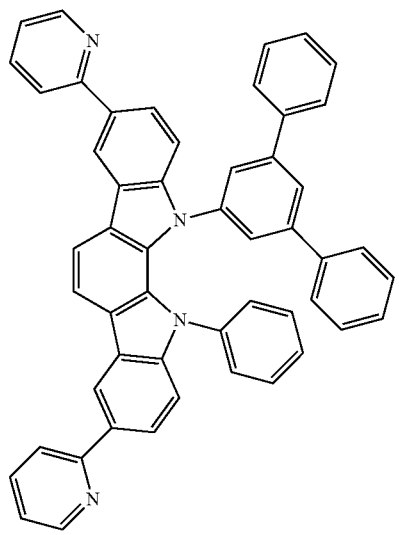
1-112
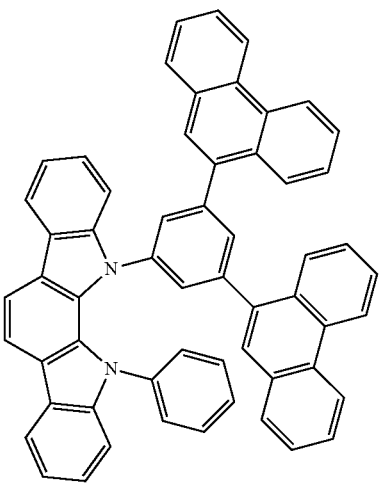
1-113
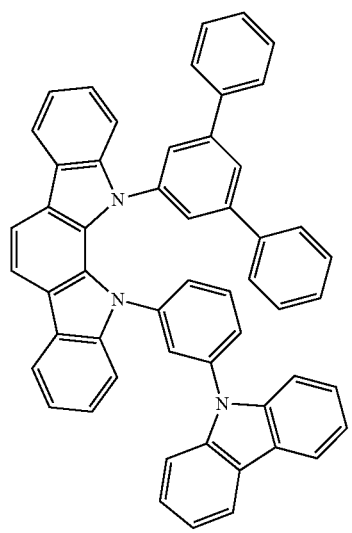
1-114
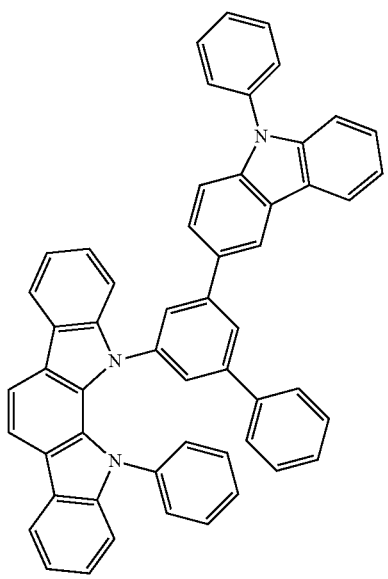

-continued
1-115
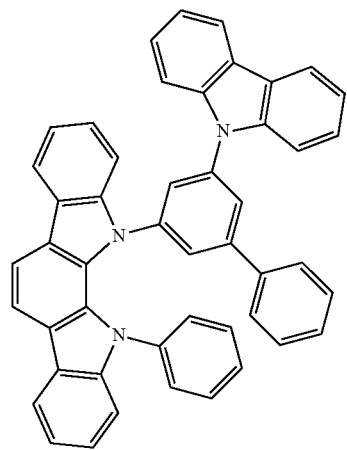
1-116
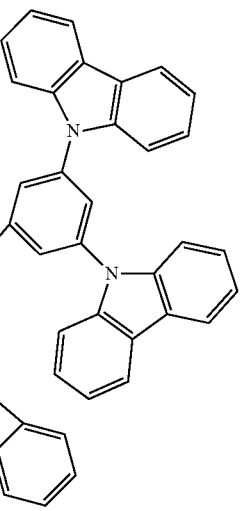
1-117
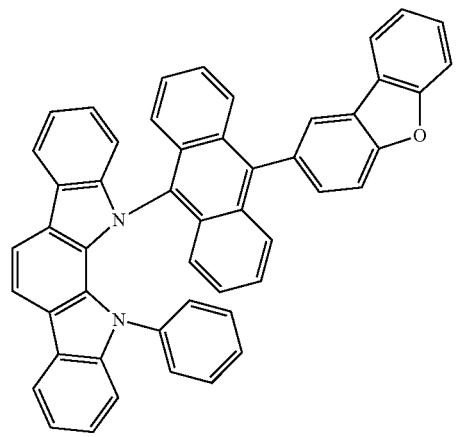
1-118
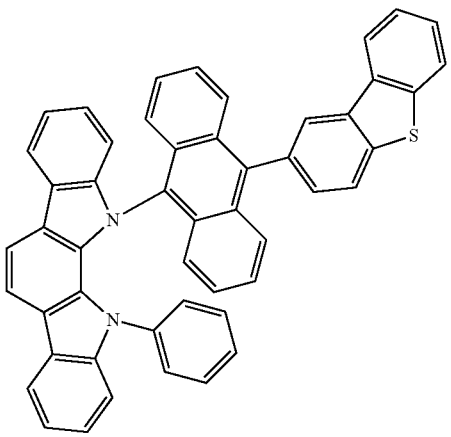
1-119
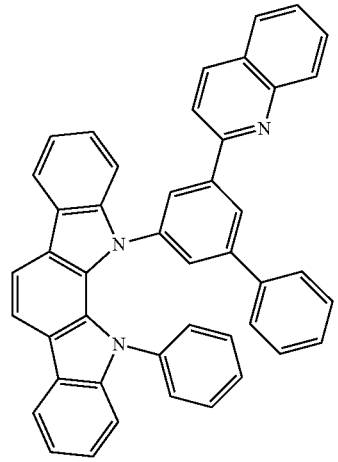
1-120
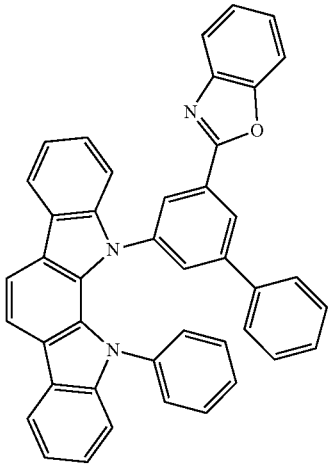

-continued
1-121
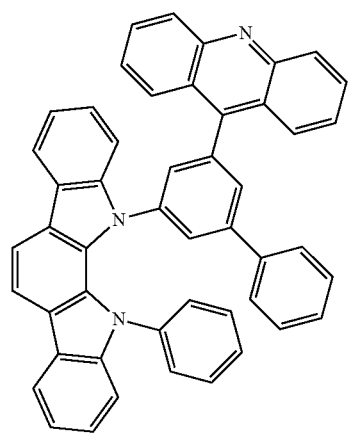
1-122
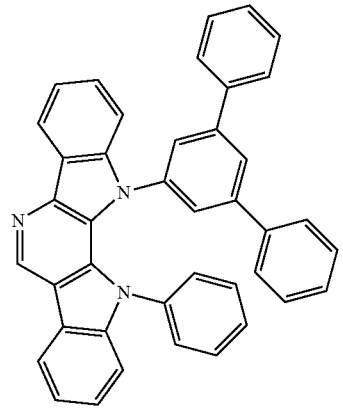
1-123
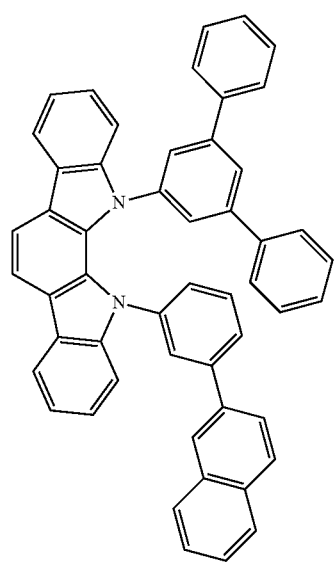
1-124
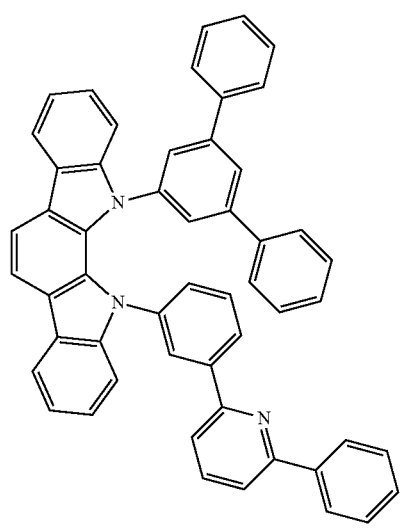
1-125
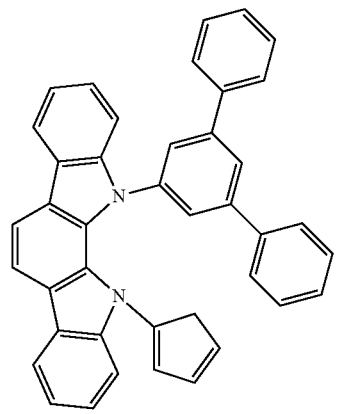
1-126
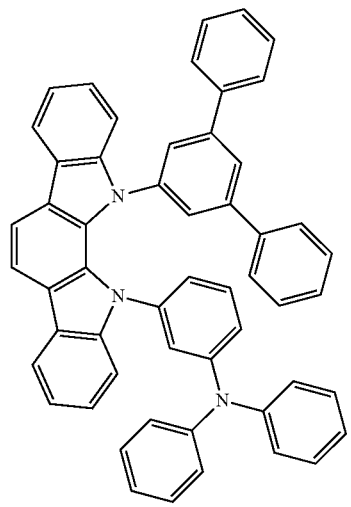

-continued
1-127
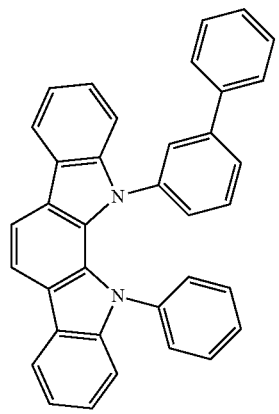
1-128
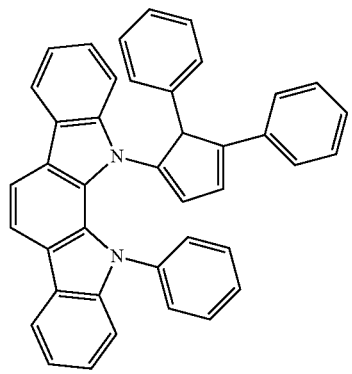
1-129
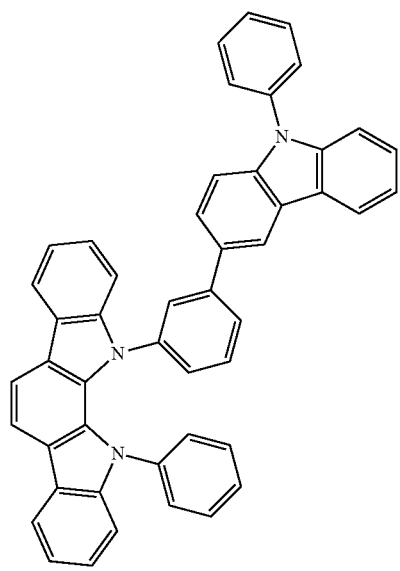
1-130
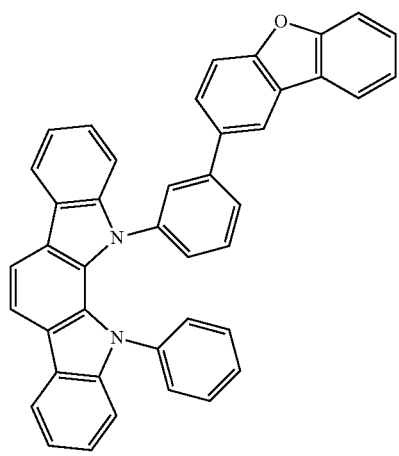
1-131
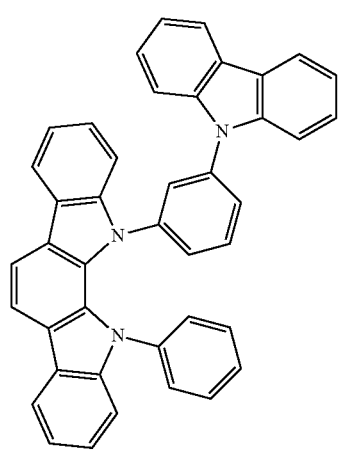
1-132
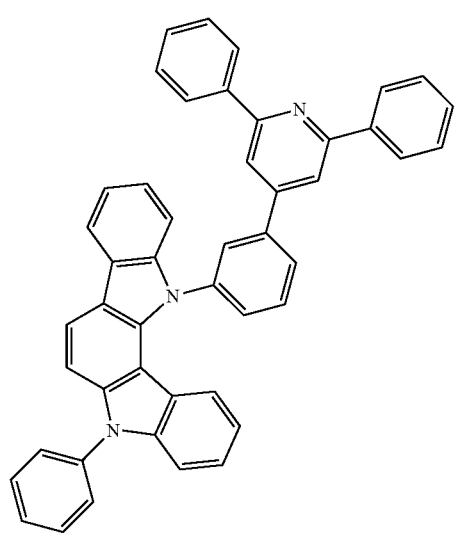

-continued
1-133
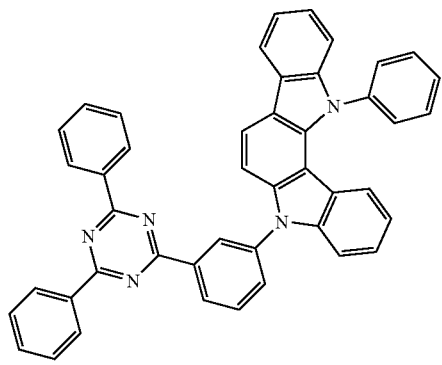
1-134
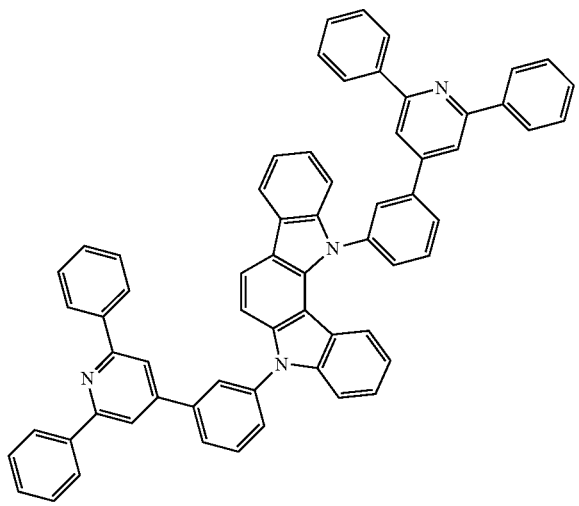
1-135
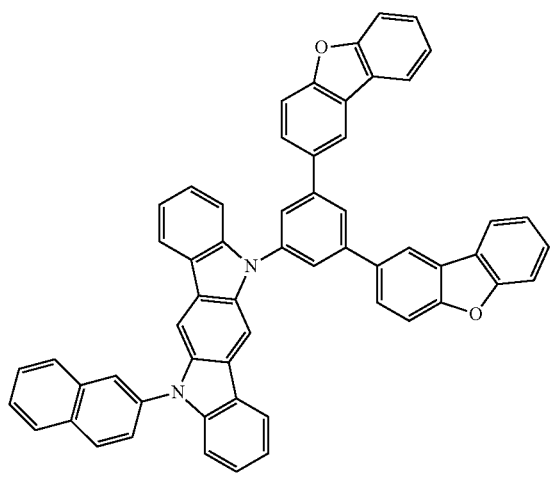
1-136
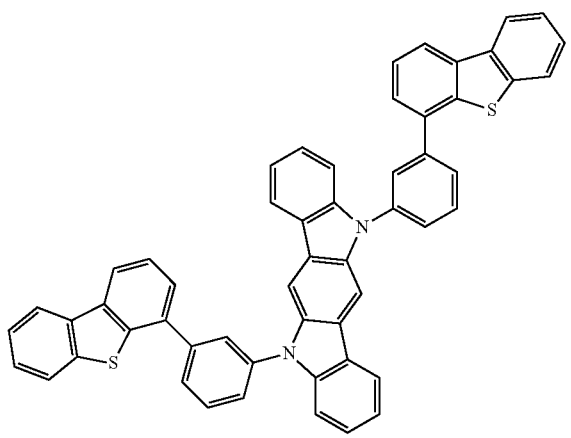
1-137
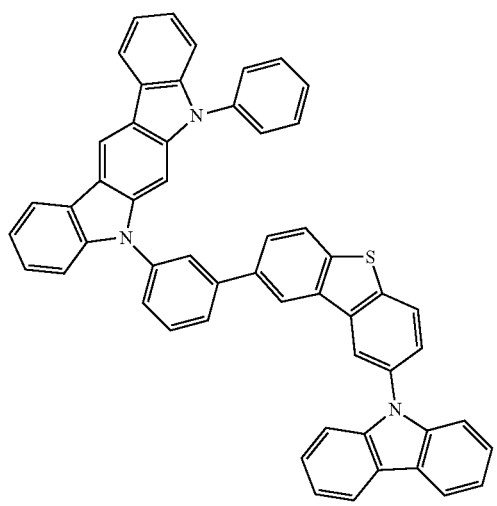
1-138
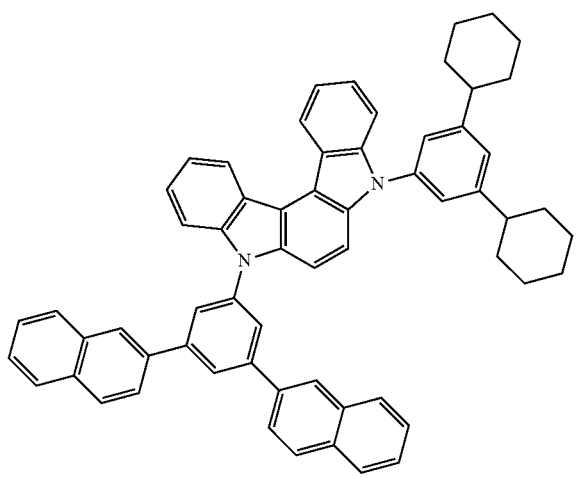

-continued
2-1
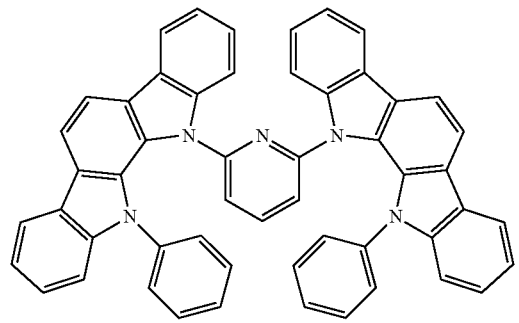
2-2
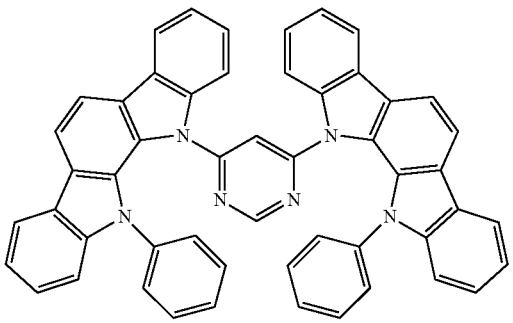
2-3
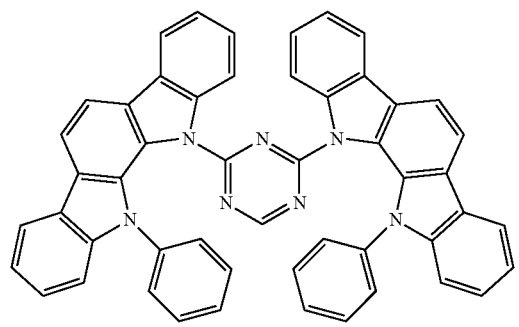
2-4
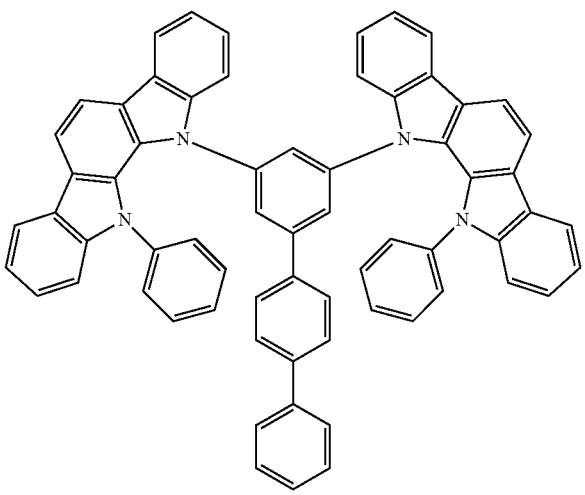
2-5
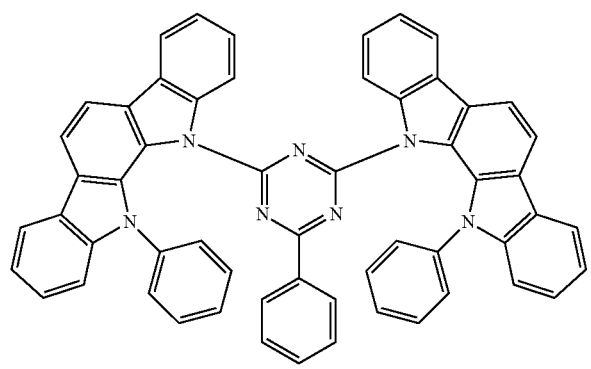
2-6
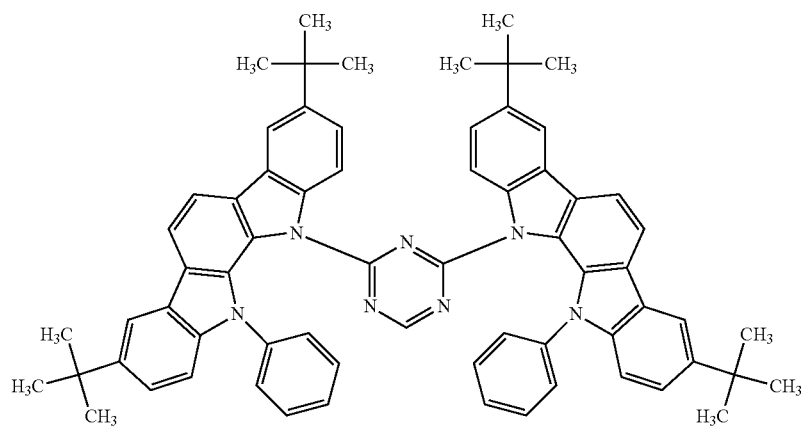

-continued
2-7
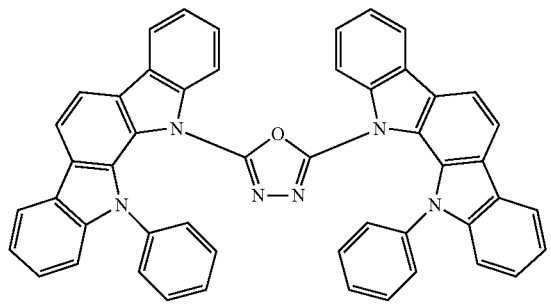
2-8
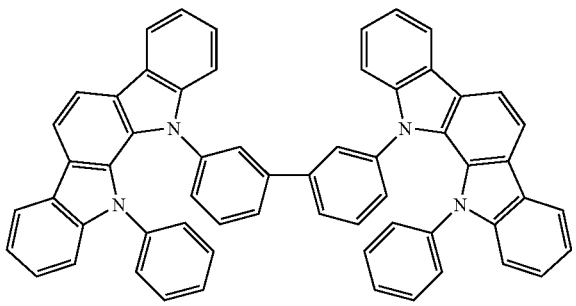
2-9
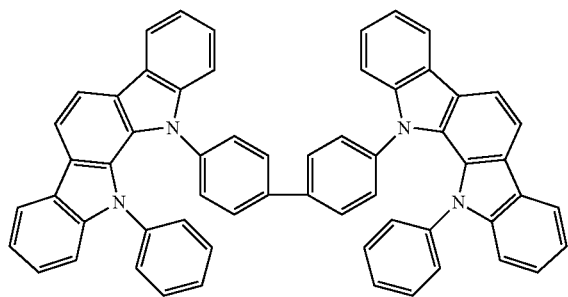
2-10
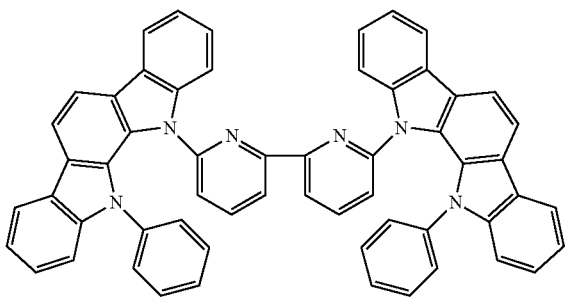
2-11
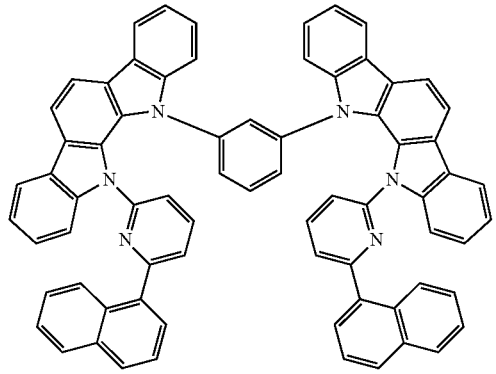
2-12
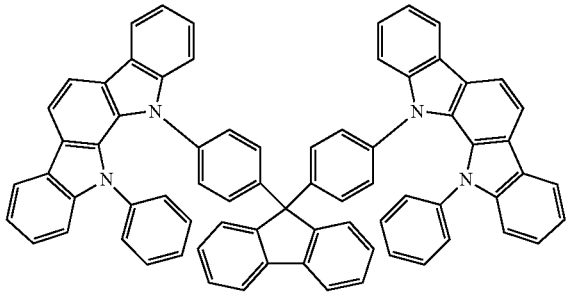
2-13
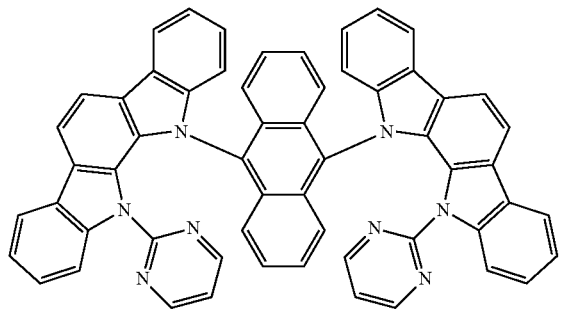
2-14
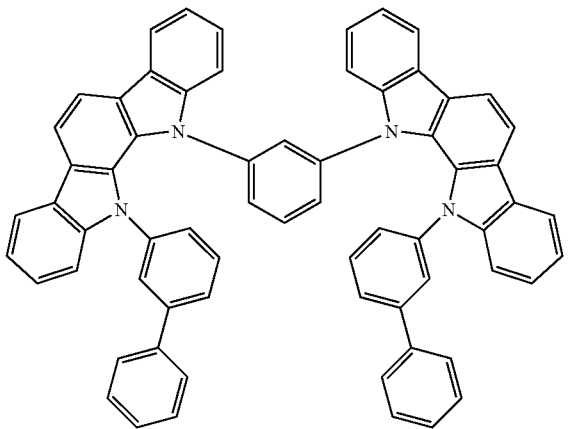

-continued
2-15
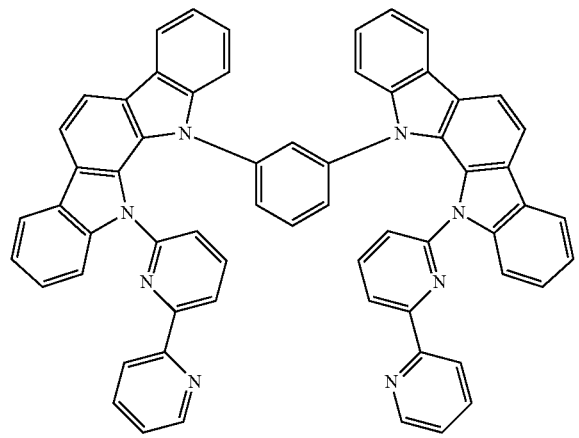
2-16
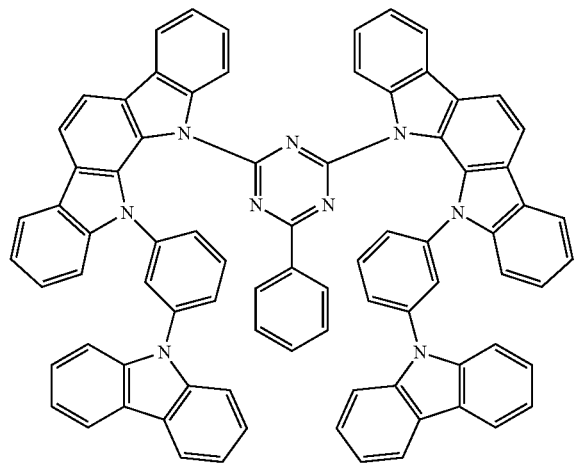
2-17
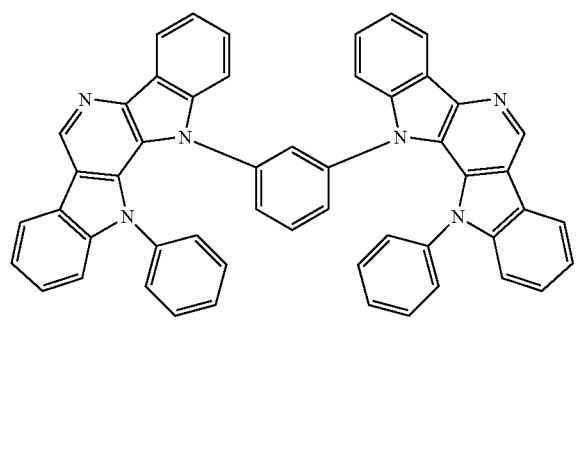
2-18
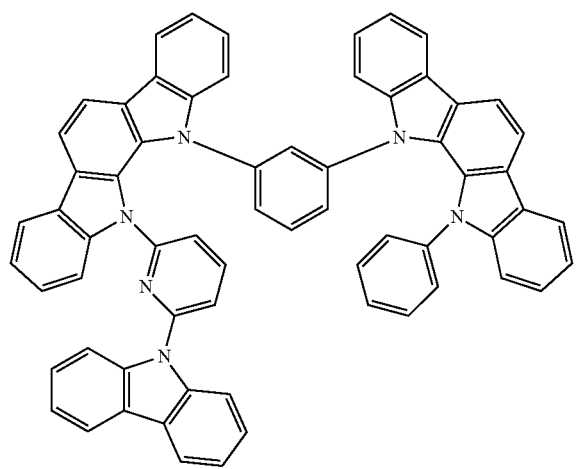
2-19
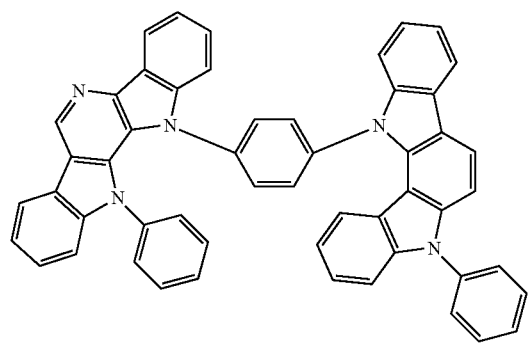
2-20
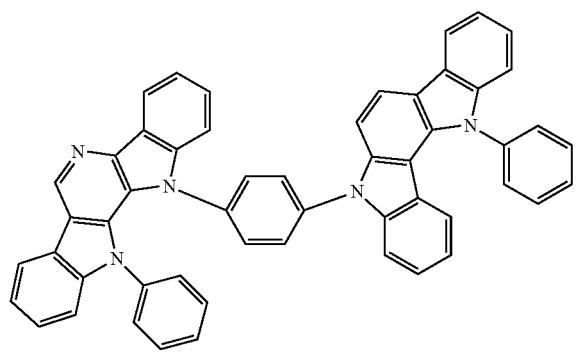

-continued
2-21
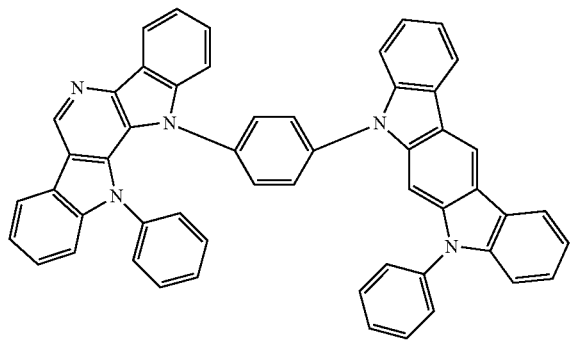
2-22
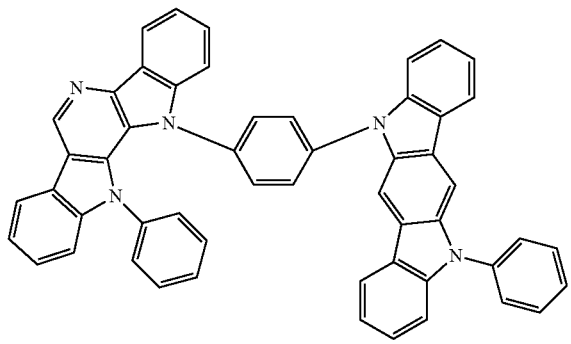
2-23
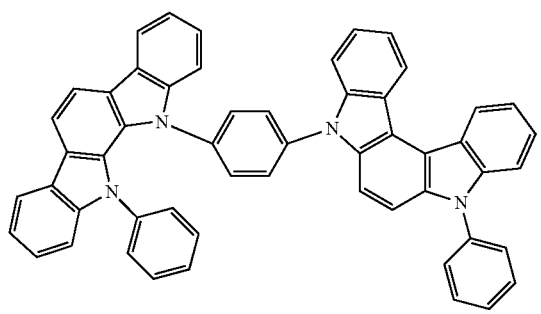
2-24
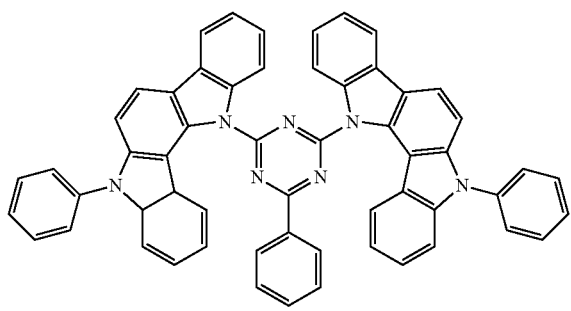
2-25
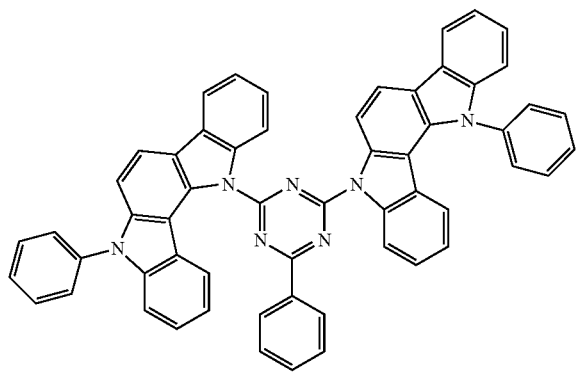
2-26
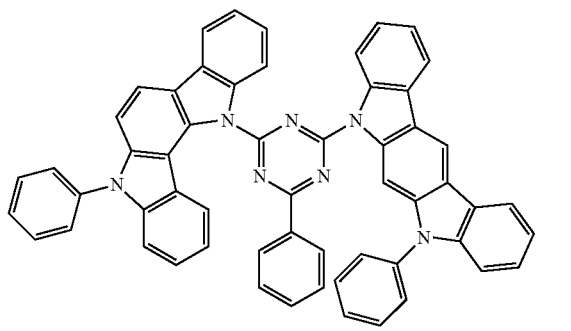
2-27
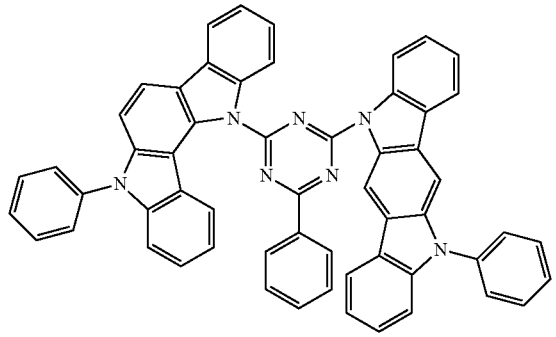
2-28
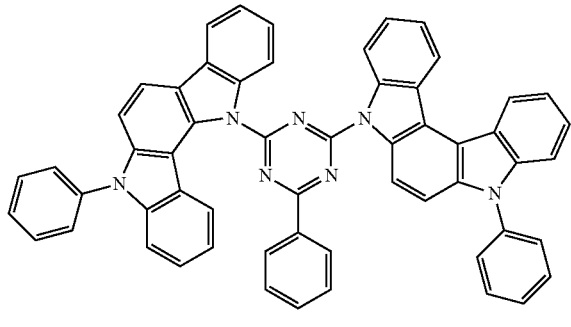

-continued
2-29
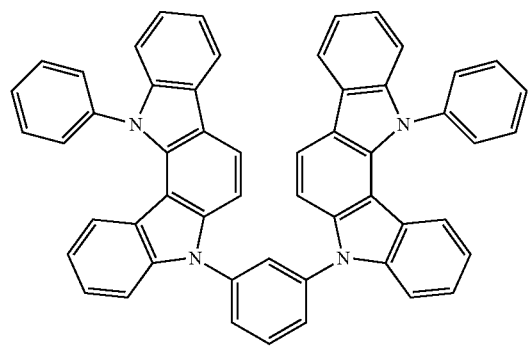
2-30
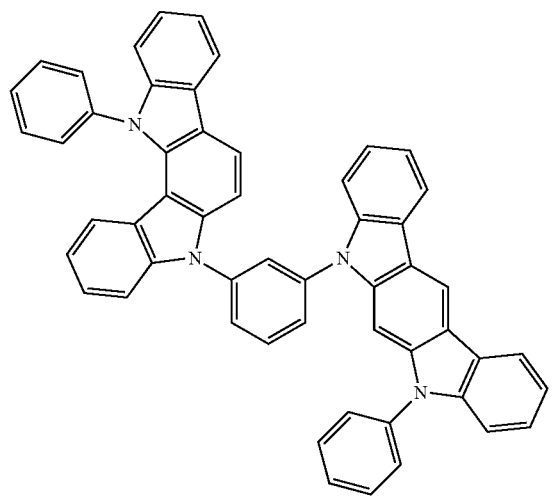
2-31
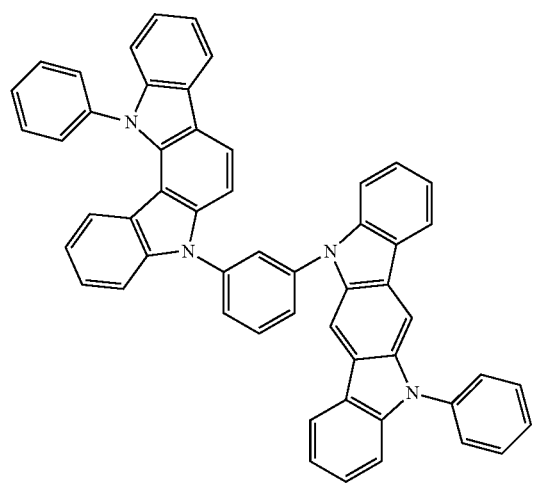
2-32
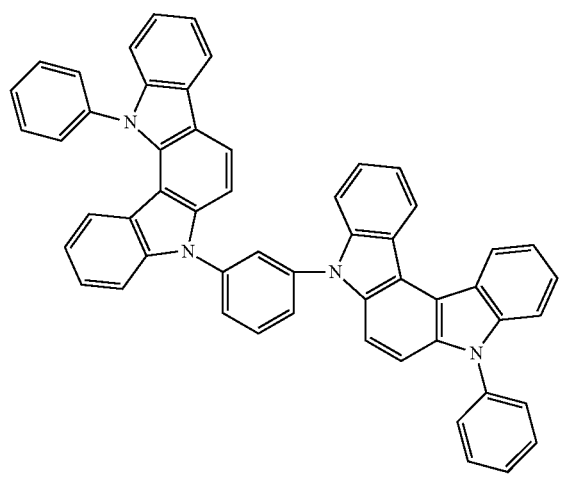
2-33
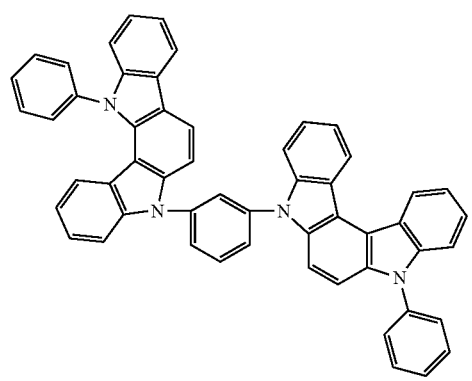
2-34
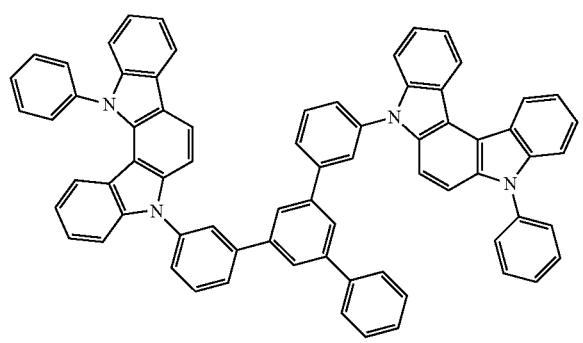

-continued
2-35
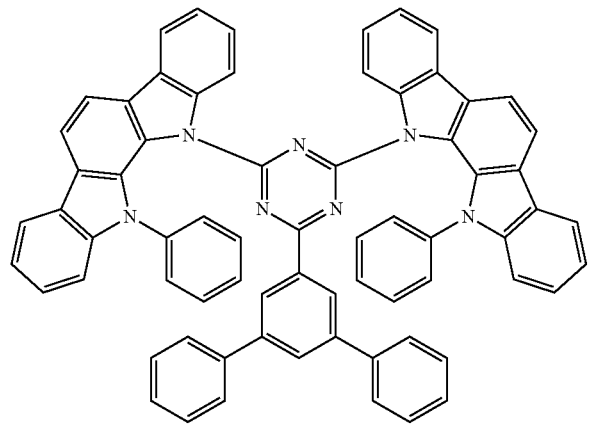
2-36
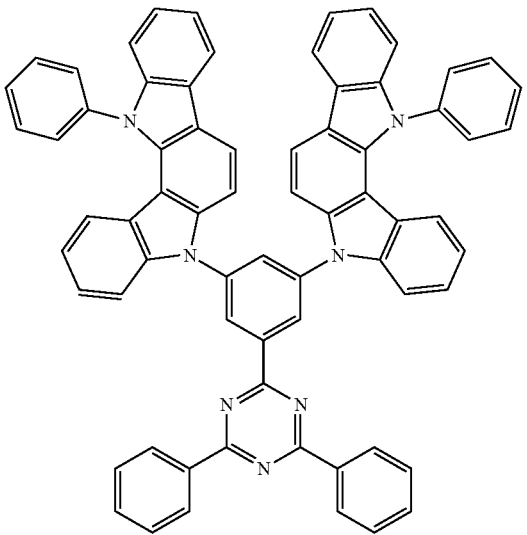
2-37
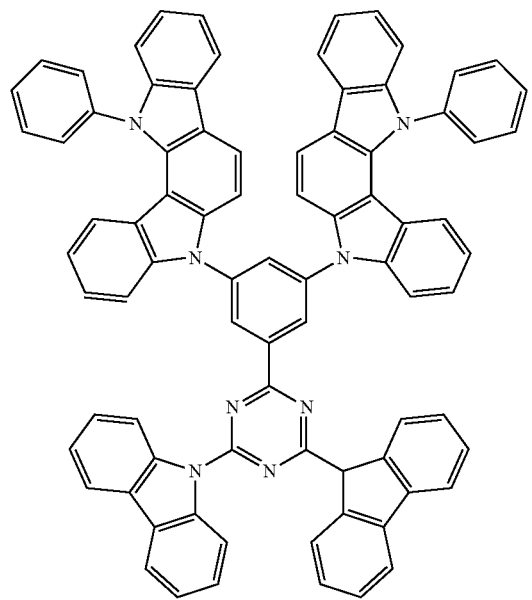
2-38
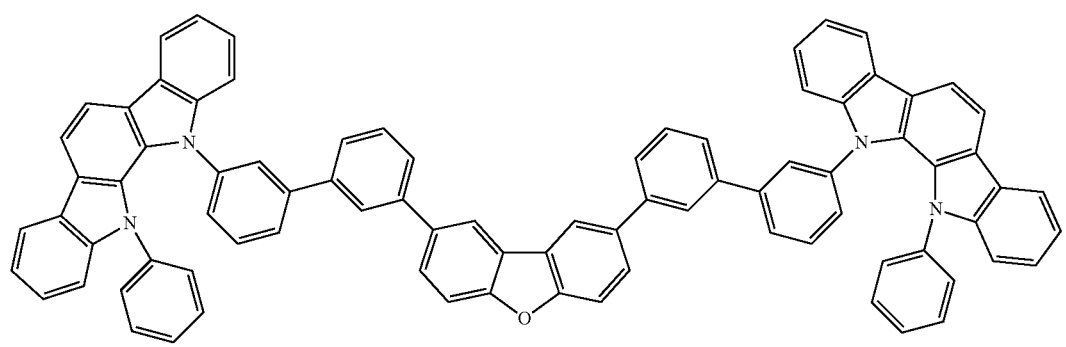

2-39
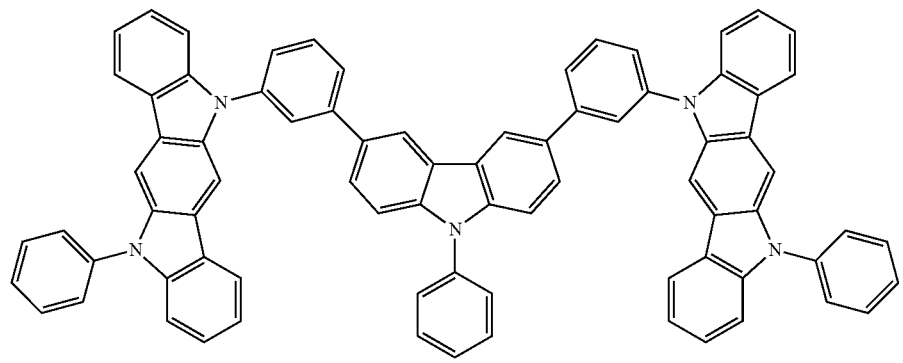
2-40
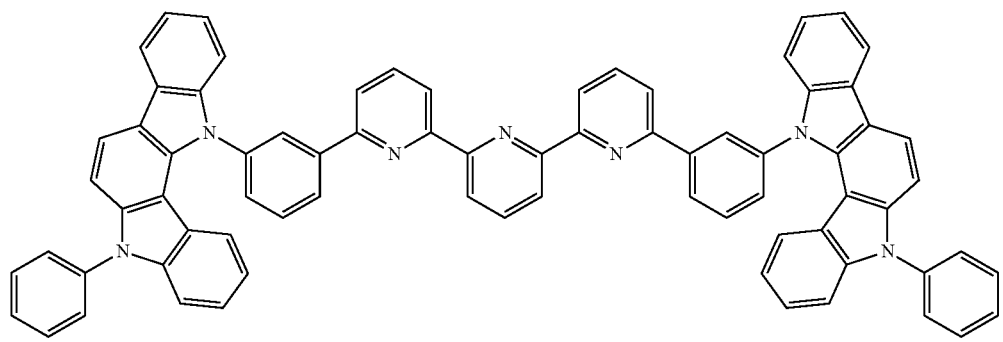
2-41
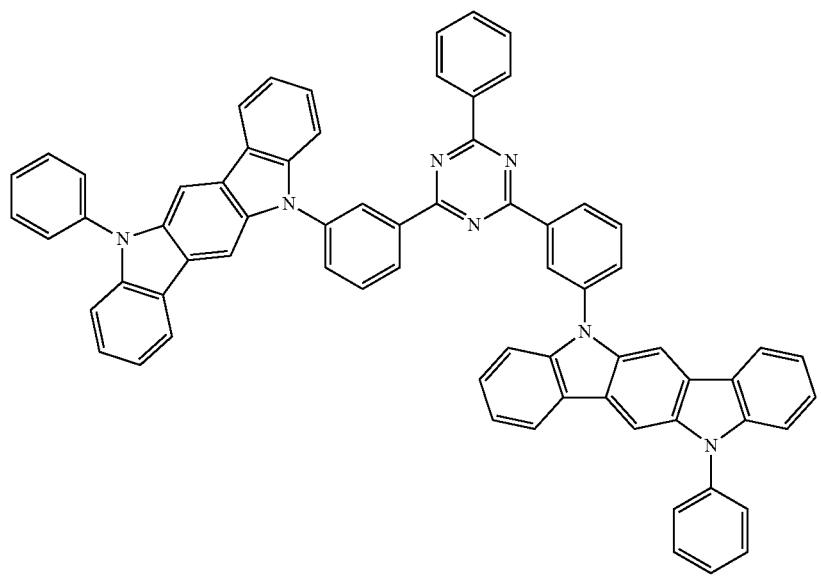
2-42
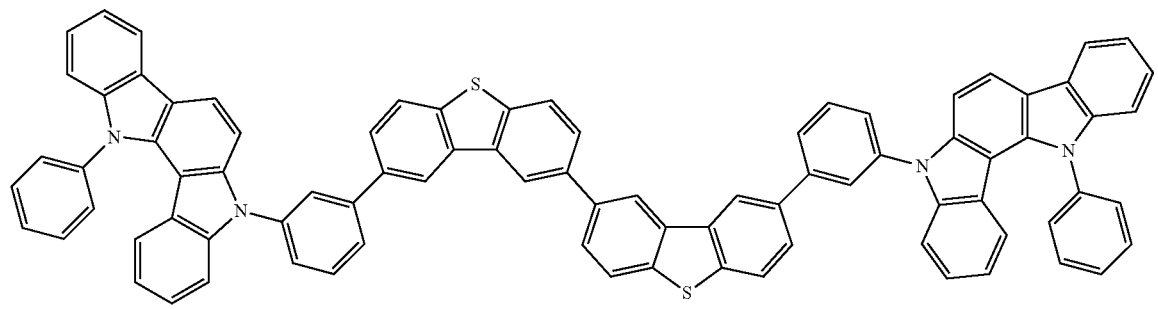

2-43

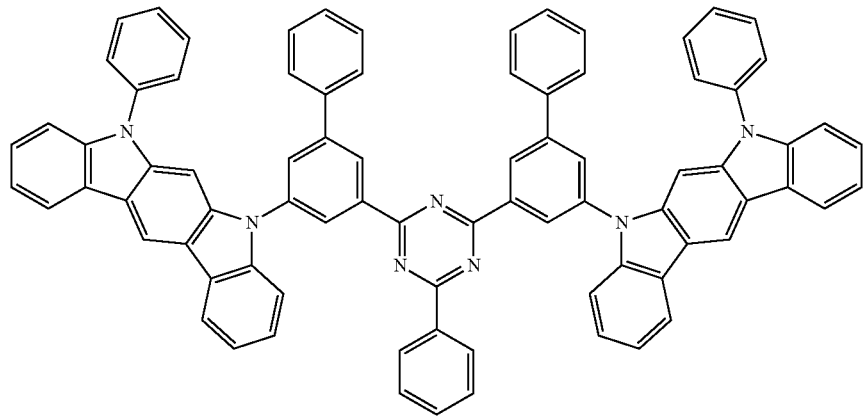

2-44

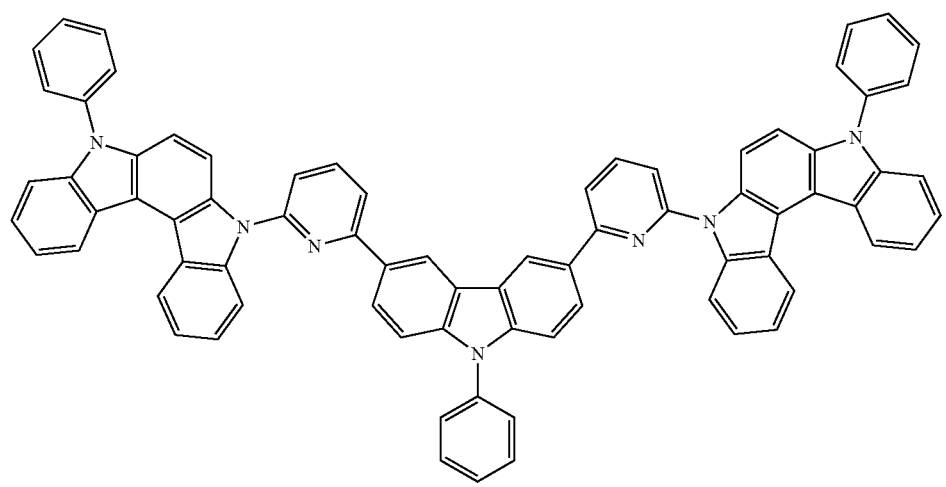

In the general formula (3), l and m each represent an integer of 1 or 2, and $R_9$ to $R_{12}$ each independently represent hydrogen, an alkyl group having 1 to 20 carbon atoms, an acyl group having 2 to 20 carbon atoms, or an alkoxy group having 2 to 20 carbon atoms, preferably hydrogen, an alkyl group having 1 to 10 carbon atoms, or an alkoxy group having 1 to 10 carbon atoms.

In the general formula (3), $R_{13}$ and $R_{14}$ each independently represent hydrogen or an alkyl group having 1 to 20 carbon atoms, preferably hydrogen or an alkyl group having 1 to 10 carbon atoms.

In the general formula (3), n represents an integer of from 1 to 6, preferably 3 or 4.

In the general formula (3), $X_3$ to $X_5$ each independently represent C—H or N, preferably C—H.

In the general formula (3), when n represents an integer of 2 or more, $R_{13}$s, $R_{14}$s, and $X_3$s to $X_5$s may each independently change. In addition, the linking position of each ring may be any one of an ortho position, a meta position, and a para position, and is not limited.

Preferred specific examples of the compound represented by the general formula (3) are shown below. However, the compound is not limited thereto.

3-1
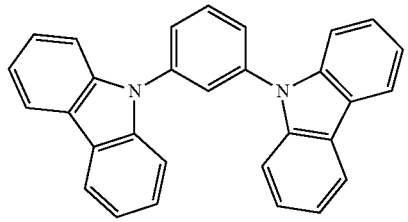
3-2
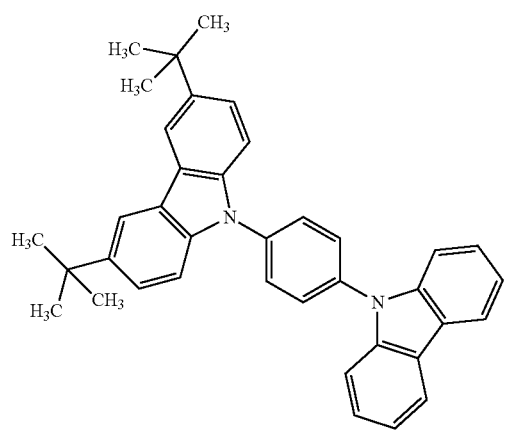
3-3
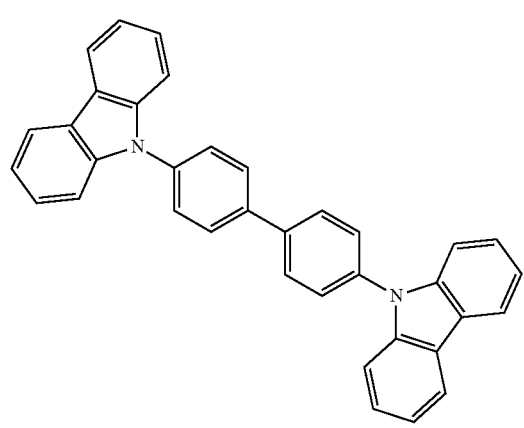
3-4
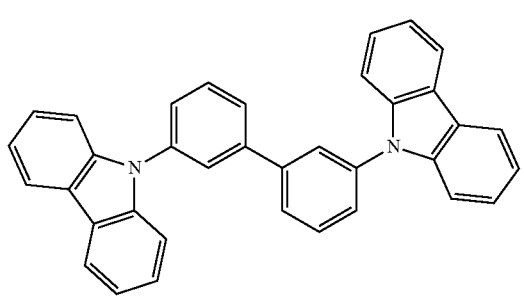
3-5
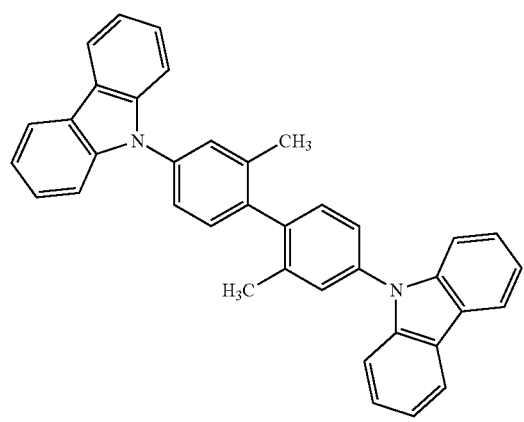
3-6
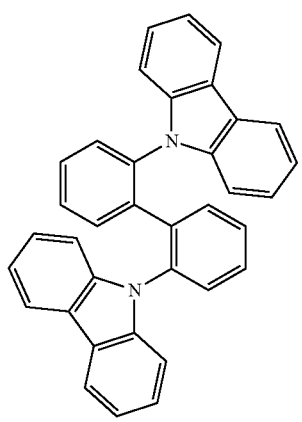

-continued
3-7
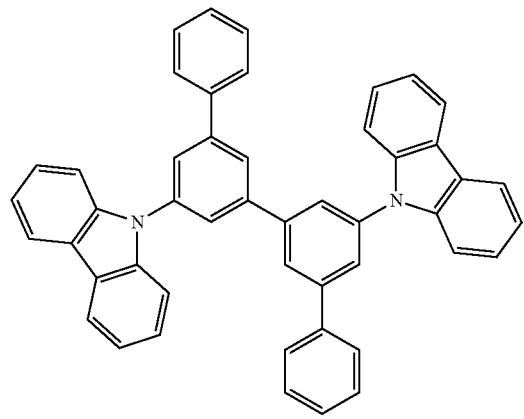
3-8
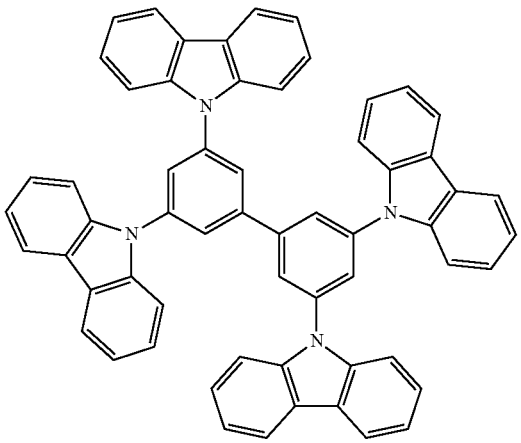
3-9
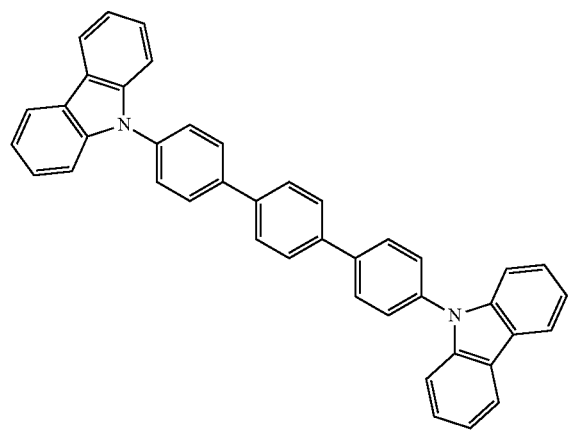
3-10
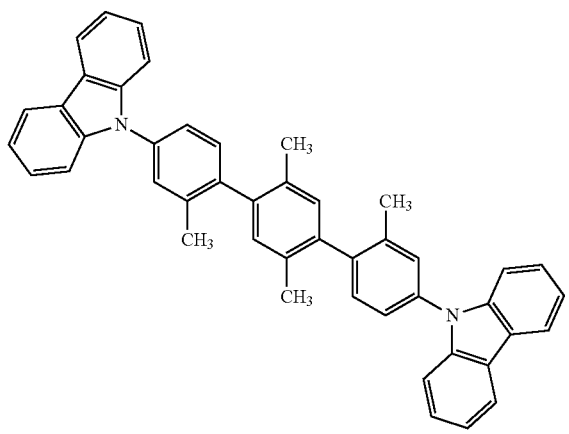
3-11
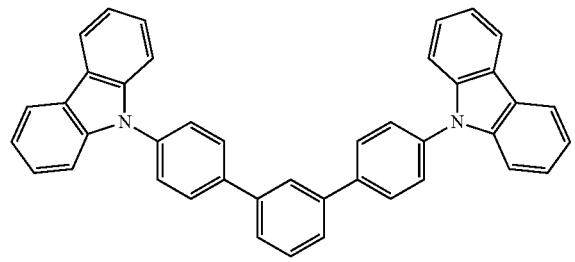
3-12
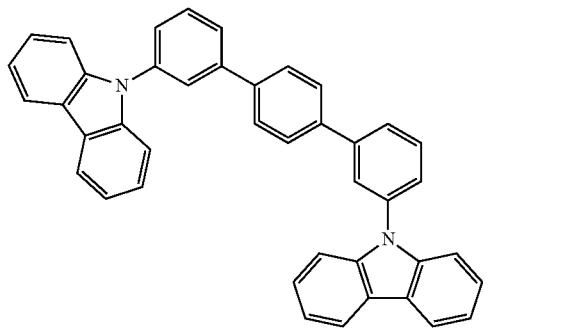
3-13
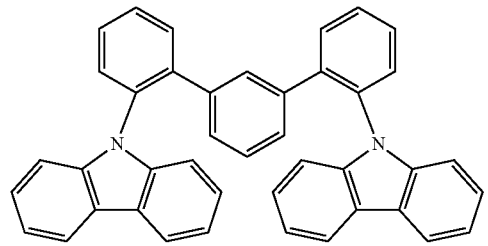
3-14
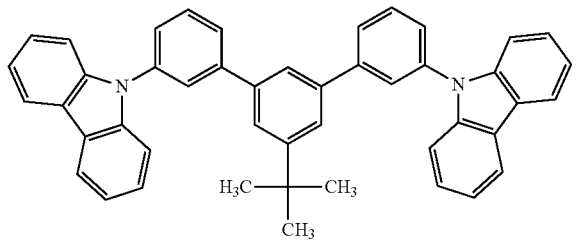

-continued
3-15
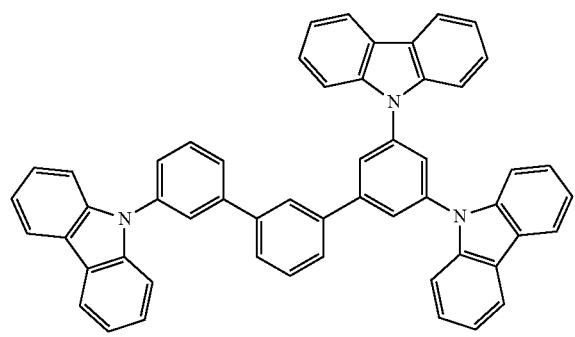
3-16
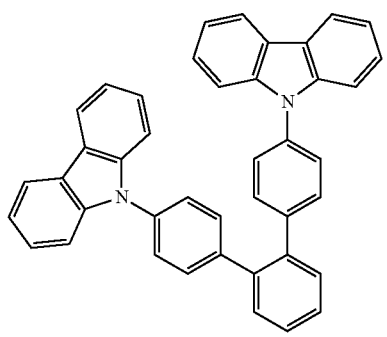
3-17
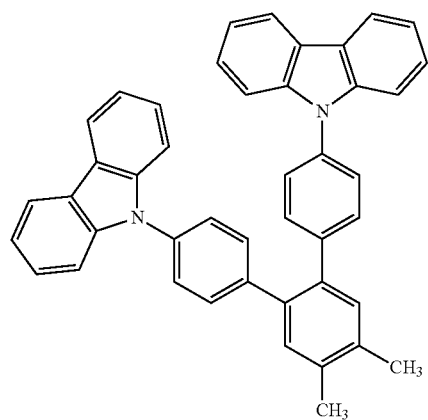
3-18
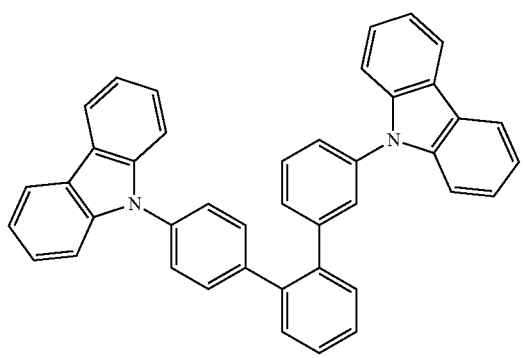
3-19
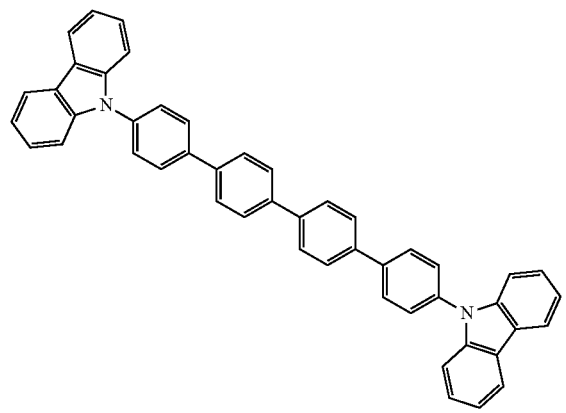
3-20
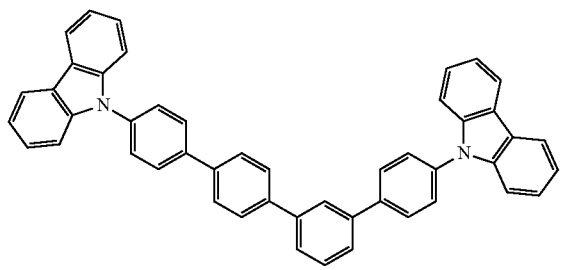
3-21
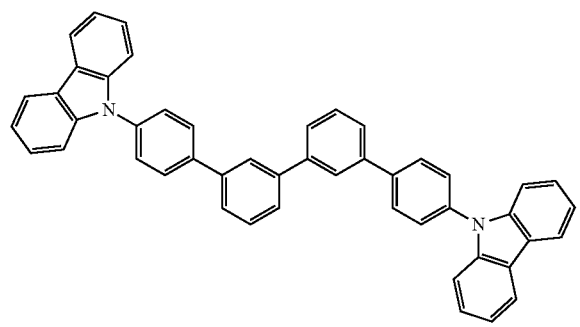
3-22
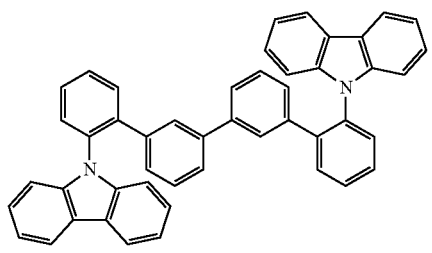

3-23
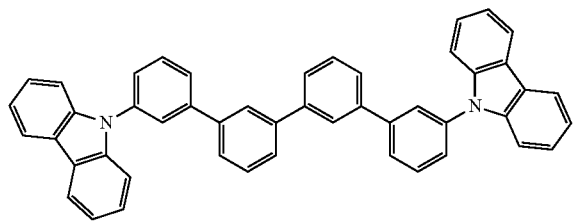
3-24
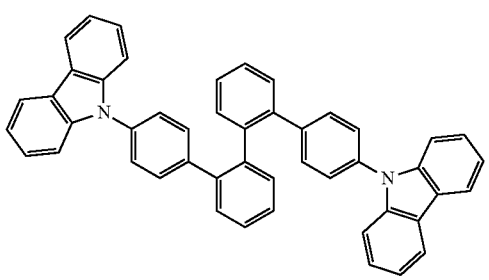
3-25
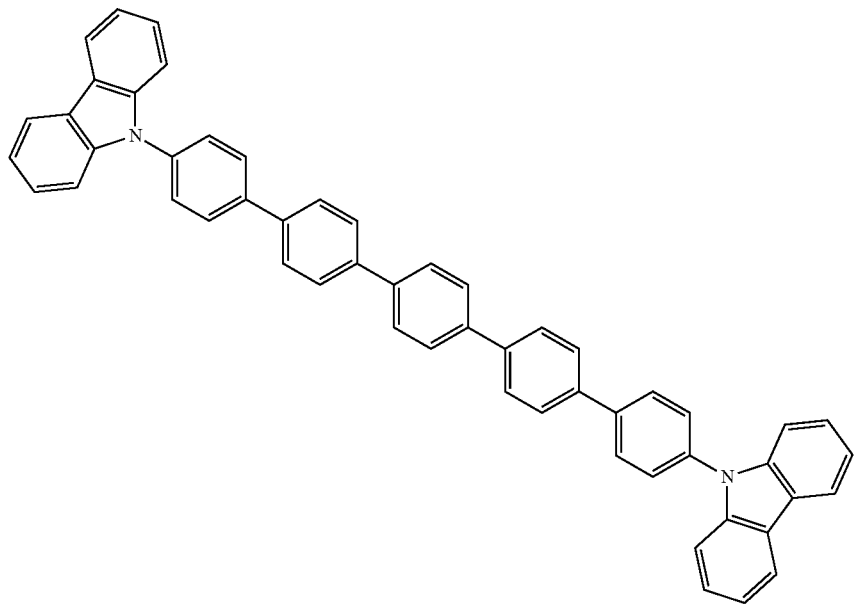
3-26
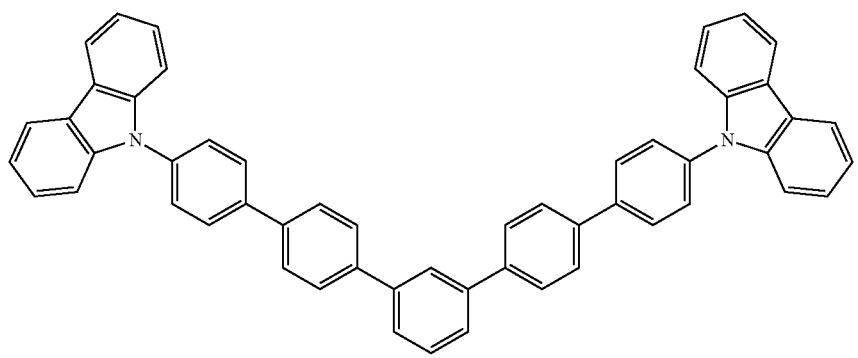

3-27
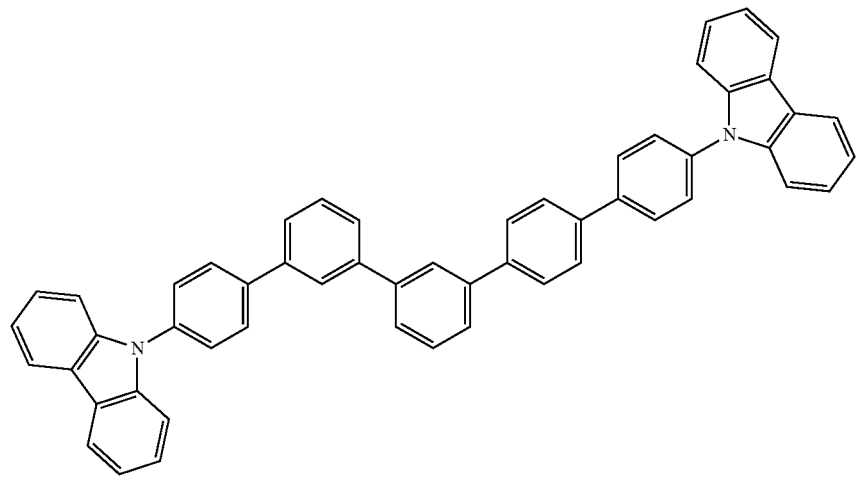
3-28
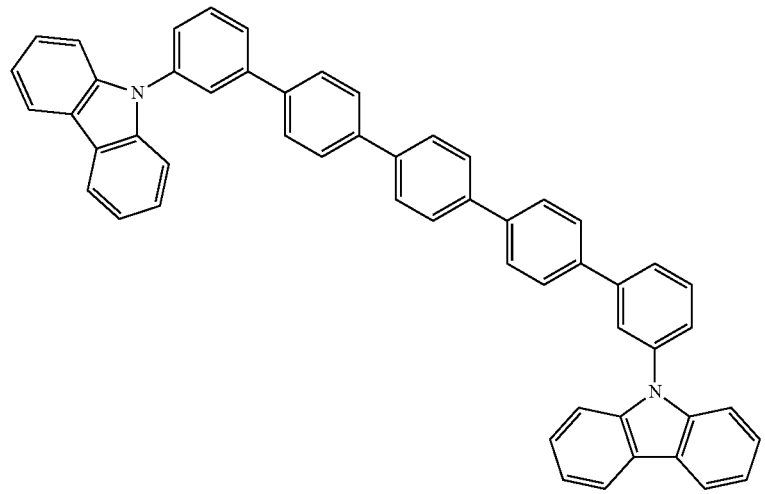
3-29
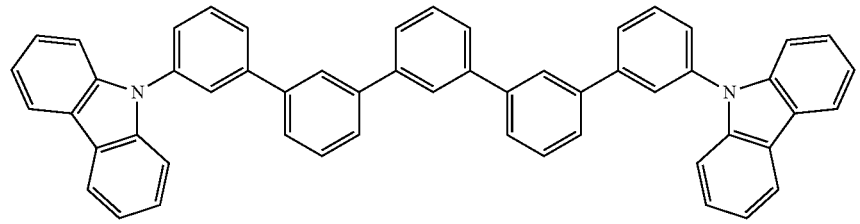
3-30
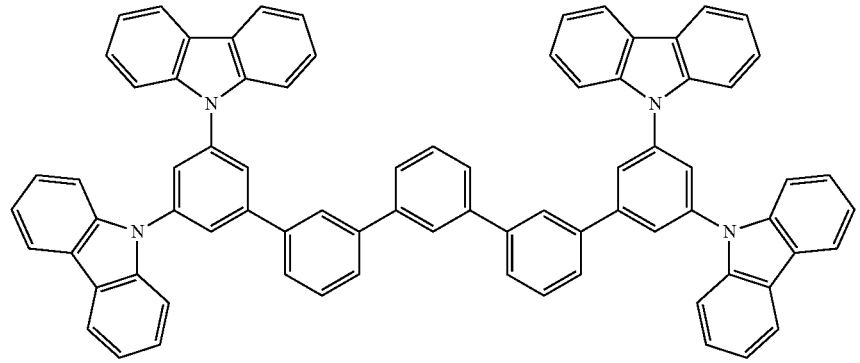

-continued
3-31
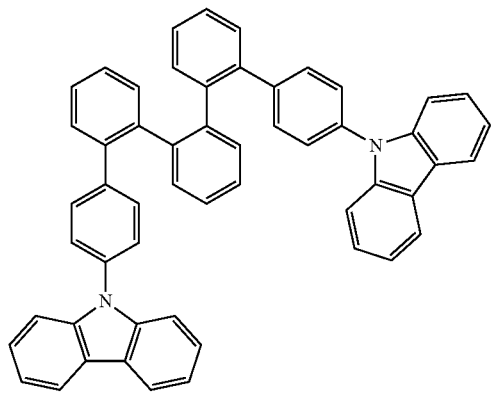
3-32
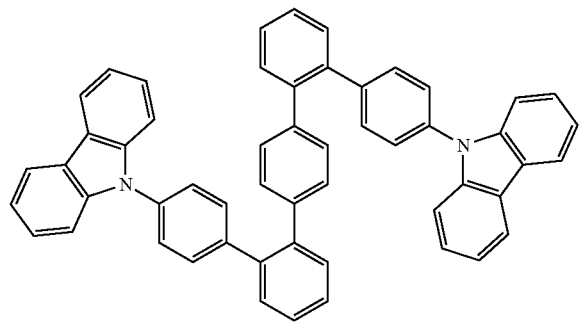
3-33
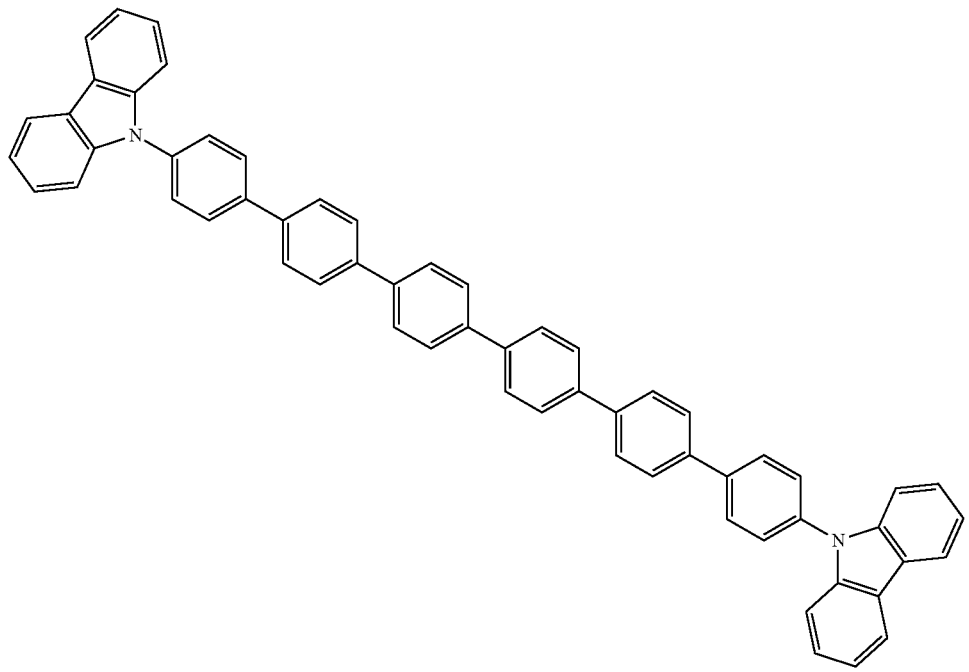
3-34
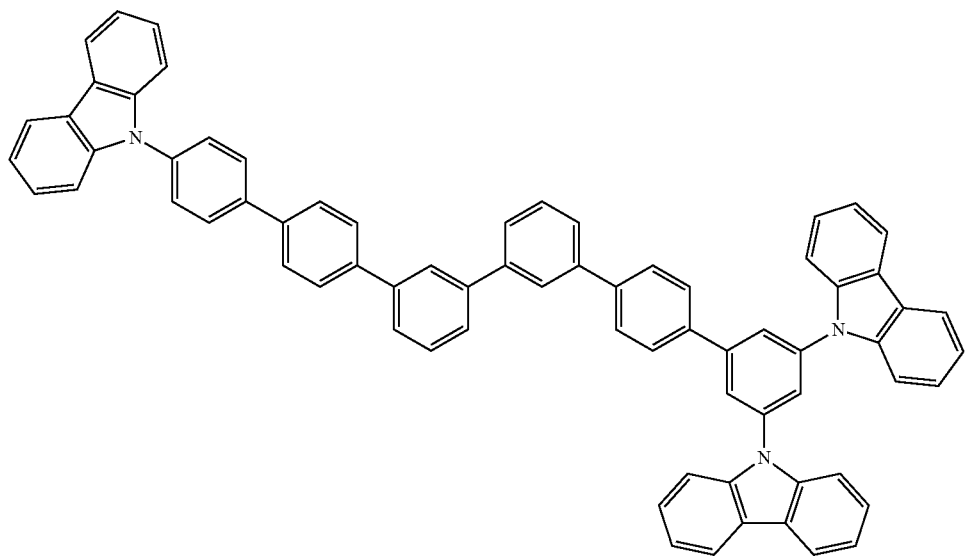

3-35
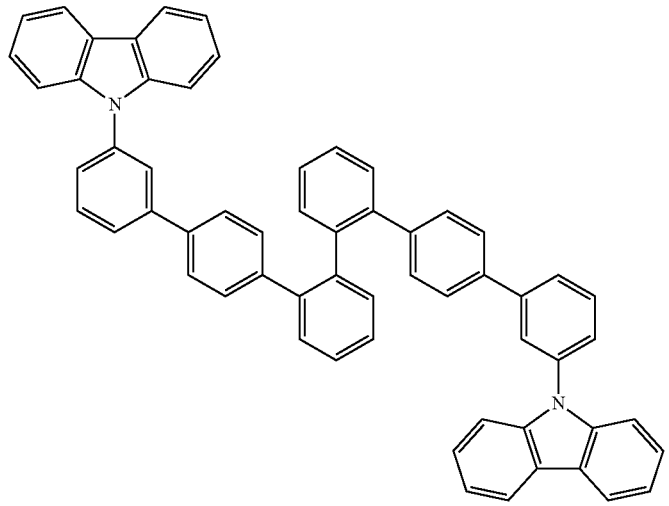
3-36
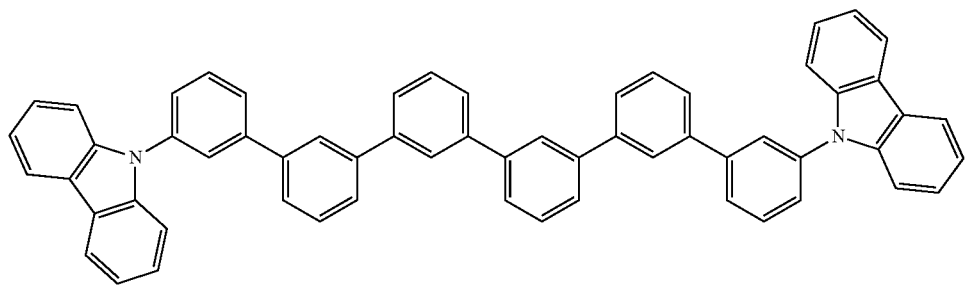
3-37
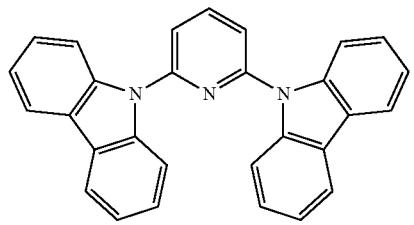
3-38
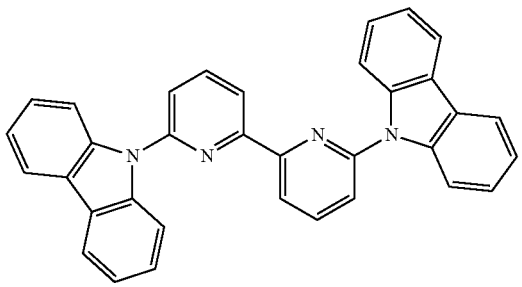
3-39
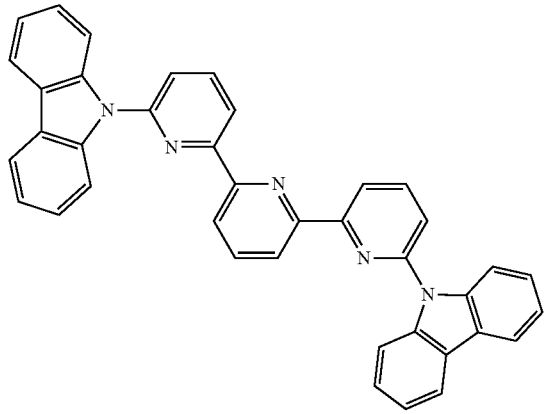
3-40
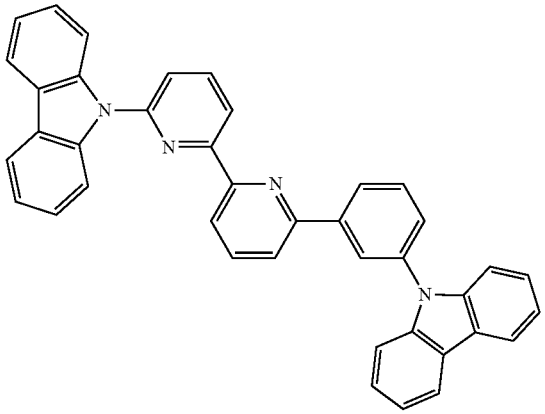

-continued
3-41
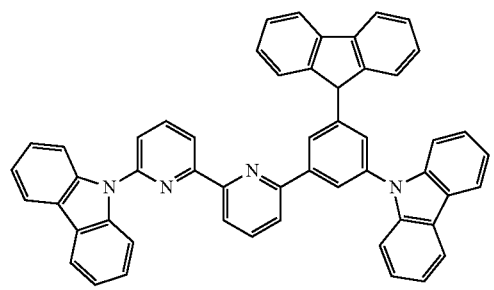
3-42
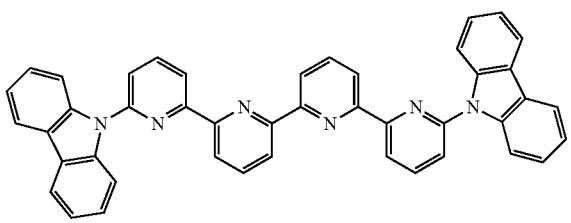
3-43
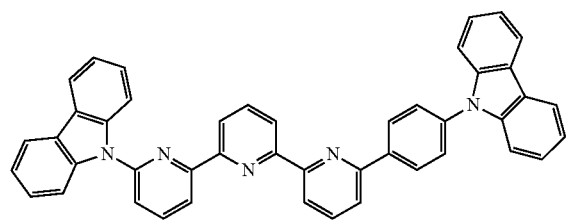
3-44
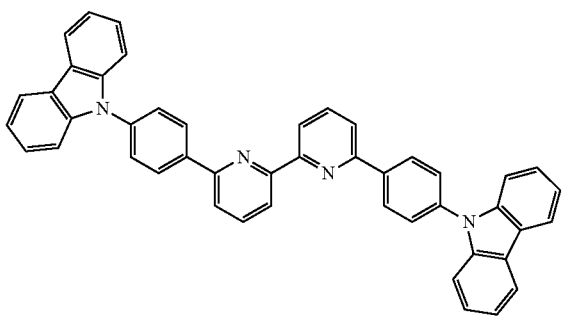
3-45
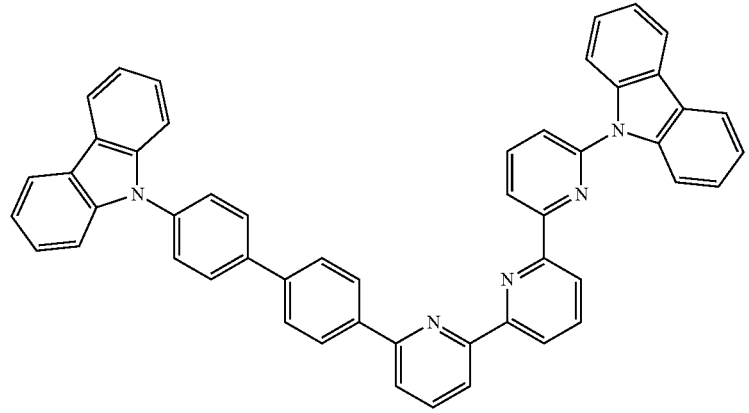
3-46
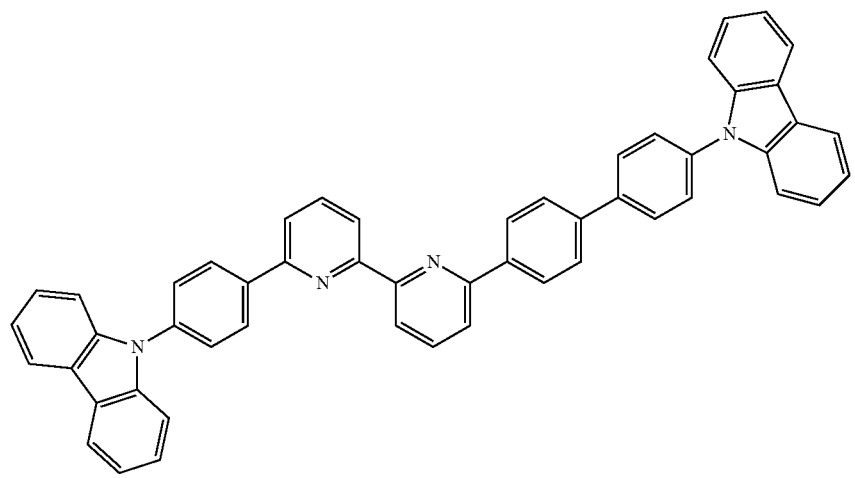

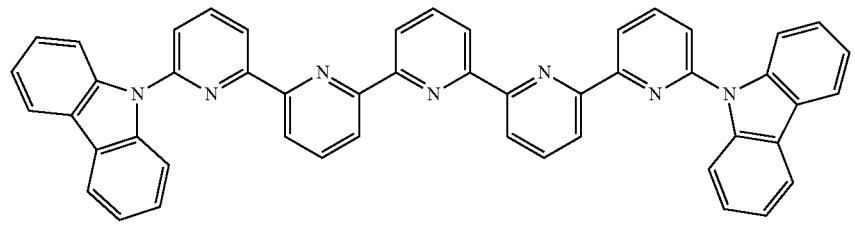
3-47
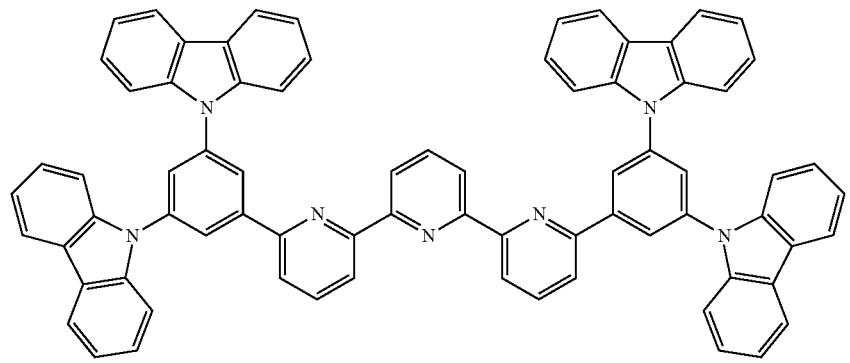
3-48
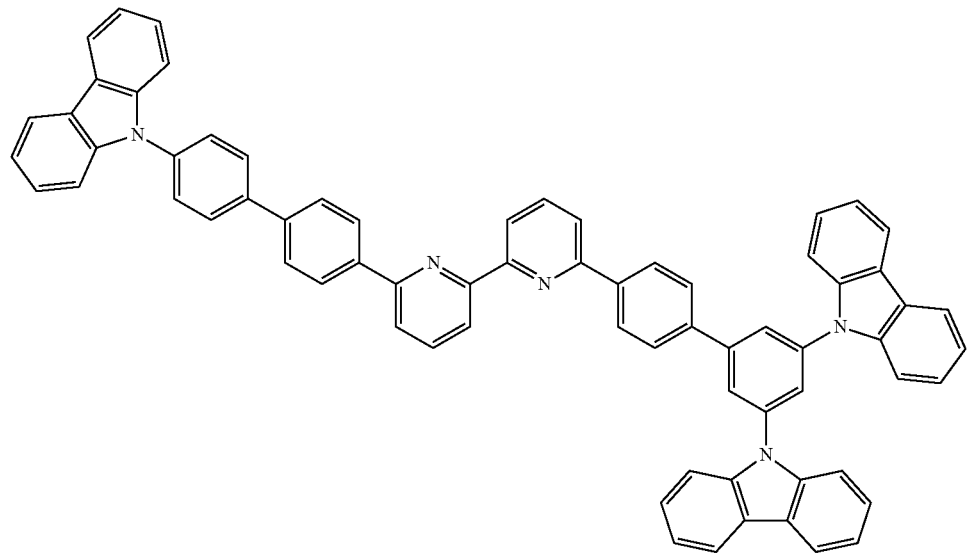
3-49
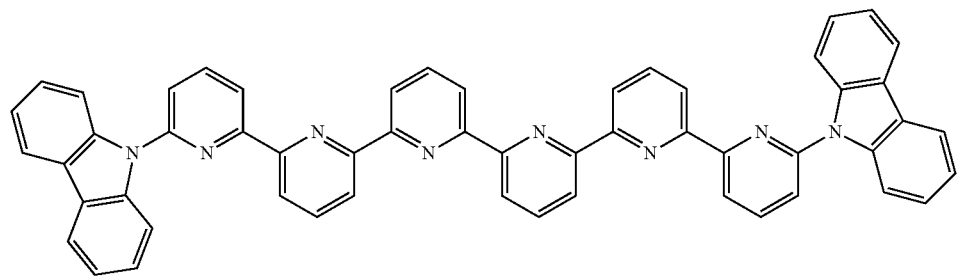
3-50

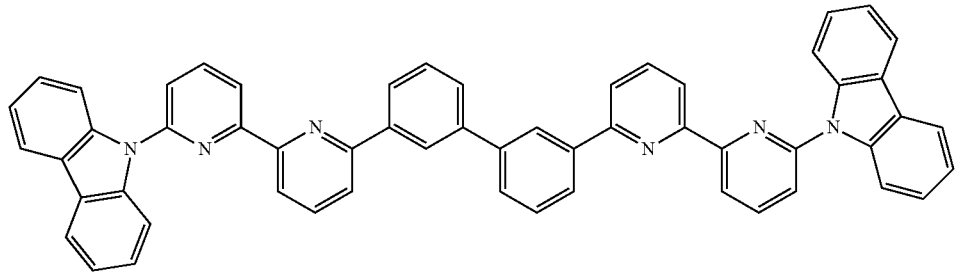

3-51

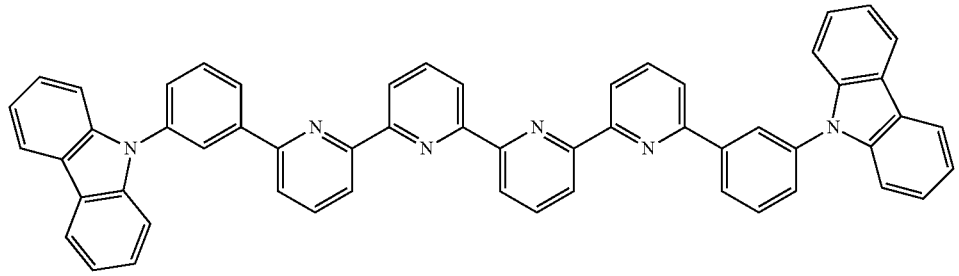

3-52

In addition, a good result is obtained when a difference in EA between the two host materials is more than 0.1 eV. When hosts different from each other in EA by 0.1 eV or less are mixed, a charge balance remains nearly unchanged, and hence the thin-film stability of the device can be improved without the loss of its original characteristics. In contrast, however, when hosts different from each other in EA by more than 0.1 eV are mixed, the path along which an electron flows can be limited to the host having the larger EA of the two hosts to be mixed, and hence an electron flow in a light-emitting layer can be suppressed. As a result, an electron can be easily confined in the light-emitting layer, and hence an device having a long lifetime while maintaining high efficiency can be provided. The difference in EA preferably falls within the range of from 0.2 to 1.5 eV. It should be noted that a value for an EA can be calculated by using a value for an ionization potential in a host material thin film obtained by photoelectron spectroscopy and a value for an energy gap determined from an absorption edge of an ultraviolet-visible absorption spectrum measured for the film; provided that a measurement method is not limited thereto.

The two host materials may be mixed before the production of the device and deposited from the vapor by using one vapor deposition source, or may be mixed at the time of the production of the device by an operation such as co-deposition involving using a plurality of vapor deposition sources. A mixing ratio (weight ratio) between the host materials, which is not particularly limited, preferably falls within the range of from 95:5 to 5:95, more preferably falls within the range of from 90:10 to 10:90.

Next, the structure of the organic EL device of the present invention is described with reference to the drawings. However, the structure of the organic EL device of the present invention is by no means limited to one illustrated in the drawings.

(1) Construction of Organic EL Device

FIG. 1 is a sectional view schematically illustrating a structure example of a general organic EL device used in the present invention. Reference numeral 1 represents a substrate, reference numeral 2 represents an anode, reference numeral 3 represents a hole-injecting layer, reference numeral 4 represents a hole-transporting layer, reference numeral 5 represents a light-emitting layer, reference numeral 6 represents an electron-transporting layer, reference numeral 7 represents an electron-injecting layer, and reference numeral 8 represents a cathode. The organic EL device of the present invention includes the anode, the light-emitting layer, the electron-transporting layer, and the cathode as its essential layers, and may include any other layer as required. Examples of the other layer include, but not limited to, a hole-injecting/transporting layer, an electron-blocking layer, and a hole-blocking layer. It should be noted that the hole-injecting/transporting layer means any one or both of the hole-injecting layer and the hole-transporting layer.

(2) Substrate

The substrate 1 serves as a support for the organic electroluminescent device, and a quartz or glass plate, a metal plate or a metal foil, a plastic film or sheet, or the like is used. A glass plate, or a smooth and transparent plate made of a synthetic resin such as polyester, polymethacrylate, polycarbonate, or polysulfone is particularly preferred. When a synthetic resin substrate is used, attention needs to be paid to its gas barrier property. The case where the gas barrier property of the substrate is excessively small is not preferred because the organic electroluminescent device may deteriorate owing to outside air that has passed the substrate. Accordingly, a method involving providing at least one surface of the synthetic resin substrate with a dense silicon oxide film or the like to secure the gas barrier property is one preferred method.

(3) Anode

The anode 2 is formed on the substrate 1 and the anode serves to inject a hole into the hole-transporting layer. The anode is typically constituted of, for example, a metal such as aluminum, gold, silver, nickel, palladium, or platinum, a metal oxide such as an oxide of indium and/or tin, or an oxide of indium and/or zinc, a metal halide such as copper iodide, carbon black, or a conductive polymer such as poly(3-methylthiophene), polypyrrole, or polyaniline. The formation of the anode is typically performed by, for example, a sputtering method or a vacuum deposition method in many cases. In addition, in the case of, for example, a metal fine particle made of silver or the like, a fine particle made of copper iodide or the like, carbon black, a conductive metal oxide fine particle, or conductive polymer fine powder, the anode can be formed by dispersing such particle or powder in a proper binder resin solution and applying the dispersion onto the substrate. Further, in the case of a conductive polymer, the anode can be formed by directly forming a thin film of the conductive polymer on the substrate through electrolytic polymerization or by applying the conductive polymer onto the substrate 1 (Appl. Phys. Lett., Vol. 60, p. 2711, 1992). The anode can also be formed by laminating different substances. The thickness of the anode varies depending on transparency to be required. When the transparency is required, the visible light transmittance of the anode is desirably set to 60% or more, preferably 80% or more in ordinary cases. In such cases, the thickness is typically from about 5 to 1,000 nm, preferably from about 10 to 500 nm. When the anode may be opaque, the anode may have the same transmittance as that of the substrate. In addition, another conductive material can be further formed on the anode.

(4) Hole-transporting Layer

The hole-transporting layer 4 is formed on the anode 2. The hole-injecting layer 3 can be formed therebetween. A material for the hole-transporting layer is required to satisfy the following conditions: the material needs to have high efficiency with which a hole is injected from the anode and be capable of efficiently transporting the injected hole. To this end, the material is required to have a small ionization potential, have high transparency for visible light, have a large hole mobility, be excellent in stability, and hardly produce an impurity serving as a trap at the time of the production or use. In addition, the layer is in contact with the light-emitting layer 5, and is hence required neither to quench light emitted from the light-emitting layer nor to form an exciplex between itself and the light-emitting layer to reduce the efficiency. In addition to the general requirements, the device is required to further have heat resistance when its application to an on-vehicle display is considered. Therefore, a material having a Tg of 85° C. or more is desirable.

A known compound that has heretofore been used in the layer can be used as a hole-transporting material that can be used in the present invention. Examples thereof include: an aromatic diamine which contains two or more tertiary amines and in which a nitrogen atom is substituted with two or more condensed aromatic rings (JP 5-234681 A); an aromatic amine compound having a starburst structure such as 4,4',4''-tris(1-naphthylphenylamino)triphenylamine (J. Lumin., Vols. 72 to 74, p. 985, 1997); an aromatic amine compound formed of a tetramer of triphenylamine (Chem. Commun., p. 2175, 1996); and a spiro compound such as 2,2',7,7'-tetrakis-(diphenylamino)-9,9'-spirobifluorene (Synth. Metals, Vol. 91, p. 209, 1997). One kind of those compounds may be used alone, or two or more kinds thereof may be used as a mixture as required.

In addition, examples of the material for the hole-transporting layer other than the above-mentioned compounds include polymer materials such as polyvinylcarbazole, polyvinyltriphenylamine (JP 7-53953 A), and tetraphenylbenzidine-containing polyarylene ether sulfone (Polym. Adv. Tech., Vol. 7, p. 33, 1996)

When the hole-transporting layer is formed by an application method, the hole-transporting layer is formed by: adding and dissolving one or two or more kinds of hole-transporting materials, and as required, an additive that does not serve as a trap for a hole such as a binder resin or an applicability improver to prepare an application solution; applying the solution onto the anode by a method such as a spin coating method; and drying the applied solution. Examples of the binder resin include polycarbonate, polyarylate, and polyester. When the binder resin is added in a large amount, a hole mobility reduces. Accordingly, the addition amount is desirably as small as possible and is preferably 50 wt % or less in ordinary cases.

When the hole-transporting layer is formed by the vacuum deposition method, the hole-transporting layer is formed by: loading a hole-transporting material into a crucible placed in a vacuum chamber; evacuating the inside of the vacuum chamber to about $10^{-4}$ Pa with a proper vacuum pump; and heating the crucible after the evacuation to evaporate the hole-transporting material. Thus, the hole-transporting layer is formed on the substrate having formed thereon the anode, the substrate being placed to face the crucible. The thickness of the hole-transporting layer is typically from 1 to 300 nm, preferably from 5 to 100 nm. In general, the vacuum deposition method is frequently employed for uniformly forming such thin film.

(5) Hole-injecting Layer

The hole-injecting layer 3 has been inserted between the hole-transporting layer 4 and the anode 2 for the purposes of additionally improving the hole injection efficiency and improving the adhesive force of the entire organic layer to the anode. The insertion of the hole-injecting layer provides the following effects: the initial driving voltage of the device reduces, and at the same time, an increase in voltage when the device is continuously driven at a constant current is suppressed. A material to be used in the hole-injecting layer is required to satisfy the following conditions: the material can be formed into a uniform thin film, which can be satisfactorily brought into contact with the anode, and is thermally stable, i.e., has a high glass transition temperature. The material is required to have a glass transition temperature of 100° C. or more. Further, the material is required to satisfy, for example, the following conditions: the material has a low ionization potential and hence facilitates the injection of a hole from the anode; and the material has a large hole mobility.

For this purpose, the following materials have been reported hitherto: a phthalocyanine compound (JP 63-295695 A) such as copper phthalocyanine, an organic compound such as polyaniline (Appl. Phys. Lett., Vol. 64, p. 1245, 1994) or polythiophene (Optical Materials, Vol. 9, p. 125, 1998), a sputtered carbon film (Synth. Met., Vol. 91, p. 73, 1997), a metal oxide (J. Phys. D, Vol. 29, p. 2750, 1996) such as a vanadium oxide, a ruthenium oxide, or a molybdenum oxide, and a P-type organic substance (WO 2005-109542 A1) such as 1,4,5,8-naphthalenetetracarboxylic dianhydride (NTCDA) or hexanitrilehexaazatriphenylene (HAT). One kind of those compounds may be used alone, or two or more kinds thereof may be used as a mixture as required. A thin film serving as the hole-injecting layer can be formed as in the hole-transporting layer. In the case of inorganic matter, however, the sputtering method, an electron beam deposition method, or a plasma CVD method is further employed. The thickness of the hole-injecting layer to be formed as described above is typically from 1 to 300 nm, preferably from 5 to 100 nm.

(6) Light-emitting Layer

The light-emitting layer 5 is formed on the hole-transporting layer 4. The light-emitting layer may be formed of a single light-emitting layer, or may be constituted by laminating a plurality of light-emitting layers so that the layers may be indirect contact with each other. The light-emitting layer is constituted of two host materials and a fluorescent light-emitting material or a phosphorescent light-emitting material, and the two host materials are preferably a combination of a compound represented by the general formula (1) or (2) and a compound represented by any one of the general formulae (1) to (3), particularly preferably a combination of a compound represented by the general formula (1) or (2) and a compound represented by the general formula (3).

A condensed ring derivative such as perylene or rubrene, a quinacridone derivative, phenoxazone 660, DCM1, perinone, a coumarin derivative, a pyrromethene (diazaindacene) derivative, a cyanine dye, or the like can be used as the fluorescent light-emitting material to be added to the host materials.

It is recommended to use, as the phosphorescent light-emitting material to be added to the host material, a material containing an organometallic complex including at least one metal selected from, for example, ruthenium, rhodium, palladium, silver, rhenium, osmium, iridium, platinum, and gold. Specific examples thereof include, but not limited to, the compounds disclosed in the following patent publications.

For example, WO 2009/073245 A1, WO 2009/046266 A1, WO 2007/095118 A3, WO2008/156879 A1, WO 2008/140657 A1, US 2008/261076 A1, JP 2008-542203 A, WO 2008/054584 A1, JP 2008-505925 A, JP 2007-522126 A, JP 2004-506305 A, JP 2006-513278 A, JP 2006-50596 A, WO 2006/046980 A1, WO 2005/113704 A3, US 2005/260449 A1, US 2005/2260448 A1, US 2005/214576 A1, WO 2005/076380 A3, US 2005/119485 A1, WO 2004/045001 A3, WO 2004/045000 A3, WO 2006/100888 A1, WO 2007/004380 A1, WO2007/023659 A1, WO 2008/035664 A1, JP 2003-272861 A, JP 2004-111193 A, JP 2004-319438 A, JP 2007-2080 A, JP 2007-9009 A, JP 2007-227948 A, JP 2008-91906 A, JP 2008-311607 A, JP 2009-19121 A, JP 2009-46601 A, JP 2009-114369 A, JP 2003-253128 A, JP 2003-253129 A, JP 2003-253145 A, JP 2005-38847 A, JP 2005-82598 A, JP 2005-139185 A, JP 2005-187473 A, JP 2005-220136 A, JP 2006-63080 A, JP2006-104201 A, JP2006-111623 A, JP2006-213720 A, JP2006-290891 A, JP2006-298899 A, JP 2006-298900 A, WO 2007/018067 A1, WO 2007/058080 A1, WO 2007/058104 A1, JP 2006-131561 A, JP 2008-239565 A, JP 2008-266163 A, JP 2009-57367 A, JP 2002-117978 A, JP 2003-123982 A, JP 2003-133074 A, JP 2006-93542 A, JP 2006-131524 A, JP 2006-261623 A, JP 2006-303383 A, JP 2006-303394 A, JP 2006-310479 A, JP 2007-88105 A, JP 2007-258550 A, JP2007-324309 A, JP 2008-270737 A, JP2009-96800 A, JP 2009-161524 A, WO 2008/050733 A1, JP 2003-73387 A, JP 2004-59433 A, JP 2004-155709 A, JP 2006-104132 A, JP 2008-37848 A, JP 2008-133212 A, JP 2009-57304 A, JP 2009-286716 A, JP2010-83852 A, JP2009-532546 A, JP 2009-536681 A, and JP 2009-542026 A.

Preferred examples of the phosphorescent light-emitting dopant include complexes such as Ir(ppy)3, complexes such as Ir(bt)2·acac3, and complexes such as PtOEt3, the complexes each having a noble metal device such as Ir as a central metal. Specific examples of those complexes are shown below, but the complexes are not limited to the compounds described below.

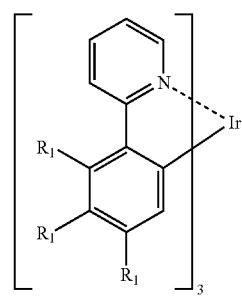

R1:H, CH3, CF3, F

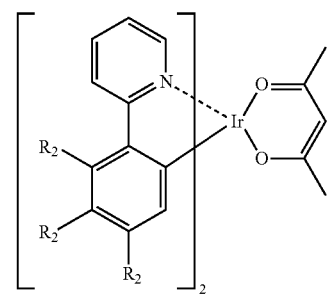

R2:H, F

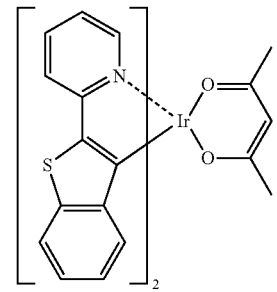

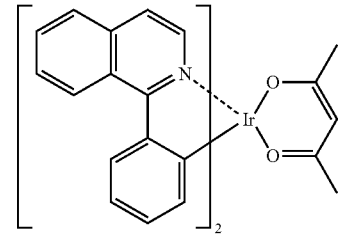

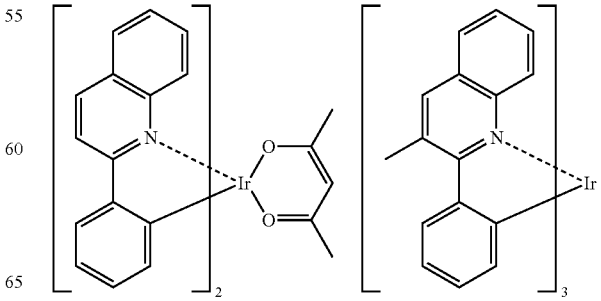

101
-continued
102
-continued
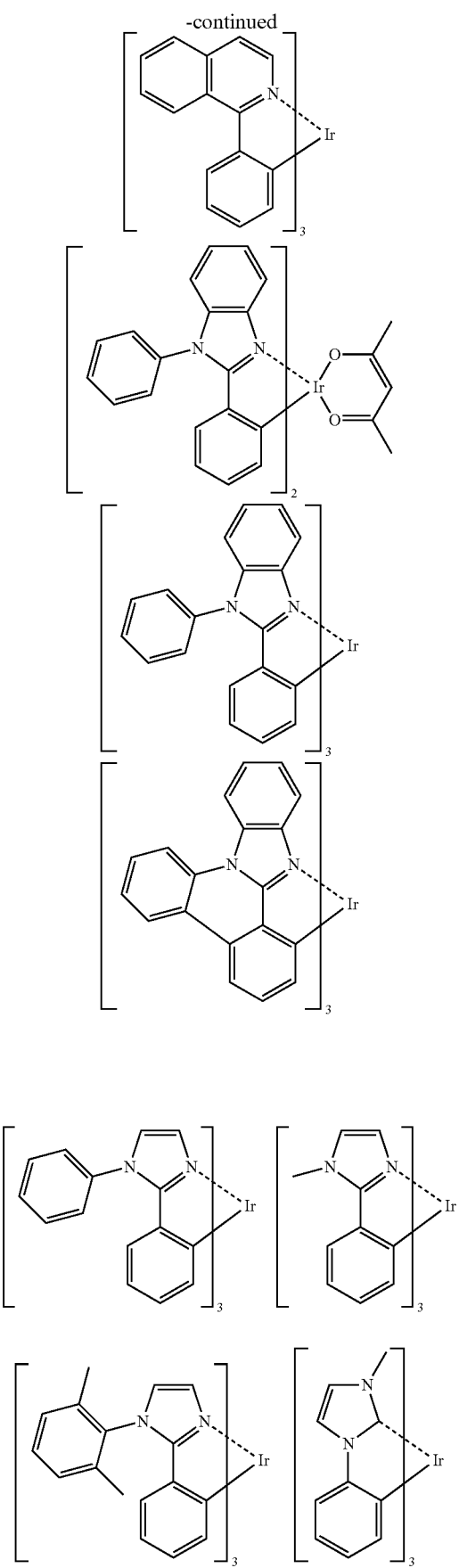
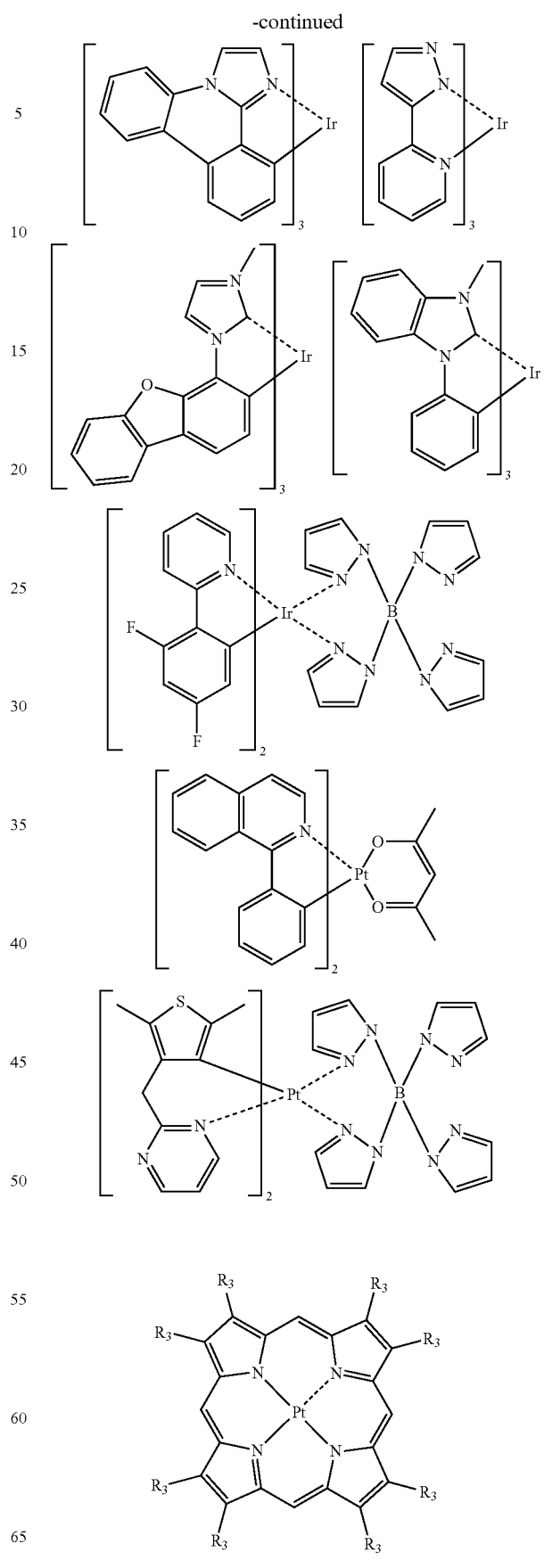

-continued

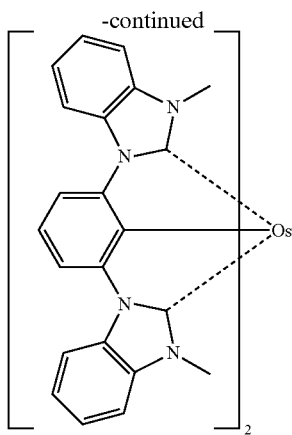

R3:CH3, CH2CH3

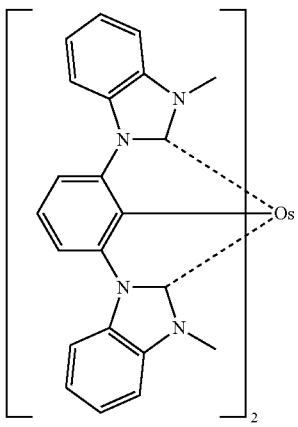

It is desirable that the content of the phosphorescent light-emitting dopant in the light-emitting layer be in the range of from 2 to 40 wt %, preferably from 5 to 30 wt %.

The thickness of the light-emitting layer, which is not particularly limited, is typically from 1 to 300 nm, preferably from 5 to 100 nm, and a thin film serving as the layer is formed by the same method as that for the hole-transporting layer.

(7) Electron-transporting Layer

The electron-transporting layer 6 is formed between the light-emitting layer 5 and the cathode 8 for the purpose of additionally improving the luminous efficiency of the device. A material for the electron-transporting layer is preferably an electron-transportable material that enables smooth injection of an electron from the cathode, and an arbitrary material that has been generally used can be used. Examples of the electron-transporting material that satisfies such condition include a metal complex (JP 59-194393 A) such as Alq3, a metal complex of 10-hydroxybenzo[h]quinoline, an oxadiazole derivative, a distyrylbiphenyl derivative, a silole derivative, a 3- or 5-hydroxyflavone metal complex, a benzoxazole metal complex, a benzothiazole metal complex, trisbenzimidazolylbenzene (U.S. Pat. No. 5,645,948 A), a quinoxaline compound (JP 6-207169 A), a phenanthroline derivative (JP 5-331459 A), 2-t-butyl-9,10-N,N'-dicyanoanthraquinonediimine, n-type hydrogenated amorphous silicon carbide, n-type zinc sulfide, and n-type zinc selenide.

The thickness of the electron-transporting layer is typically from 1 to 300 nm, preferably from 5 to 100 nm. The electron-transporting layer is formed through lamination on the light-emitting layer by the application method or the vacuum deposition method as in the hole-transporting layer. The vacuum deposition method is typically employed.

(8) Cathode

The cathode 8 serves to inject an electron into the electron-transporting layer 6. Although the material to be used in the anode 2 can be used as a material to be used as the cathode, a metal having a low work function is preferred for efficient electron injection, and a proper metal such as tin, magnesium, indium, calcium, aluminum, or silver, or an alloy thereof is used. Specific examples of the cathode include low-work function alloy electrodes made of a magnesium-silver alloy, a magnesium-indium alloy, and an aluminum-lithium alloy.

The thickness of the cathode is typically the same as that of the anode. When a metal layer that has a high work function and is stable against the air is further formed on the cathode formed of a low-work function metal for the purpose of protecting the cathode, the stability of the device improves. A metal such as aluminum, silver, copper, nickel, chromium, gold, or platinum is used for the purpose.

Further inserting an extremely thin insulating film (having a thickness of from 0.1 to 5 nm) made of LiF, $MgF_2$, $Li_2O$, or the like as the electron-injecting layer 7 between the cathode 8 and the electron-transporting layer 6 is also an effective method of improving the efficiency of the device.

It should be noted that a structure in inverse relation to that illustrated in FIG. 1 is permitted, i.e., the cathode 8, the electron-injecting layer 7, the electron-transporting layer 6, the light-emitting layer 5, the hole-transporting layer 4, the hole-injecting layer 3, and the anode 2 can be laminated in the stated order on the substrate 1. As described in the foregoing, the organic EL device of the present invention can be formed between two substrates at least one of which has high transparency. In this case as well, a layer can be added or omitted as required.

The organic EL device of the present invention can be any one of a single device, an device formed of structures placed in an array manner, and a structure in which the anode and the cathode are placed in an X-Y matrix manner. According to the organic EL device of the present invention, when the light-emitting layer is formed by using a mixed host formed of two host materials, and a specific compound is used as at least one of the host materials, an device that has high luminous efficiency and is significantly improved in driving stability while being capable of being driven at a low voltage is obtained, and the device can exhibit excellent performance in its application to a full-color or multi-color panel.

The present invention is described in more detail below by way of Examples. However, the present invention is not limited to Examples below, and can be carried out in various modes as long as the modes do not deviate from the gist thereof.

EXAMPLES

Example 1

Each thin film was formed by a vacuum deposition method at a degree of vacuum of $4.0 \times 10^{-4}$ Pa on a glass substrate on which an anode formed of ITO having a thickness of 150 nm had been formed. First, copper phthalocyanine (CuPC) was formed as a hole-injecting layer having a thickness of 20 nm on the ITO. Next, 4,4-bis[N-

(1-naphthyl)-N-phenylamino]biphenyl (NPB) was formed as a hole-transporting layer having a thickness of 20 nm. Next, Compound 1-4 as a first host, Compound 3-37 as a second host, and tris(2-phenylpyridine)iridium(III) (Ir(PPy)$_3$) as a light-emitting layer guest were co-deposited from vapor deposition sources different from one another to form a light-emitting layer having a thickness of 30 nm. At this time, a vapor deposition rate ratio among the first host, the second host, and Ir(PPy) 3 (deposition rate ratio among vaporized products) was 47:47:6. Next, aluminum(III) bis (2-methyl-8-quinolinato)4-phenylphenolate (BAlq) was formed into a hole-blocking layer having a thickness of 10 nm. Next, tris(8-hydroxyquinolinato)aluminum(III) (Alq$_3$) was formed into an electron-transporting layer having a thickness of 40 nm. Further, lithium fluoride (LiF) was formed into an electron-injecting layer having a thickness of 0.5 nm on the electron-transporting layer. Finally, aluminum (Al) was formed into a cathode having a thickness of 100 nm on the electron-injecting layer. Thus, an organic EL device was produced.

An external power source was connected to the resultant organic EL device and a DC voltage was applied to the device. As a result, an emission spectrum having a local maximum wavelength of 517 nm was observed and hence it was found that light emission from Ir(PPy)$_3$ was obtained. Table 1 shows the luminance, external quantum efficiency, and luminance half lifetime of the produced organic EL device.

Examples 2 to 4

Organic EL devices were each produced in the same manner as in Example 1 except that in Example 1, a compound shown in Table 1 was used as the light-emitting layer second host. An external power source was connected to each of the resultant organic EL devices and a DC voltage was applied to the device. As a result, an emission spectrum having a local maximum wavelength of 517 nm was observed for each of the organic EL devices and hence it was found that light emission from Ir(PPy)$_3$ was obtained. Table 1 shows the luminance, external quantum efficiency, and luminance half lifetime of each of the produced organic EL devices.

Examples 11 to 15 (Comparative)

Organic EL devices were each produced in the same manner as in Example 1 except that in Example 1, a compound shown in Table 1 was used alone as the light-emitting layer host. It should be noted that a host amount was set to the same amount as the total of the first host and second host in Example 1, and a guest amount was similarly set. A power source was connected to each of the resultant organic EL devices and a DC voltage was applied to the device. As a result, an emission spectrum having a local maximum wavelength of 517 nm was observed for each of the organic EL devices and hence it was found that light emission from Ir(PPy)$_3$ was obtained. Table 1 shows the luminance, external quantum efficiency, and luminance half lifetime of each of the produced organic EL devices.

Table 1 shows the luminance, external quantum efficiency (initial characteristic), and luminance half lifetime (lifetime characteristic) of each of the produced organic EL devices. The luminance and the external quantum efficiency are values at a driving current of 2.5 mA/cm$^2$, and the luminance half time is a value at an initial luminance of 1,000 cd/m$^2$. Compound Nos. are numbers attached to the chemical formulae.

TABLE 1

| Example No. | First host (EA) | Second host (EA) | Luminance (cd/m$^2$) | External quantum efficiency (%) | Luminance half time (h) |
|---|---|---|---|---|---|
| 1 | 1-4 (3.03 eV) | 3-37 (2.40 eV) | 946 | 10.1 | 10,969 |
| 2 | 1-4 (3.03 eV) | 3-7 (2.58 eV) | 1,010 | 10.8 | 10,197 |
| 3 | 1-4 (3.03 eV) | 3-13 (2.60 eV) | 1,005 | 10.8 | 10,485 |
| 4 | 1-4 (3.03 eV) | 3-22 (2.57 eV) | 1,059 | 11.4 | 13,649 |
| 11 | 1-4 (3.03 eV) | — | 998 | 10.7 | 9,634 |
| 12 | 3-37 (2.40 eV) | — | 536 | 5.8 | 2,795 |
| 13 | 3-7 (2.58 eV) | — | 639 | 6.8 | 7,481 |
| 14 | 3-13 (2.60 eV) | — | 323 | 3.5 | 3,718 |
| 15 | 3-22 (2.57 eV) | — | 302 | 3.3 | 4,499 |

Comparison between Examples 1 to 4 of the present invention and Examples 11 to 15 in Table 1 shows that when two kinds of compounds each having a specific skeleton are used as light-emitting layer hosts, the luminance and the external quantum efficiency improve, and the luminance half time significantly lengthens. Those results have revealed that according to the present invention, an organic EL phosphorescent device showing high efficiency and a good lifetime characteristic can be realized.

Example 5

Each thin film was formed by a vacuum deposition method at a degree of vacuum of 4.0×10$^{-4}$ Pa on a glass substrate on which an anode formed of ITO having a thickness of 150 nm had been formed. First, CuPC was formed into a hole-injecting layer having a thickness of 20 nm on the ITO. Next, NPB was formed into a hole-transporting layer having a thickness of 20 nm. Next, Compound 2-5 as a first host, Compound 3-37 as a second host, and Ir(PPy)$_3$ as a light-emitting layer guest were co-deposited from vapor deposition sources different from one another to form a light-emitting layer having a thickness of 30 nm. At this time, a vapor deposition rate ratio among the first host, the second host, and Ir(PPy)$_3$ was 47:47:6. Next, BAlq was formed as a hole-blocking layer having a thickness of 10 nm. Next, Alq$_3$ was formed as an electron-transporting layer having a thickness of 40 nm. Further, lithium fluoride (LiF) was formed as an electron-injecting layer having a thickness of 0.5 nm on the electron-transporting layer. Finally, aluminum (Al) was formed as a cathode having a thickness of 100 nm on the electron-injecting layer. Thus, an organic EL device was produced.

An external power source was connected to the resultant organic EL device and a DC voltage was applied to the device. As a result, an emission spectrum having a local maximum wavelength of 517 nm was observed and hence it was found that light emission from Ir(PPy)$_3$ was obtained. Table 2 shows the luminance, external quantum efficiency, and luminance half lifetime of the produced organic EL device.

Examples 6 and 7

Organic EL devices were each produced in the same manner as in Example 5 except that in Example 5, a compound shown in Table 2 was used as the light-emitting layer second host. An external power source was connected to each of the resultant organic EL devices and a DC voltage was applied to the device. As a result, an emission spectrum having a local maximum wavelength of 517 nm was observed for each of the organic EL devices and hence it was found that light emission from Ir(PPy)$_3$ was obtained. Table 2 shows the luminance, external quantum efficiency, and luminance half lifetime of each of the produced organic EL devices.

Examples 16 to 19 (Comparative)

Organic EL devices were each produced in the same manner as in Example 5 except that in Example 5, a compound shown in Table 2 was used alone as the light-emitting layer host. It should be noted that a host amount was set to the same amount as the total of the first host and second host in Example 5. An external power source was connected to each of the resultant organic EL devices and a DC voltage was applied to the device. As a result, an emission spectrum having a local maximum wavelength of 517 nm was observed for each of the EL devices and hence it was found that light emission from Ir(PPy)$_3$ was obtained.

Table 2 shows the luminance, external quantum efficiency, and luminance half lifetime of each of the produced organic EL devices. The luminance and the external quantum efficiency are values at a driving current of 2.5 mA/cm$^2$, and the luminance half time is a value at an initial luminance of 1,000 cd/m$^2$.

Example 20 (Comparative)

Each thin film was formed by a vacuum deposition method at a degree of vacuum of 4.0×10$^{-4}$ Pa on a glass substrate on which an anode formed of ITO having a thickness of 150 nm had been formed. First, CuPC was formed as a hole-injecting layer having a thickness of 20 nm on the ITO. Next, NPB was formed as a hole-transporting layer having a thickness of 20 nm. Next, Compound 2-5 as a first host, Compound A shown below as a second host, and Ir(PPy)$_3$ as a light-emitting layer guest were co-deposited from vapor deposition sources different from one another to form a light-emitting layer having a thickness of 30 nm. At this time, a vapor deposition rate ratio among the first host, the second host, and Ir(PPy)$_3$ was 47:47:6. Next, BAlq was formed as a hole-blocking layer having a thickness of 10 nm. Next, Alq$_3$ was formed as an electron-transporting layer having a thickness of 40 nm. Further, lithium fluoride (LiF) was formed as an electron-injecting layer having a thickness of 0.5 nm on the electron-transporting layer. Finally, aluminum (Al) was formed as a cathode having a thickness of 100 nm on the electron-injecting layer. Thus, an organic EL device was produced.

In addition, an organic EL device using Compound A shown below alone as the light-emitting layer host was similarly produced. An external power source was connected to each of the resultant organic EL devices and a DC voltage was applied to the device. As a result, an emission spectrum having a local maximum wavelength of 517 nm was observed for both the organic EL devices and hence it was found that light emission from Ir(PPy)$_3$ was obtained. Table 2 shows the luminance, external quantum efficiency, and luminance half lifetime of each of the produced organic EL devices.

TABLE 2

| Example No. | First host (EA) | Second host (EA) | Luminance (cd/m$^2$) | External quantum efficiency (%) | Luminance half time (h) |
|---|---|---|---|---|---|
| 5 | 2-5 (3.03 eV) | 3-37 (2.40 eV) | 935 | 9.9 | 10,599 |
| 6 | 2-5 (3.03 eV) | 3-7 (2.58 eV) | 831 | 8.9 | 9,060 |
| 7 | 2-5 (3.03 eV) | 3-13 (2.60 eV) | 811 | 8.7 | 10,052 |
| 16 | 2-5 (3.03 eV) | — | 771 | 8.2 | 6,339 |
| 17 | 3-37 (2.40 eV) | — | 536 | 5.8 | 2,795 |
| 18 | 3-7 (2.58 eV) | — | 639 | 6.8 | 7,481 |
| 19 | 3-13 (2.60 eV) | — | 323 | 3.5 | 3,718 |
| 20 | 2-5 (3.03 eV) | A (2.46 eV) | 772 | 8.2 | 6,354 |
|  | A (2.46 eV) | — | 480 | 5.1 | 7,202 |

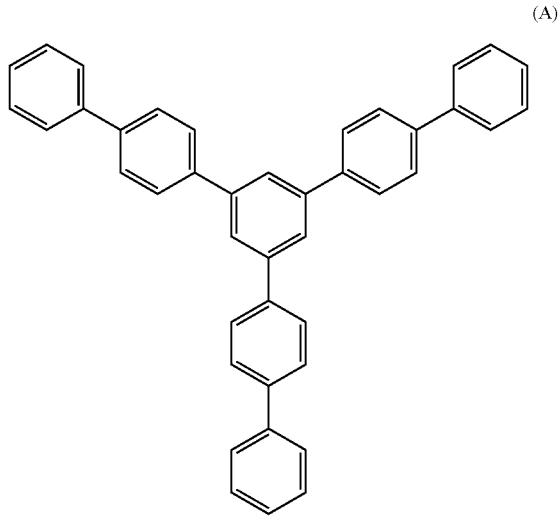 [SMILES: c1ccc(-c2ccc(-c3cc(-c4ccc(-c5ccccc5)cc4)cc(-c4ccc(-c5ccccc5)cc4)c3)cc2)cc1]

(A)

Comparison between Examples 5 to 7 of the present invention and Examples 16 to 19 in Table 2 shows that when two kinds of compounds each having a specific skeleton are used as light-emitting layer hosts, the luminance and the external quantum efficiency improve, and the luminance half time significantly lengthens. Those results have revealed that according to the present invention, an organic EL phosphorescent device showing high efficiency and a good lifetime characteristic can be realized.

Table 2 shows that when the mixed host of Compound 2-5 and Compound A, and a single host of Compound A and a single host of Compound 2-5 (Example 16) are compared, the use of the mixed host of Compound 2-5 and Compound A as the light-emitting layer host improves the luminance and the external quantum efficiency, but shortens the luminance half time. The result has shown that when a mixed host of compounds each having a skeleton except a specific skeleton is used as a light-emitting layer host, a driving lifetime characteristic may deteriorate.

Example 8

Each thin film was formed by a vacuum deposition method at a degree of vacuum of $4.0 \times 10^{-4}$ Pa on a glass substrate on which an anode formed of ITO having a thickness of 150 nm had been formed. First, CuPC was formed as a hole-injecting layer having a thickness of 25 nm on the ITO. Next, NPB was formed as a first hole-transporting layer having a thickness of 10 nm. Further, 4,4',4"-tris(N-carbazolyl)-triphenylamine (TCTA) was formed as a second hole-transporting layer having a thickness of 10 nm. Next, Compound 1-90 as a first host, Compound 3-4 as a second host, and tris[1-(4'-cyanophenyl)-3-methylbenzimidazol-2-ylidene-$C^2,C^{2'}$]-iridium(III) (Ir(cn-pmic)$_3$) as a light-emitting layer guest were co-deposited from vapor deposition sources different from one another to form a light-emitting layer having a thickness of 30 nm. At this time, a vapor deposition rate ratio among the first host, the second host, and Ir(cn-pmic)$_3$ was 45:45:10. Next, 2,9-dimethyl-4,7-diphenyl-1,10-phenanthroline (BCP) was formed as a hole-blocking layer having a thickness of 10 nm. Next, Alq$_3$ was formed as an electron-transporting layer having a thickness of 25 nm. Further, lithium fluoride (LiF) was formed as an electron-injecting layer having a thickness of 0.5 nm on the electron-transporting layer. Finally, aluminum (Al) was formed as a cathode having a thickness of 100 nm on the electron-injecting layer. Thus, an organic EL device was produced.

An external power source was connected to the resultant organic EL device and a DC voltage was applied to the device. As a result, an emission spectrum having a local maximum wavelength of 460 nm was observed and hence it was found that light emission from Ir(cn-pmic)$_3$ was obtained. Table 3 shows the luminance, external quantum efficiency, and luminance half lifetime of the produced organic EL device.

Example 21 (Comparative)

An organic EL device was produced in the same manner as in Example 8 except that in Example 8, only Compound 1-90 was used as the light-emitting layer host. A host amount was set to the same amount as the total of the first host and second host in Example 8. An external power source was connected to the resultant organic EL device and a DC voltage was applied to the device. As a result, an emission spectrum having a local maximum wavelength of 460 nm was observed for each of the organic EL devices and hence it was found that light emission from Ir(cn-pmic)$_3$ was obtained. Table 3 shows the luminance, external quantum efficiency, and luminance half lifetime of the produced organic EL device.

Example 22 (Comparative)

An organic EL device was each produced in the same manner as in Example 8 except that in Example 8, only Compound 3-4 was used as the light-emitting layer host. A host amount was set to the same amount as the total of the first host and second host in Example 8. An external power source was connected to the resultant organic EL device and a DC voltage was applied to the device. As a result, an emission spectrum having a local maximum wavelength of 460 nm was observed for each of the organic EL devices and hence it was found that light emission from Ir(cn-pmic)$_3$ was obtained. Table 3 shows the luminance, external quantum efficiency, and luminance half lifetime of the produced organic EL device. The luminance and the external quantum efficiency are values at a driving current of 2.5 mA/cm$^2$, and the luminance half time is a value at an initial luminance of 1,000 cd/m$^2$.

TABLE 3

| Example No. | 1st host (EA) | 2nd host (EA) | Luminance (cd/m$^2$) | External quantum efficiency (%) | Luminance half time (h) |
|---|---|---|---|---|---|
| 8 | 1-90 (2.58 eV) | 3-4 (2.70 eV) | 394 | 13.0 | 196 |
| 21 | 1-90 (2.58 eV) | — | 372 | 12.0 | 139 |
| 22 | 3-4 (2.70 eV) | — | 363 | 11.4 | 114 |

Comparison between Example 8 of the present invention and Examples 21 to 22 in Table 3 shows that when two kinds of compounds each having a specific skeleton are used as light-emitting layer hosts, the luminance and the external quantum efficiency improve, and the luminance half time significantly lengthens. Those results have revealed that according to the present invention, an organic EL phosphorescent device showing high efficiency and a good lifetime characteristic can be realized.

INDUSTRIAL APPLICABILITY

The organic EL device of the present invention uses specific compounds as a mixed host, and hence has the lowest excited triplet energy high enough to confine the lowest excited triplet energy of a phosphorescent light-emitting molecule while being capable of being driven at a low voltage. Accordingly, the device shows no energy outflow from the inside of its light-emitting layer, can achieve high efficiency and a long lifetime, and has a high technological value in its application to, for example, flat panel displays (such as a cellular phone display device, an on-vehicle display device, an OA computer display device, and a television), light sources each taking advantage of its feature as a surface emitter (such as illumination, a light source for a copying machine, and backlight sources for a liquid crystal display and meters), display boards, and marker lamps.

The invention claimed is:

1. An organic electroluminescent device, comprising one or more light-emitting layers between an anode and a cathode opposite to each other, wherein:

at least one of the light-emitting layers contains two host materials and at least one light-emitting dopant; and one of the two host materials comprises a host material selected from compounds each represented by any one of the following general formulae (1) to (2), and another of the two host materials comprises a host material selected from compounds each represented by the following general formula (3):

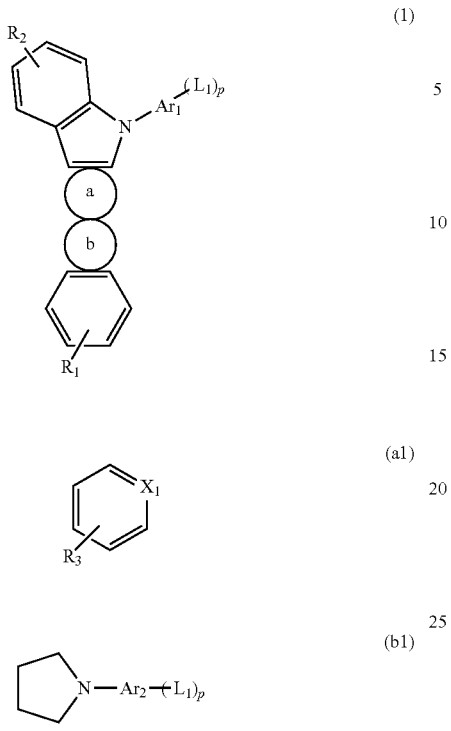

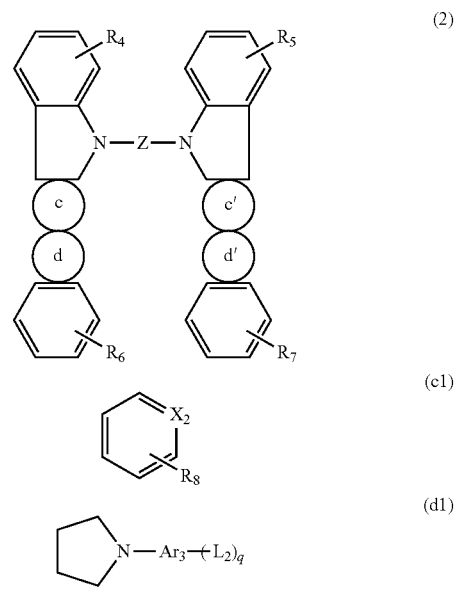

wherein a ring a represents an aromatic ring or heterocycle represented by the formula (a1) condensed at arbitrary positions of two adjacent rings, X1 represents C—R, a ring b represents a heterocycle represented by the formula (b1) condensed at arbitrary positions of two adjacent rings, Ar1 and Ar2 each represent an aromatic hydrocarbon group having 6 to 22 carbon atoms or a monocyclic aromatic heterocyclic group having 3 to 6 carbon atoms, and at least one of Ar1 and Ar2 represents a substituted or unsubstituted monocyclic aromatic heterocyclic group having 3 to 6 carbon atoms, L1 represents an aromatic hydrocarbon group having 6 to 22 carbon atoms, an aromatic heterocyclic group having 3 to 16 carbon atoms, or a group obtained by linking 2 to 10 of the groups, the aromatic hydrocarbon groups or aromatic heterocyclic groups in Ar1, Ar2, and L1 may each have a substituent, p represents an integer of from 0 to 7 and when p represents 2 or more, L1s may be identical to or different from each other, and R and R1 to R3 each independently represent hydrogen, an alkyl group having 1 to 20 carbon atoms, an aralkyl group having 7 to 38 carbon atoms, an alkenyl group having 2 to 20 carbon atoms, an alkynyl group having 2 to 20 carbon atoms, a dialkylamino group having 2 to 40 carbon atoms, a diarylamino group having 12 to 44 carbon atoms, a diaralkylamino group having 14 to 76 carbon atoms, an acyl group having 2 to 20 carbon atoms, an acyloxy group having 2 to 20 carbon atoms, an alkoxy group having 1 to 20 carbon atoms, an alkoxycarbonyl group having 2 to 20 carbon atoms, an alkoxycarbonyloxy group having 2 to 20 carbon atoms, an alkylsulfonyl group having 1 to 20 carbon atoms, an aromatic hydrocarbon group having 6 to 22 carbon atoms, or an aromatic heterocyclic group having 3 to 16 carbon atoms, and may each have a substituent;

wherein a ring c and a ring c' each represent an aromatic ring or heterocycle represented by the formula (c1) condensed at an arbitrary position of an adjacent ring, a ring d and a ring d' each represent a heterocycle represented by the formula (d1) condensed at an arbitrary position of an adjacent ring, and the ring c and the ring c', or the ring d and the ring d' may be identical to or different from each other, X2 represents C—R' or N, Z represents an aromatic hydrocarbon group having 6 to 22 carbon atoms, an aromatic heterocyclic group having 3 to 16 carbon atoms, or a divalent linking group obtained by linking 2 to 10 of the groups, but a group linked to N comprises an aromatic hydrocarbon group having 6 to 22 carbon atoms or a monocyclic aromatic heterocyclic group having 3 to 6 carbon atoms, Ar3 represents an aromatic hydrocarbon group having 6 to 22 carbon atoms or a monocyclic aromatic heterocyclic group having 3 to 6 carbon atoms, L2 represents an aromatic hydrocarbon group having 6 to 22 carbon atoms, an aromatic heterocyclic group having 3 to 16 carbon atoms, or a group obtained by linking 2 to 10 of the groups, the aromatic hydrocarbon groups or aromatic heterocyclic groups in Z, Ar3, and L2 may each have a substituent, q represents an integer of from 0 to 7, and when q represents 2 or more, L2s may be identical to or different from each other, and R' and R4 to R8 each independently represent hydrogen, an alkyl group having 1 to 20 carbon atoms, an aralkyl group having 7 to 38 carbon atoms, an alkenyl group having 2 to 20 carbon atoms, an alkynyl group having 2 to 20 carbon atoms, a dialkylamino group having 2 to 40 carbon atoms, a diarylamino group having 12 to 44 carbon atoms, a diaralkylamino group having 14 to 76 carbon atoms, an acyl group having 2 to 20 carbon atoms, an acyloxy group having 2 to 20 carbon atoms, an alkoxy group having 1 to 20 carbon atoms, an alkoxycarbonyl group having 2 to 20 carbon atoms, an alkoxycarbonyloxy group having 2 to 20 carbon atoms, an alkylsulfonyl group having 1 to 20 carbon atoms, an aromatic hydrocarbon group having 6 to 22 carbon atoms, or an aromatic heterocyclic group having 3 to 16 carbon atoms, and may each have a substituent;

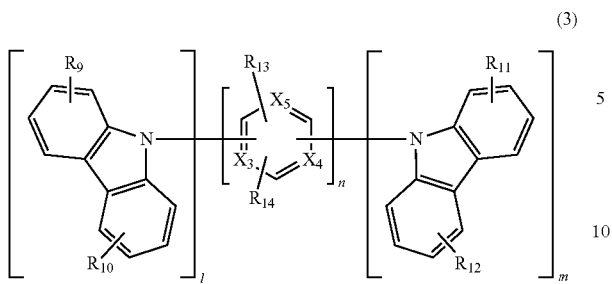

wherein R9 to R12 each independently represent hydrogen, an alkyl group having 1 to 20 carbon atoms, an acyl group having 2 to 20 carbon atoms, or an alkoxy group having 2 to 20 carbon atoms, l and m each represent an integer of 1 or 2, n represents 5 or 6, R13 and R14 each independently represent hydrogen or an alkyl group having 1 to 20 carbon atoms, and X3 to X5 each independently represent C—H or N, and when n represents 2 or more, R13s, R14s, and X3s to X5s may be identical to or different from each other.

2. An organic electroluminescent device, comprising one or more light-emitting layers between an anode and a cathode opposite to each other, wherein:

at least one of the light-emitting layers contains two host materials and at least one light-emitting dopant; and one of the two host materials comprises a host material selected from compounds each represented by the following general formula (2), and another of the two host materials comprises a host material selected from compounds each represented by the following general formula (3)

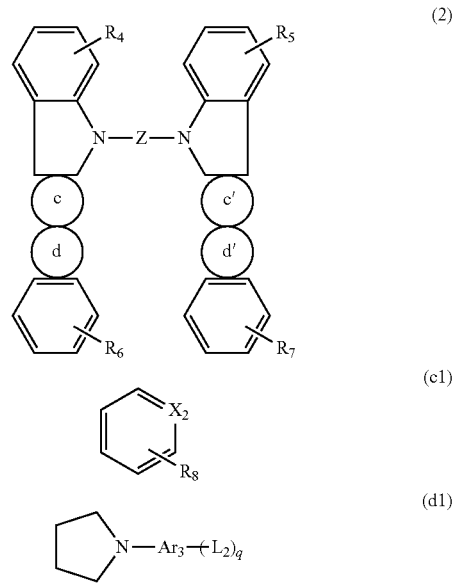

wherein a ring c and a ring c' each represent an aromatic ring or heterocycle represented by the formula (c1) condensed at an arbitrary position of an adjacent ring, a ring d and a ring d' each represent a heterocycle represented by the formula (d1) condensed at an arbitrary position of an adjacent ring, and the ring c and the ring c', or the ring d and the ring d' may be identical to or different from each other, X2 represents C—R' or N, Z represents an aromatic hydrocarbon group having 6 to 22 carbon atoms, an aromatic heterocyclic group having 3 to 16 carbon atoms, or a divalent linking group obtained by linking 2 to 10 of the groups, but a group linked to N comprises an aromatic hydrocarbon group having 6 to 22 carbon atoms or a monocyclic aromatic heterocyclic group having 3 to 6 carbon atoms, Ar3 represents an aromatic hydrocarbon group having 6 to 22 carbon atoms or a monocyclic aromatic heterocyclic group having 3 to 6 carbon atoms, L2 represents an aromatic hydrocarbon group having 6 to 22 carbon atoms, an aromatic heterocyclic group having 3 to 16 carbon atoms, or a group obtained by linking 2 to 10 of the groups, the aromatic hydrocarbon groups or aromatic heterocyclic groups in Z, Ar3, and L2 may each have a substituent, q represents an integer of from 0 to 7, and when q represents 2 or more, L2s may be identical to or different from each other, and R' and R4 to R8 each independently represent hydrogen, an alkyl group having 1 to 20 carbon atoms, an aralkyl group having 7 to 38 carbon atoms, an alkenyl group having 2 to 20 carbon atoms, an alkynyl group having 2 to 20 carbon atoms, a dialkylamino group having 2 to 40 carbon atoms, a diarylamino group having 12 to 44 carbon atoms, a diaralkylamino group having 14 to 76 carbon atoms, an acyl group having 2 to 20 carbon atoms, an acyloxy group having 2 to 20 carbon atoms, an alkoxy group having 1 to 20 carbon atoms, an alkoxycarbonyl group having 2 to 20 carbon atoms, an alkoxycarbonyloxy group having 2 to 20 carbon atoms, an alkylsulfonyl group having 1 to 20 carbon atoms, an aromatic hydrocarbon group having 6 to 22 carbon atoms, or an aromatic heterocyclic group having 3 to 16 carbon atoms, and may each have a substituent;

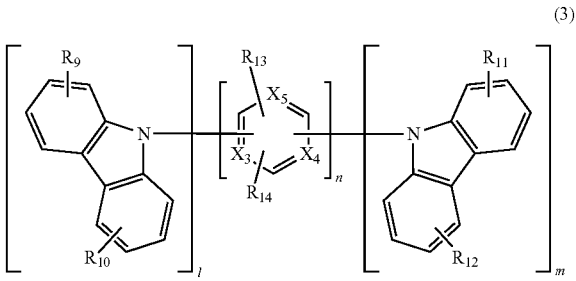

wherein R9 to R12 each independently represent hydrogen, an alkyl group having 1 to 20 carbon atoms, an acyl group having 2 to 20 carbon atoms, or an alkoxy group having 2 to 20 carbon atoms, l and m each represent an integer of 1 or 2, n represents an integer of from 1 to 6, R13 and R14 each independently represent hydrogen or an alkyl group having 1 to 20 carbon atoms, and X3 to X5 each independently represent C—H or N, and when n represents 2 or more, R13s, R14s, and X3s to X5s may be identical to or different from each other, and wherein in the general formula (3), at least two X3, X4, or X5 out of all X3s, X4s and X5s in the general formula (3) are N, and at least one carbazole group is bonded to the adjacent six-membered aromatic ring at the meta or para position.

3. An organic electroluminescent device, comprising one or more light-emitting layers between an anode and a cathode opposite to each other, wherein:

at least one of the light-emitting layers contains two host materials and at least one light-emitting dopant; and one of the two host materials comprises a host material selected from compounds each represented by the following general formula (2), and another of the two host materials comprises a host material selected from compounds each represented by the following general formula (3):

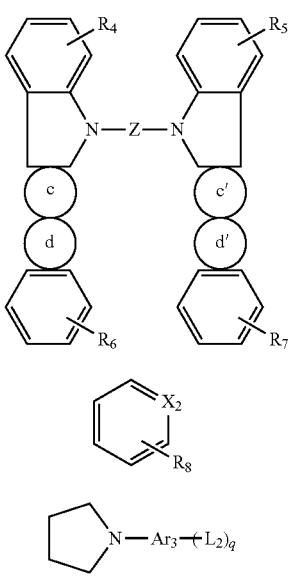

(2)

(c1)

(d1)

wherein a ring c and a ring c' each represent an aromatic ring or heterocycle represented by the formula (c1) condensed at an arbitrary position of an adjacent ring, a ring d and a ring d' each represent a heterocycle represented by the formula (d1) condensed at an arbitrary position of an adjacent ring, and the ring c and the ring c', or the ring d and the ring d' may be identical to or different from each other, $X_2$ represents C—R' or N, Z represents an aromatic hydrocarbon group having 6 to 22 carbon atoms, an aromatic heterocyclic group having 3 to 16 carbon atoms, or a divalent linking group obtained by linking 2 to 10 of the groups, but a group linked to N comprises an aromatic hydrocarbon group having 6 to 22 carbon atoms or a monocyclic aromatic heterocyclic group having 3 to 6 carbon atoms, Ar3 represents an aromatic hydrocarbon group having 6 to 22 carbon atoms or a monocyclic aromatic heterocyclic group having 3 to 6 carbon atoms, L2 represents an aromatic hydrocarbon group having 6 to 22 carbon atoms, an aromatic heterocyclic group having 3 to 16 carbon atoms, or a group obtained by linking 2 to 10 of the groups, the aromatic hydrocarbon groups or aromatic heterocyclic groups in Z, Ar3, and L2 may each have a substituent, q represents an integer of from 0 to 7, and when q represents 2 or more, L2s may be identical to or different from each other, and R' and R4 to R8 each independently represent hydrogen, an alkyl group having 1 to 20 carbon atoms, an aralkyl group having 7 to 38 carbon atoms, an alkenyl group having 2 to 20 carbon atoms, an alkynyl group having 2 to 20 carbon atoms, a dialkylamino group having 2 to 40 carbon atoms, a diarylamino group having 12 to 44 carbon atoms, a diaralkylamino group having 14 to 76 carbon atoms, an acyl group having 2 to 20 carbon atoms, an acyloxy group having 2 to 20 carbon atoms, an alkoxy group having 1 to 20 carbon atoms, an alkoxycarbonyl group having 2 to 20 carbon atoms, an alkoxycarbonyloxy group having 2 to 20 carbon atoms, an alkylsulfonyl group having 1 to 20 carbon atoms, an aromatic hydrocarbon group having 6 to 22 carboncarbon atoms, or an aromatic heterocyclic group having 3 to 16 carbon atoms, and may each have a substituent;

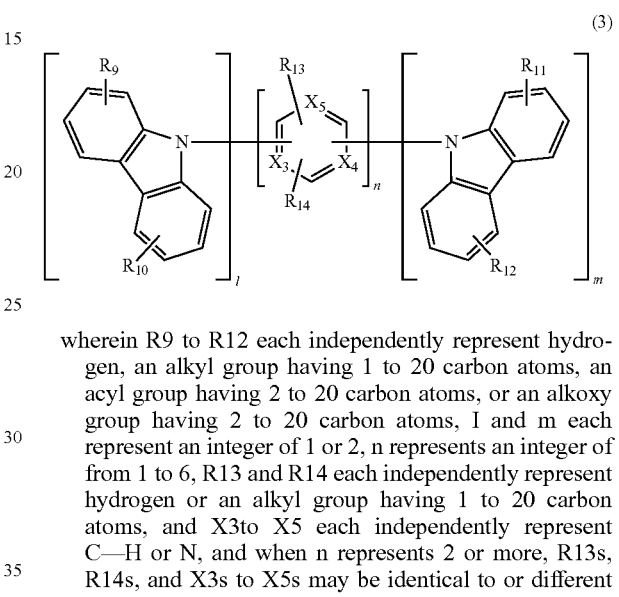

(3)

wherein R9 to R12 each independently represent hydrogen, an alkyl group having 1 to 20 carbon atoms, an acyl group having 2 to 20 carbon atoms, or an alkoxy group having 2 to 20 carbon atoms, l and m each represent an integer of 1 or 2, n represents an integer of from 1 to 6, R13 and R14 each independently represent hydrogen or an alkyl group having 1 to 20 carbon atoms, and X3 to X5 each independently represent C—H or N, and when n represents 2 or more, R13s, R14s, and X3s to X5s may be identical to or different from each other, and wherein in the general formula (3), at least one carbazole group is bonded to the adjacent six-membered aromatic ring at the meta or para position.

4. An organic electroluminescent device, comprising one or more light-emitting layers between an anode and a cathode opposite to each other, wherein:

at least one of the light-emitting layers contains two host materials and at least one light-emitting dopant; and one of the two host materials comprises a host material selected from compounds each represented by the following general formula (2), and another of the two host materials comprises a host material selected from compounds each represented by the following general formula (3):

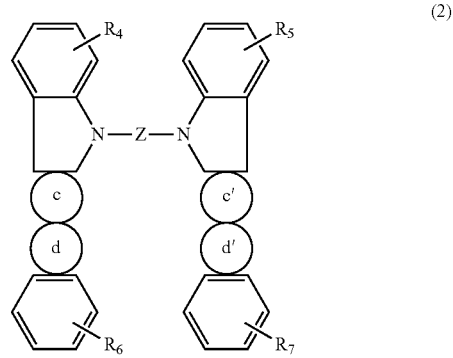

(2)

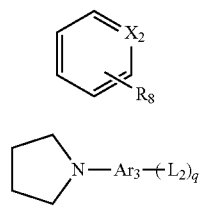

wherein a ring c and a ring c' each represent an aromatic ring or heterocycle represented by the formula (c1) condensed at an arbitrary position of an adjacent ring, a ring d and a ring d' each represent a heterocycle represented by the formula (d1) condensed at an arbitrary position of an adjacent ring, and the ring c and the ring c', or the ring d and the ring d' may be identical to or different from each other, X2 represents C—R' or N, Z represents an aromatic hydrocarbon group having 6 to 22 carbon atoms, an aromatic heterocyclic group having 3 to 16 carbon atoms, or a divalent linking group obtained by linking 2 to 10 of the groups, but a group linked to N comprises an aromatic hydrocarbon group having 6 to 22 carbon atoms or a monocyclic aromatic heterocyclic group having 3 to 6 carbon atoms, Ar3 represents an aromatic hydrocarbon group having 6 to 22 carbon atoms or a monocyclic aromatic heterocyclic group having 3 to 6 carbon atoms, L2 represents an aromatic hydrocarbon group having 6 to 22 carbon atoms, an aromatic heterocyclic group having 3 to 16 carbon atoms, or a group obtained by linking 2 to 10 of the groups, the aromatic hydrocarbon groups or aromatic heterocyclic groups in Z, Ar3, and L2 may each have a substituent, q represents an integer of from 0 to 7, and when q represents 2 or more, L2s may be identical to or different from each other, and R' and R4 to R8 each independently represent hydrogen, an alkyl group having 1 to 20 carbon atoms, an aralkyl group having 7 to 38 carbon atoms, an alkenyl group having 2 to 20 carbon atoms, an alkynyl group having 2 to 20 carbon atoms, a dialkylamino group having 2 to 40 carbon atoms, a diarylamino group having 12 to 44 carbon atoms, a diaralkylamino group having 14 to 76 carbon atoms, an acyl group having 2 to 20 carbon atoms, an acyloxy group having 2 to 20 carbon atoms, an alkoxy group having 1 to 20 carbon atoms, an alkoxycarbonyl group having 2 to 20 carbon atoms, an alkoxycarbonyloxy group having 2 to 20 carbon atoms, an alkylsulfonyl group having 1 to 20 carbon atoms, an aromatic hydrocarbon group having 6 to 22 carbon atoms, or an aromatic heterocyclic group having 3 to 16 carbon atoms, and may each have a substituent;

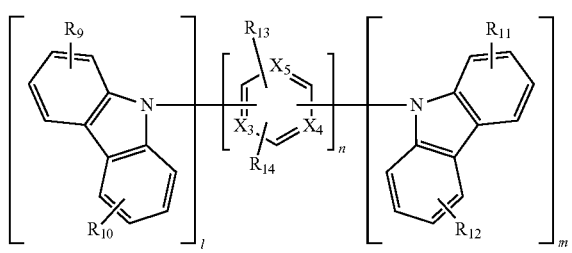

wherein R9 to R12 each independently represent hydrogen, an alkyl group having 1 to 20 carbon atoms, an acyl group having 2 to 20 carbon atoms, or an alkoxy group having 2 to 20 carbon atoms, l and m each represent an integer of 1 or 2, n represents an integer of from 1 to 6, R13 and R14 each independently represent hydrogen or an alkyl group having 1 to 20 carbon atoms, and X3 to X5 each independently represent C—H or N, and when n represents 2 or more, R13s, R14s, and X3s to X5s may be identical to or different from each other, and wherein in the general formula (3), at least four X3, X4, or X5 out of all X3s, X4s and X5s in the general formula (3) are N.

* * * * *